(12) United States Patent
Mizokami et al.

(10) Patent No.: US 12,146,887 B2
(45) Date of Patent: Nov. 19, 2024

(54) METHOD FOR ASSISTING PREDICTION OF EXACERBATION OF RESPIRATORY INFECTION, AND DEVICE TO ASSIST IN PREDICTING EXACERBATION OF RESPIRATORY INFECTION

(71) Applicants: NATIONAL CENTER FOR GLOBAL HEALTH AND MEDICINE, Tokyo (JP); SYSMEX CORPORATION, Kobe (JP)

(72) Inventors: Masashi Mizokami, Ichikawa (JP); Masaya Sugiyama, Ichikawa (JP); Norio Ohmagari, Shinjuku-ku (JP); Noriko Kinoshita, Shinjuku-ku (JP); Youichi Takahama, Kobe (JP); Kazuki Nakabayashi, Kobe (JP)

(73) Assignees: NATIONAL CENTER FOR GLOBAL HEALTH AND MEDICINE, Tokyo (JP); SYSMEX CORPORATION, Kobe (JP)

( * ) Notice: Subject to any disclaimer, the term of this patent is extended or adjusted under 35 U.S.C. 154(b) by 673 days.

(21) Appl. No.: 17/231,209

(22) Filed: Apr. 15, 2021

(65) Prior Publication Data
US 2021/0325408 A1  Oct. 21, 2021

(30) Foreign Application Priority Data

Apr. 16, 2020  (JP) .................... 2020-073665
Jun. 11, 2020  (JP) .................... 2020-101833

(51) Int. Cl.
| | | |
|---|---|---|
| G01N 33/564 | (2006.01) | |
| G01N 33/537 | (2006.01) | |
| G01N 33/569 | (2006.01) | |
| G01N 33/68 | (2006.01) | |

(52) U.S. Cl.
CPC ....... *G01N 33/6893* (2013.01); *G01N 33/537* (2013.01); *G01N 33/56983* (2013.01); *G01N 2333/54* (2013.01); *G01N 2333/70535* (2013.01); *G01N 2333/70596* (2013.01); *G01N 2800/122* (2013.01); *G01N 2800/125* (2013.01); *G01N 2800/50* (2013.01)

(58) Field of Classification Search
CPC ............. G01N 33/6893; G01N 33/537; G01N 33/56983; G01N 2333/54; G01N 2333/70535; G01N 2333/70596; G01N 2800/122; G01N 2800/125; G01N 2800/50; G01N 33/6863; G01N 2800/12; G01N 2800/26; G01N 33/6866; G01N 33/6869; G01N 33/86; G01N 33/564; G01N 33/543; G01N 2333/745; G01N 2333/8139; G01N 2800/065; G01N 2800/102; G01N 2800/52; G01N 2800/56; G16B 30/00
See application file for complete search history.

(56) References Cited

U.S. PATENT DOCUMENTS

2021/0311074 A1* 10/2021 Miyazaki ............... G16H 50/50

FOREIGN PATENT DOCUMENTS

JP  6081699 B2  2/2017

OTHER PUBLICATIONS

Huang et al., "An Interferon-g-Related Cytokine Storm in SARS Patients", Journal of Medical Virology 75:185-194 (2005) (Year: 2005).*
Martha M. Monic, Respiratory Syncytial Virus Synergizes with Th2 Cytokines to Induce Optimal Levels of TARC/CCL171. J Immunol Aug. 1, 2007; 179 (3): 1648-1658. (Year: 2007).*
CDC, Human Coronavirus Types, published 2020 retrieved from https://www.cdc.gov/coronavirus/types.html on Nov. 21, 2023 (Year: 2020).*
Notice of Reasons for Refusal, dated Aug. 3, 2021, issued by the Japanese Patent Office in Japanese Application No. 2020-101833.
Brandon Michael Henry et al., "Hematologic, biochemical and immune biomarker abnormalities associated with severe illness and mortality in coronavirus disease 2019 (COVID-19): a meta-analysis", Clin Chem Lab Med, 2020, vol. 58, No. 7, pp. 1021-1028.
Communication pursuant to Article 94(3) EPC, dated Jul. 6, 2022, issued by the European Patent Office in European Patent Application 21168754.6.
Extended European Search Report, dated Sep. 16, 2021, issued by the European Patent Office in European Patent Application No. 21168754.6.
Kao-Jean Huang et al., "An Interferon-gamma-Related Cytokine Storm in SARS Patients", Journal of Medical Virology, vol. 75, No. 2, Jan. 1, 2004, pp. 185-194 (10 pages total).
Eu Suk Kim et al., "Clinical Progression and Cytokine Profiles of Middle East Respiratory Syndrome Coronavirus Infection", Journal of Korean Medical Medicine, vol. 31, No. 11, Jan. 1, 2016, pp. 1717-1725 (9 pages total).

(Continued)

*Primary Examiner* — Gary Counts
(74) *Attorney, Agent, or Firm* — Sughrue Mion, PLLC

(57) ABSTRACT

Disclosed is a method for assisting prediction of exacerbation of respiratory infection, comprising measuring a biomarker in a specimen collected from a subject suffering from a respiratory infection or a subject suspected of having a respiratory infection, wherein the biomarker is at least one selected from the group consisting of IFNλ3, CCL17, CXCL11, IP-10, IL-6 and CXCL9, and a measured value of the biomarker is used as an index to predict exacerbation of the respiratory infection.

11 Claims, 38 Drawing Sheets

Specification includes a Sequence Listing.

(56) References Cited

OTHER PUBLICATIONS

Yingxia Liu et al., "Elevated plasma levels of selective cytokines in COVID-19 patients reflect viral load and lung injury", National Science Review, vol. 7, No. 6, Mar. 9, 2020, pp. 1003-1011 (9 pages total).

Masaya Sugiyama, et al., "Serum CCL17 level becomes a predictive marker to distinguish between mild/moderate and severe/critical disease in patients with COVID-19", Gene, 2021, pp. 1-9, vol. 766, No. 145145.

* cited by examiner

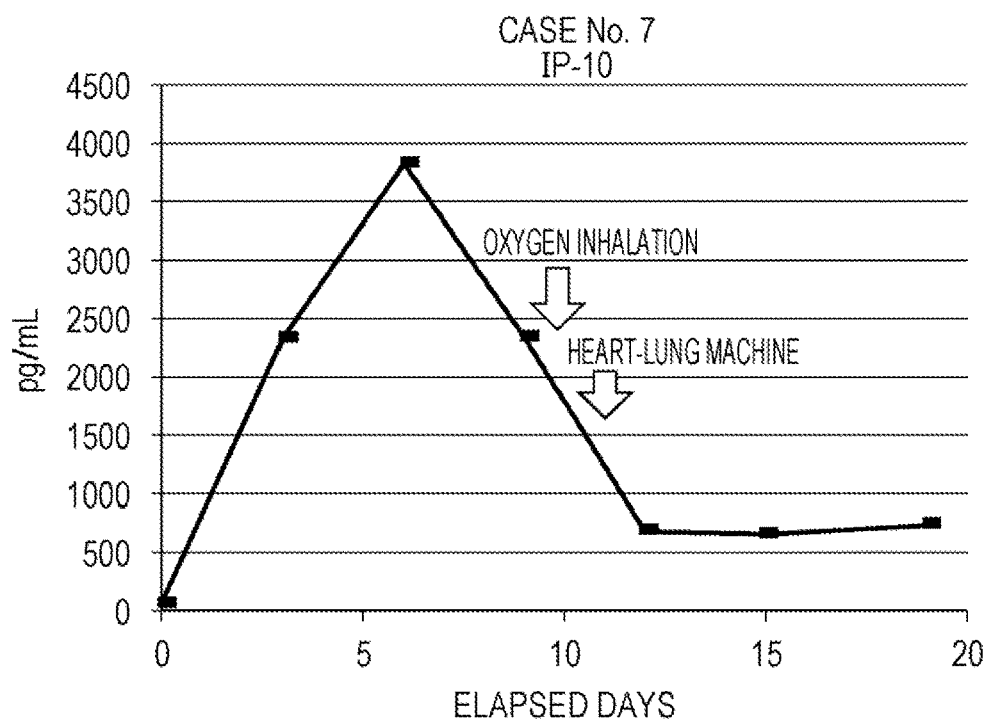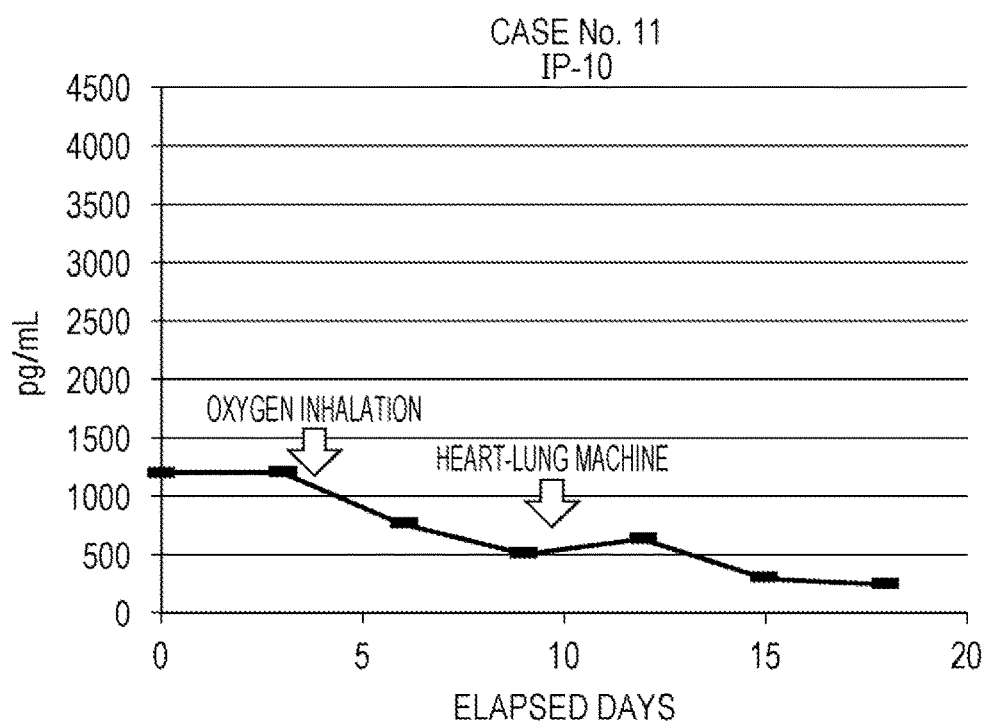

METHOD FOR ASSISTING PREDICTION OF EXACERBATION OF RESPIRATORY INFECTION, AND DEVICE TO ASSIST IN PREDICTING EXACERBATION OF RESPIRATORY INFECTION

CROSS REFERENCE TO RELATED APPLICATIONS

This application claims priority from prior Japanese Patent Application No. 2020-73665 filed on Apr. 16, 2020, and Japanese Patent Application No. 2020-101833, filed on Jun. 11, 2020, entitled "Method for assisting prediction of exacerbation of respiratory infection, method for monitoring measured value of biomarker, reagent kit used for these methods, device and computer program to assist in predicting exacerbation of respiratory infection", the entire contents of which are incorporated herein by reference.

FIELD OF THE INVENTION

The present invention relates to a method for assisting exacerbation of respiratory infection. The present invention relates to a device to assist in predicting exacerbation of respiratory infection.

BACKGROUND

Patients with respiratory infections are often mild and do not require hospitalization, but some patients become severe and need to be hospitalized for treatment. Since it is necessary to give priority to treatment of severely ill patients, there is a great need for a means to predict exacerbation of respiratory infection.

In view of the above circumstances, the present inventors have attempted to search for a biomarker that can predict exacerbation. An object of the present invention is to provide a new means for predicting exacerbation of respiratory infection by using such biomarker.

Japanese Examined Patent No. 6081699 describes that IL (Interleukin)-28B (also called IFNλ3), a type of cytokine, in serum of patient with chronic hepatitis C was detected by a method that specifically measures IL-28B. However, Japanese Examined Patent No. 6081699 does not describe that IFNλ3 was measured in order to predict exacerbation of respiratory infection.

SUMMARY OF THE INVENTION

The scope of the present invention is defined solely by the appended claims, and is not affected to any degree by the statements within this summary.

The present inventors have found that IFNλ3 (Interferonλ3), CCL17 (CC chemokine ligand 17), CXCL11 (CXC chemokine ligand 11), IP-10 (Interferon-inducible Protein-10), IL-6 and CXCL9 (CXC chemokine ligand 9) can be used as biomarkers for predicting exacerbation of respiratory infection, thereby completing the invention.

The present invention provides a method for assisting prediction of exacerbation of respiratory infection, comprising: measuring a biomarker in a specimen collected from a subject suffering from a respiratory infection or a subject suspected of having a respiratory infection, wherein the biomarker is at least one selected from the group consisting of IFNλ3, CCL17, CXCL11, IP-10, IL-6 and CXCL9, and a measured value of the biomarker is an index to predict exacerbation of the respiratory infection.

The present invention provides a method for assisting prediction of exacerbation of respiratory infection, comprising: monitoring a measured value of a biomarker in a specimen collected from a subject suffering from a respiratory infection or a subject suspected of having a respiratory infection, the monitoring comprising: acquiring measured values of the biomarker using specimens collected from the subject at a plurality of time points, wherein the biomarker is at least one selected from the group consisting of IFNλ3, CCL17, CXCL11, IP-10, IL-6 and CXCL9, and the measured values are indices to predict exacerbation of the respiratory infection.

The present invention provides a device to assist in predicting exacerbation of respiratory infection, including a computer including a processor and a memory under control of the processor, in which a computer program for making the computer execute calculating a measured value of a biomarker in a specimen collected from a subject suffering from a respiratory infection or a subject suspected of having a respiratory infection, and outputting the measured value of the biomarker is recorded in the memory, and the measured value of the biomarker is an index to predict exacerbation of the respiratory infection, and the biomarker contains at least one selected from the group consisting of IFNλ3, CCL17, CXCL11, IP-10, IL-6 and CXCL9.

BRIEF DESCRIPTION OF THE DRAWINGS

FIG. 7A is a graph showing transition of IP-10 concentration in serum of a patient in case No. 7;

FIG. 7B is a graph showing transition of IP-10 concentration in serum of a patient in case No. 11;

DETAILED DESCRIPTION OF THE PREFERRED EMBODIMENTS

Figure 1A:
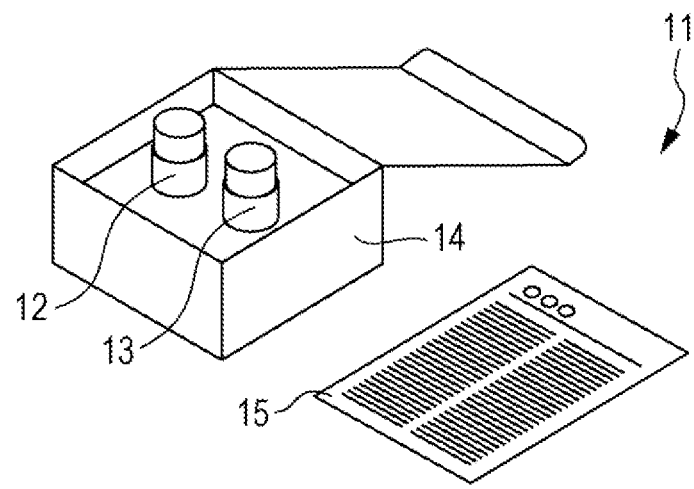
FIG. 1A is a schematic diagram showing an example of the reagent kit of the present embodiment.

In the method for assisting prediction of exacerbation of respiratory infection of the present embodiment (hereinafter, also referred to as "prediction method"), first, as a biomarker in a specimen collected from a subject, at least one selected from the group consisting of IFNλ3, CCL17, CXCL11, IP-10, IL-6 and CXCL9 is measured. In the prediction method of the present embodiment, the measured value of the biomarker serves as an index to predict exacerbation of the respiratory infection.

Respiratory infection refers to a disease caused by infection of respiratory organ such as nasal cavity, pharynx, trachea, bronchi or alveoli with a pathogen. The pathogen is not particularly limited, and examples thereof include viruses, bacteria, fungi, parasites and the like. Examples of the virus include coronavirus, influenza virus, and the like. The coronavirus is not particularly limited, and examples thereof include α-coronavirus, β-coronavirus, γ-coronavirus, and δ-coronavirus. Examples of the β-coronavirus include SARS-CoV-2, SARS-CoV, HCoV-OC43, HCoV- HKU1, Bat SL-CoV-WIV1, BtCoV-HKU4, BtCoV-HKU5, MERS-CoV, BtCoV-HKU9, and the like.

Examples of the subject in the present embodiment include a patient suffering from a respiratory infection and a person suspected of having a respiratory infection. The patient suffering from a respiratory infection refers to a person whose respiratory infection has been confirmed due to detection of a pathogen or the like and has not yet become severe. The person suspected of having a respiratory infection include, for example, those who have cold symptoms such as fever, cough, runny nose and sore throat and/or symptoms specific to prescribed respiratory infections such as feeling of dyspnea, short breath during exertion and abnormal taste and smell, and those coming into contact with and those suspected of coming into contact with patient with respiratory infection. Contact with patient with respiratory infection refers to, for example, an act such as talking with the patient within a distance of 1 m, staying in a closed space where the patient is present, and being splashed with saliva, coughing or the like of the patient.

In one embodiment, exacerbation of respiratory infection refers to develop pneumonia requiring oxygen inhalation or be a condition requiring intensive care management including mechanical ventilation management.

The specimen is not particularly limited as long as it is a liquid sample collected from a subject and suspected of containing the biomarker. Examples of such liquid sample include blood samples, cerebrospinal fluid, sputum, bronchoalveolar lavage fluid, nasopharyngeal swab, lymph fluid, urine, stool, saliva, and the like. Among them, blood samples are preferred. Examples of the blood sample include whole blood, plasma and serum, and plasma and serum are particularly preferable.

When insoluble contaminants such as cells are contained in the specimen, for example, impurities may be removed from the specimen by a known means such as centrifugal separation and filtration. The specimen may be diluted with an appropriate aqueous medium as necessary. Such an aqueous medium is not particularly limited as long as it does not interfere with the measurement described later, and examples thereof include water, physiological saline, a buffer solution, and the like. The buffer solution is not particularly limited as long as it has a buffering effect at a pH near neutrality (for example, a pH of 6 or more and 8 or less). Examples of the buffer solution include Good buffers such as HEPES, MES, Tris and PIPES, phosphate buffered saline (PBS), and the like.

The biomarker measured by the prediction method of the present embodiment is one or more protein molecules selected from IFNλ3, CCL17, CXCL11, IP-10, IL-6 and CXCL9. IFNλ3, also called IL-28B, is a protein consisting of 200 amino acids encoded by a gene of about 1.5 Kb located on chromosome 19. IFNλ3 has 25 signal peptides at N-terminus, and the signal peptide is cleaved when IFNλ3 is secreted extracellularly. CCL17 is also called TARC (Thymus- and activation-regulated chemokine) and is a type of Th2 type chemokine. CXCL11 is a chemokine also called I-TAC (Interferon-inducible T-cell Chemoattractant), and is a ligand for CXCR3 receptor. IP-10, also called CXCL10, is a type of Th1 type chemokine. IL-6 is a type of TH2 type cytokine. CXCL9, also called MIG (Monokine induced by interferon γ), is a ligand for CXCR3 receptor and is a type of Th1 type chemokine as well as IP-10. These protein molecules themselves are known, and their amino acid sequences can be acquired from known databases such as NCBI (National Center for Biotechnology Information). For example, IFNλ3 may have an amino acid sequence represented by SEQ ID NO: 1 or may have an amino acid sequence represented by SEQ ID NO: 2.

In the present embodiment, it is preferable to acquire measured values of two or more biomarkers selected from IFNλ3, CCL17, CXCL11, IP-10, IL-6 and CXCL9 from the viewpoint of improving accuracy of prediction of exacerbation. Examples of the two or more biomarkers include one of the following combinations:

a combination of IFNλ3 and at least one selected from the group consisting of CCL17, CXCL11, IP-10, IL-6 and CXCL9;

a combination of CCL17 and at least one selected from the group consisting of IFNλ3, CXCL11, IP-10, IL-6 and CXCL9;

a combination of CXCL11 and at least one selected from the group consisting of IFNλ3, CCL17, IP-10, IL-6 and CXCL9;

a combination of IP-10 and at least one selected from the group consisting of IFNλ3, CCL17, CXCL11, IL-6 and CXCL9;

a combination of IL-6 and at least one selected from the group consisting of IFNλ3, CCL17, CXCL11, IP-10, and CXCL9; and a combination of CXCL9 and at least one selected from the group consisting of IFNλ3, CCL17, CXCL11, IP-10 and IL-6.

In the present embodiment, it is particularly preferable to acquire a measured value of IFNλ3 and a measured value of CCL17.

A known method can be used for measuring the biomarker, and the method is not particularly limited. In the present embodiment, a method of capturing a biomarker using a substance capable of specifically binding to the biomarker is preferable. The biomarker contained in the specimen can be measured by detecting the biomarker captured by such a substance by a method known in the art. The measured value of the biomarker may be a value that reflects an amount or concentration in the specimen. The measured value may be a concentration or a value reflecting the concentration calculated based on a measurement result of a calibrator. The "value reflecting the concentration" depends on a type of labeling substance described later, and examples thereof include a measured value of fluorescence intensity, a measured value of emission intensity, a measured value of radioactivity, and the like.

Examples of the substance capable of specifically binding to the biomarker include an antibody, an aptamer and the like, among which an antibody is particularly preferable. An antibody against the biomarker is not particularly limited as long as it is an antibody capable of specifically binding to the biomarker. Such an antibody may be any of monoclonal antibodies, polyclonal antibodies, and fragments thereof (for example, Fab, F(ab')2, etc.). A commercially available antibody may be used.

As an antibody capable of specifically binding to IFNλ3, for example, a monoclonal antibody having a heavy chain variable region domain and a light chain variable region domain described in any one of (1) to (5) below or a fragment thereof may be used.

(1) A heavy chain variable region domain including a heavy chain complementarity determining region 1 including amino acid sequences 31 to 35, a heavy chain complementarity determining region 2 including amino acid sequences 50 to 66, and a heavy chain complementarity determining region 3 including amino acid sequences 99 to 113 in an amino acid sequence represented by SEQ ID NO: 3, and a light chain variable region domain including a light chain complementarity determining region 1 including amino acid sequences 24 to 38, a light chain complementarity determining region 2 including amino acid sequences 54 to 60, and a light chain complementarity determining region 3 including amino acid sequences 93 to 101 in an amino acid sequence represented by SEQ ID NO: 4;

(2) A heavy chain variable region domain including a heavy chain complementarity determining region 1 including amino acid sequences 31 to 35, a heavy chain complementarity determining region 2 including amino acid sequences 50 to 66, and a heavy chain complementarity determining region 3 including amino acid sequences 99 to 109 in an amino acid sequence represented by SEQ ID NO: 5, and a light chain variable region domain including a light chain complementarity determining region 1 including amino acid sequences 24 to 38, a light chain complementarity determining region 2 including amino acid sequences 54 to 60, and a light chain complementarity determining region 3 including amino acid sequences 93 to 101 in an amino acid sequence represented by SEQ ID NO: 6;

(3) A heavy chain variable region domain including a heavy chain complementarity determining region 1 including amino acid sequences 31 to 35, a heavy chain complementarity determining region 2 including amino acid sequences 50 to 66, and a heavy chain complementarity determining region 3 including amino acid sequences 99 to 106 in an amino acid sequence represented by SEQ ID NO: 7, and a light chain variable region domain including a light chain complementarity determining region 1 including amino acid sequences 24 to 38, a light chain complementarity determining region 2 including amino acid sequences 54 to 60, and a light chain complementarity determining region 3 including amino acid sequences 93 to 101 in an amino acid sequence represented by SEQ ID NO: 8;

(4) A heavy chain variable region domain including a heavy chain complementarity determining region 1 including amino acid sequences 31 to 35, a heavy chain complementarity determining region 2 including amino acid sequences 50 to 66, and a heavy chain complementarity determining region 3 including amino acid sequences 99 to 106 in an amino acid sequence represented by SEQ ID NO: 9, and a light chain variable region domain including a light chain complementarity determining region 1 including amino acid sequences 24 to 38, a light chain complementarity determining region 2 including amino acid sequences 54 to 60, and a light chain complementarity determining region 3 including amino acid sequences 93 to 101 in an amino acid sequence represented by SEQ ID NO: 10; or (5) A heavy chain variable region domain including a heavy chain complementarity determining region 1 including amino acid sequences 31 to 35, a heavy chain complementarity determining region 2 including amino acid sequences 50 to 66, and a heavy chain complementarity determining region 3 including amino acid sequences 99 to 106 in an amino acid sequence represented by SEQ ID NO: 11, and a light chain variable region domain including a light chain complementarity determining region 1 including amino acid sequences 24 to 38, a light chain complementarity determining region 2 including amino acid sequences 54 to 60, and a light chain complementarity determining region 3 including amino acid sequences 93 to 101 in an amino acid sequence represented by SEQ ID NO: 12.

A method for measuring a biomarker using an antibody is not particularly limited and can be appropriately selected from known immunoassays. In the present embodiment, an enzyme-linked immunosorbent assay (ELISA method) is preferred, and a sandwich ELISA method being particularly preferred. As an example of the measurement step, the case of measuring a biomarker in the specimen by a sandwich ELISA method will be described below.

First, a complex containing a biomarker, an antibody for capturing the biomarker (hereinafter also referred to as "capture antibody") and an antibody for detecting the biomarker (hereinafter also referred to as "detection antibody") is formed on a solid phase. When the specimen contains a biomarker, a complex can be formed by mixing the specimen, a capture antibody, and a detection antibody. Then, a solution containing the complex is brought into contact with a solid phase capable of immobilizing the capture antibody, whereby the complex can be formed on the solid phase. Alternatively, a solid phase preliminarily immobilized with the capture antibody may be used. That is, a solid phase immobilized with the capture antibody, the specimen, and the detection antibody are brought into contact with each other, whereby the complex can be formed on the solid phase. When both the capture antibody and the detection antibody are monoclonal antibodies, it is preferable that the epitopes be different from each other.

The mode of immobilization of the capture antibody on the solid phase is not particularly limited. For example, the capture antibody and the solid phase may be bound directly, or the capture antibody and the solid phase may be indirectly bound via another substance. Examples of the direct binding include physical adsorption and the like. Examples of the indirect bond include a bond via a combination of biotins and avidins. In this case, by preliminarily modifying the capture antibody with biotins and previously binding avidins to the solid phase, the capture antibody and the solid phase can be indirectly bound via the bond between the biotins and the avidins. The biotins include biotin and biotin analogs such as desthiobiotin. The avidins include avidin and analogs of avidins such as streptavidin and tamavidin (registered trademark).

The material of the solid phase is not particularly limited. For example, the material can be selected from organic polymer compounds, inorganic compounds, biopolymers, and the like. Examples of the organic polymer compound include latex, polystyrene, polypropylene, and the like. Examples of the inorganic compound include magnetic bodies (iron oxide, chromium oxide, ferrite, and the like), silica, alumina, glass, and the like. Examples of the biopolymer include insoluble agarose, insoluble dextran, gelatin, cellulose, and the like. Two or more of these may be used in combination. The shape of the solid phase is not particularly limited, and examples thereof include particles, membranes, microplates, microtubes, test tubes, and the like. Among them, particles are preferable, and magnetic particles are particularly preferable.

In the present embodiment, B/F (Bound/Free) separation for removing an unreacted free component not forming a complex may be performed between the process of forming the complex and the process of detecting the complex. The unreacted free component refers to a component not constituting a complex. Examples thereof include capture antibodies not bound to the biomarker, detection antibodies, and the like. The means of B/F separation is not particularly limited, and when the solid phase is a particle, B/F separation can be performed by recovering only the solid phase capturing the complex by centrifugation. When the solid phase is a container such as a microplate or a microtube, B/F separation can be performed by removing a liquid containing an unreacted free component. When the solid phase is a magnetic particle, B/F separation can be performed by aspirating and removing a liquid containing an unreacted free component by a nozzle while magnetically constraining the magnetic particles with a magnet, which is preferable from the viewpoint of automation. After removing the unreacted free component, the solid phase capturing the complex may be washed with a suitable aqueous medium such as PBS.

Moreover, a measured value of a biomarker contained in the specimen can be acquired by detecting the complex formed on the solid phase by a method known in the art. For example, when an antibody labeled with a labeling substance is used as a detection antibody, the measured value of the marker in the liquid sample can be acquired by detecting a signal generated by the labeling substance. Alternatively, also when a labeled secondary antibody against the detection antibody is used, the measured value of the biomarker in the liquid sample can be acquired in the same manner.

As an example of a method for measuring a biomarker using an antibody, the immune complex transfer method described in Japanese Laid-Open Patent Publication No. H01-254868 can be also used.

The phrase "detecting a signal" herein includes qualitatively detecting the presence or absence of a signal, quantifying a signal intensity, and semi-quantitatively detecting the intensity of a signal. Semi-quantitative detection means to show the intensity of the signal in stages like "no signal generated", "weak", "medium", "strong", and the like. In the present embodiment, it is preferable to detect the intensity of a signal quantitatively or semi-quantitatively.

The labeling substance is not particularly limited. For example, the labeling substance may be a substance which itself generates a signal (hereinafter also referred to as "signal generating substance") or a substance which catalyzes the reaction of other substances to generate a signal. Examples of the signal generating substance include fluorescent substances, radioactive isotopes, and the like. Examples of the substance that catalyzes the reaction of other substances to generate a detectable signal include enzymes. Examples of the enzymes include alkaline phosphatase, peroxidase, β-galactosidase, luciferase, and the like. Examples of the fluorescent substances include fluorescent dyes such as fluorescein isothiocyanate (FITC), rhodamine and Alexa Fluor (registered trademark), fluorescent proteins such as GFP, and the like. Examples of the radioactive isotopes include $^{125}I$, $^{14}C$, $^{32}P$, and the like. Among them, an enzyme is preferable as a labeling substance, and alkaline phosphatase and peroxidase are particularly preferable.

Methods for detecting a signal themselves are known in the art. In the present embodiment, a measurement method according to the type of signal derived from the labeling substance may be appropriately selected. For example, when the labeling substance is an enzyme, signals such as light and color generated by reacting a substrate for the enzyme can be measured by using a known apparatus such as a spectrophotometer.

The substrate of the enzyme can be appropriately selected from known substrates according to the type of the enzyme. For example, when alkaline phosphatase (ALP) is used as the enzyme, examples of the substrate include chemiluminescent substrates such as CDP-Star (registered trademark) (disodium 4-chloro-3-(methoxyspiro[1,2-dioxetane-3,2'-(5'-chloro)tricyclo[3.3.1.1³,⁷]decan]-4-yl)phenyl phosphate) and CSPD (registered trademark) (disodium 3-(4-methoxyspiro[1,2-dioxetane-3,2-(5'-chloro)tricyclo[3.3.1.1.13,7]decan]-4-yl)phenyl phosphate), and chromogenic substrates such as 5-bromo-4-chloro-3-indolyl phosphate (BCIP), disodium 5-bromo-6-chloro-indolyl phosphate, and p-nitrophenyl phosphate. When peroxidase is used as the enzyme, examples of the substrate include chemiluminescent substrates such as luminol and derivatives thereof, and chromogenic substrates such as 2,2'-azinobis(3-ethylbenzothiazoline-6-ammonium sulfonate) (ABTS), 1,2-phenylenediamine (OPD) and 3,3',5,5'-tetramethylbenzidine (TMB).

When the labeling substance is a radioactive isotope, radiation as a signal can be measured using a known apparatus such as a scintillation counter. When the labeling substance is a fluorescent substance, fluorescence as a signal can be measured using a known apparatus such as a fluorescence microplate reader. The excitation wavelength and the fluorescence wavelength can be appropriately determined according to the type of fluorescent substance used.

The detection result of the signal can be used as the measured value of the biomarker. For example, when quantitatively detecting the intensity of a signal, the signal intensity value itself or a value acquired from the measured value can be used as the measured value of the biomarker. Examples of the value acquired from the measured value of the signal intensity include a value acquired by subtracting the measured value of a negative control sample or the background value from the measured value, a value acquired by applying the measured value to a calibration curve, and the like. The negative control sample can be appropriately selected, and examples thereof include a specimen obtained from a mildly ill patient (for example, an infectious disease patient who has recovered without becoming severe), a specimen obtained from a healthy person, and the like.

In the present embodiment, it is preferable to measure the biomarker contained in the specimen by an immunoassay such as an EIA method or an ELISA method. Biomarkers can be measured using commercially available devices and reagents such as the HISCL series (manufactured by Sysmex Corporation) and the Bio-Plex Multiplex System (manufactured by Bio-Rad Laboratories, Inc.).

In the present embodiment, the measured values of the biomarkers described above can be used as an index indicating whether or not a respiratory infection of a subject is exacerbated. For example, by comparing the acquired measured value of the biomarker with a threshold value corresponding to the biomarker, the measured value of the biomarker may be used as an index suggesting that a possibility of exacerbation of respiratory infection of the subject is high or low. In the present embodiment, the possibility of exacerbation of respiratory infection is a risk of exacerbation of the respiratory infection of the subject after a lapse of a predetermined period (for example, 1 day to 1 month) from a date when the specimen was collected from the subject.

As shown in the examples described later, IFNλ3, CXCL11, IP-10, IL-6 and CXCL9 showed high values in a patient with severe respiratory infection and low values in a patient with mild respiratory infection. Measured values of IFNλ3, CXCL11, IP-10, IL-6 and CXCL9 can be used as indexes suggesting the possibility of exacerbation of respiratory infection, by comparison with threshold values corresponding to each biomarker. In one embodiment, when the biomarker contains IFNλ3 and the measured value of IFNλ3 is greater than or equal to a threshold value corresponding to IFNλ3, the possibility of exacerbation of respiratory infection of the subject is suggested to be high. When the measured value of IFNλ3 is less than the threshold value corresponding to IFNλ3, the possibility of exacerbation of respiratory infection of the subject is suggested to be low.

In one embodiment, when the biomarker contains CXCL11 and the measured value of CXCL11 is greater than or equal to a threshold value corresponding to CXCL11, the possibility of exacerbation of respiratory infection of the subject is suggested to be high. When the measured value of CXCL11 is less than the threshold value corresponding to CXCL11, the possibility of exacerbation of respiratory infection of the subject is suggested to be low.

In one embodiment, when the biomarker contains IP-10 and the measured value of IP-10 is greater than or equal to a threshold value corresponding to IP-10, the possibility of exacerbation of respiratory infection of the subject is suggested to be high. When the measured value of IP-10 is less than the threshold value corresponding to IP-10, the possibility of exacerbation of respiratory infection of the subject is suggested to be low.

In one embodiment, when the biomarker contains IL-6 and the measured value of IL-6 is greater than or equal to a threshold value corresponding to IL-6, the possibility of exacerbation of respiratory infection of the subject is suggested to be high. When the measured value of IL-6 is less than the threshold value corresponding to IL-6, the possibility of exacerbation of respiratory infection of the subject is suggested to be low.

In one embodiment, when the biomarker contains CXCL9 and the measured value of CXCL9 is greater than or equal to a threshold value corresponding to CXCL9, the possibility of exacerbation of respiratory infection of the subject is suggested to be high, and when the measured value of CXCL9 is less than the threshold value corresponding to CXCL9, the possibility of exacerbation of respiratory infection of the subject is suggested to be low.

In one embodiment, the biomarker contains at least two selected from the group consisting of IFNλ3, CXCL11, IP-10, IL-6 and CXCL9, and the exacerbation risk of the respiratory infection of the subject may be suggested by their measured values. Specifically, when at least one of the measured values of the biomarkers selected from the group is greater than or equal to a threshold value corresponding to the biomarker, the possibility of exacerbation of respiratory infection of the subject is suggested to be high. When all of the measured values of the biomarkers selected from the group are less than threshold values corresponding to each biomarker, the possibility of exacerbation of respiratory infection of the subject is suggested to be low.

As an example, when the biomarkers are two selected from the group consisting of IFNλ3, CXCL11, IP-10, IL-6 and CXCL9, and either or both of them are greater than or equal to the corresponding threshold values, the possibility of exacerbation of respiratory infection of the subject is suggested to be high. In another example, when the biomarkers are three selected from the group consisting of IFNλ3, CXCL11, IP-10, IL-6 and CXCL9, and at least one of them is greater than or equal to the corresponding threshold values, the possibility of exacerbation of respiratory infection of the subject is suggested to be high. In another example, when the biomarkers are four selected from the group consisting of IFNλ3, CXCL11, IP-10, IL-6 and CXCL9, and at least one of them is greater than or equal to the corresponding threshold values, the possibility of exacerbation of respiratory infection of the subject is suggested to be high. In another example, when the biomarkers are five consisting of IFNλ3, CXCL11, IP-10, IL-6, and CXCL9 and at least one of them is greater than or equal to the corresponding threshold values, the possibility of exacerbation of respiratory infection of the subject is suggested to be high.

In another embodiment, the biomarker contains at least two selected from the group consisting of IFNλ3, CXCL11, IP-10, IL-6 and CXCL9, and the exacerbation risk of the respiratory infection of the subject can be classified into three stages by their measured values. Specifically:
  when all of the measured values of the biomarkers selected from the group are greater than or equal to the threshold values corresponding to each biomarker, the possibility of exacerbation of respiratory infection is suggested to be high;
  when at least one of the measured values of the biomarkers selected from the group is greater than or equal to a threshold value corresponding to the biomarker, the possibility of exacerbation of respiratory infection is suggested to be medium; and
  when all of the measured values of the biomarkers selected from the group are less than the threshold values corresponding to each biomarker, the possibility of exacerbation of respiratory infection is suggested to be low.

As an example, when the biomarkers are two selected from the group consisting of IFNλ3, CXCL11, IP-10, IL-6 and CXCL9, and both of them are greater than or equal to the corresponding threshold values, the possibility of exacerbation of respiratory infection of the subject is suggested to be high. In another example, when the biomarkers are three selected from the group consisting of IFNλ3, CXCL11, IP-10, IL-6 and CXCL9, and all of them are greater than or equal to the corresponding threshold values, the possibility of exacerbation of respiratory infection of the subject is suggested to be high. In another example, when the biomarkers are four selected from the group consisting of IFNλ3, CXCL11, IP-10, IL-6 and CXCL9, and all of them are greater than or equal to the corresponding threshold values, the possibility of exacerbation of respiratory infection of the subject is suggested to be high. In another example, when the biomarkers are five consisting of IFNλ3, CXCL11, IP-10, IL-6 and CXCL9, and all of them are greater than or equal to the corresponding threshold values, the possibility of exacerbation of respiratory infection of the subject is suggested to be high.

In the present embodiment, CCL17 in the specimen may be measured. As shown in the examples described later, CCL17, unlike other biomarkers, showed a low value in a patient with severe respiratory infection and a high value in a patient with mild respiratory infection. The measured value of CCL17 can be used as an index suggesting the possibility of exacerbation of respiratory infection, by comparison with a threshold value corresponding to CCL17. In one embodiment, when the biomarker contains CCL17 and the measured value of CCL17 is less than the threshold value corresponding to CCL17, the possibility of exacerbation of respiratory infection of the subject is suggested to be high. When the measured value of CCL17 is greater than or equal to the threshold value corresponding to CCL17, the possibility of exacerbation of respiratory infection of the subject is suggested to be low.

In a preferred embodiment, CCL17 is used in combination with at least one biomarker selected from IFNλ3, CXCL11, IP-10, IL-6 and CXCL9. For example, the biomarker contains at least one selected from the group consisting of IFNλ3, CXCL11, IP-10, IL-6 and CXCL9, and CCL17, and the exacerbation risk of the respiratory infection of the subject may be suggested by their measured values. Specifically, when at least one of the measured values of the biomarkers selected from the group is greater than or equal to a threshold value corresponding to the biomarker, and/or the measured value of CCL17 is less than the threshold value corresponding to CCL17, the possibility of exacerbation of respiratory infection of the subject is suggested to be high. When all of the measured values of the biomarkers selected from the group are lower than the threshold values corresponding to each biomarker, and the measured value of CCL17 is greater than or equal to the threshold value corresponding to CCL17, the possibility of exacerbation of respiratory infection of the subject is suggested to be low.

In another embodiment, the biomarker contains at least one selected from the group consisting of IFNλ3, CXCL11, IP-10, IL-6 and CXCL9, and CCL17, and the exacerbation risk of the respiratory infection of the subject can be classified into three stages by their measured values. Specifically:

when all of the measured values of the biomarkers selected from the group are greater than or equal to the threshold values corresponding to each biomarker, and the measured value of CCL17 is less than the threshold value corresponding to CCL17, the possibility of exacerbation of respiratory infection of the subject is suggested to be high;

when at least one of the measured values of the biomarkers selected from the group is greater than or equal to the threshold value corresponding to the biomarker, and the measured value of CCL17 is greater than the threshold value corresponding to CCL17, the possibility of exacerbation of respiratory infection of the subject is suggested to be medium;

when at least one of the measured values of the biomarkers selected from the group is less than the threshold value corresponding to the biomarker, and the measured value of CCL17 is less than the threshold value corresponding to CCL17, the possibility of exacerbation of respiratory infection of the subject is suggested to be medium; and when all of the measured values of the biomarkers selected from the group are lower than the threshold values corresponding to each biomarker, and the measured value of CCL17 is greater than or equal to the threshold value corresponding to CCL17, the possibility of exacerbation of respiratory infection of the subject is suggested to be low.

In a more specific example, biomarkers contain IFNλ3 and CCL17, when the measured value of IFNλ3 is greater than or equal to the threshold value corresponding to IFNλ3, and the measured value of CCL17 is less than the threshold value corresponding to CCL17, the possibility of exacerbation of respiratory infection of the subject is suggested to be high;

when the measured value of IFNλ3 is greater than or equal to the threshold value corresponding to IFNλ3, and the measured value of CCL17 is greater than or equal to the threshold value corresponding to CCL17, the possibility of exacerbation of respiratory infection of the subject is suggested to be medium;

when the measured value of IFNλ3 is less than the threshold value corresponding to IFNλ3, and the measured value of CCL17 is less than the threshold value corresponding to CCL17, the possibility of exacerbation of respiratory infection of the subject is suggested to be medium; and when the measured value of IFNλ3 is less than the threshold value corresponding to IFNλ3, and the measured value of CCL17 is greater than or equal to the threshold value corresponding to CCL17, the possibility of exacerbation of respiratory infection of the subject is suggested to be low.

The threshold values corresponding to each biomarker are not particularly limited and can be set as appropriate. For example, specimens are collected from a plurality of patients with respiratory infection, and biomarkers in the specimens are measured to obtain measured values. After a predetermined period (for example, 2 weeks) has passed since the specimens were collected, whether or not the respiratory infection has become severe is confirmed. The acquired measured value data is classified into data of a group of severely ill patients and data of a group of non-severely ill patients. Then, for each biomarker, a value that can most accurately distinguish between the group of severely ill patients and the group of non-severely ill patients is determined, and the value is set as a threshold value. In setting the threshold value, it is possible to consider sensitivity, specificity, positive predictive value, negative predictive value, and the like.

In the present embodiment, the threshold value corresponding to IFNλ3 is set in the range of, for example, 4 pg/mL or more and 15 pg/mL or less. The threshold value corresponding to CXCL11 is set in the range of, for example, 20 pg/mL or more and 40 pg/mL or less. The threshold value corresponding to IP-10 is set in the range of, for example, 400 pg/mL or more and 1200 pg/mL or less. The threshold value corresponding to IL-6 is set in the range of, for example, 4 pg/mL or more and 6 pg/mL or less. The threshold value corresponding to CXCL9 is set in the range of, for example, 30 pg/mL or more and 40 pg/mL or less. The threshold value corresponding to CCL17 is set in the range of, for example, 40 pg/mL or more and 100 pg/mL or less.

Healthcare professionals such as doctors may combine the suggestion from the measured value of the biomarker with other information to determine the risk of exacerbation of respiratory infection. The "other information" includes findings on X-ray or CT images of the lungs and other medical findings.

As an index to predict exacerbation of the respiratory infection of the subject of the present embodiment, temporal change of the measured value of the biomarker in the subject may be acquired. The temporal change of the measured value of the biomarker is not particularly limited as long as it is information showing transition of the measured value of the biomarker in the specimen collected from the subject a plurality of times periodically or irregularly. Examples of such temporal change include values calculated from a plurality of measured values (for example, the difference, ratio, etc. of the measured values of two specimens collected at any two time points), records of the measured values (for example, a table of measured values, a graph plotting measured values, etc.), and the like.

In the present embodiment, when the possibility of exacerbation of respiratory infection of the subject was suggested to be high by the acquired measured value of the biomarker, it is possible to perform medical intervention for the exacerbation of respiratory infection on the subject. Examples of the medical intervention include drug administration, surgery, immunotherapy, gene therapy, oxygenation procedures, heart-lung machine procedures, and the like. The drug can be appropriately selected from known therapeutic drugs for respiratory infections or candidate medicines therefor. For example, when the respiratory infection is SARS-CoV-2 infection, examples of the drug include drugs having an antiviral action, drugs that reduce inflammation, ACE inhibitors, and the like. Specific examples of the drug include favipiravir, lopinavir, ritonavir, nafamostat, camostat, remdesivir, ribavirin, ivermectin, ciclesonide, chloroquine, hydroxychloroquine, interferon, tocilizumab, sarilumab, tofasitinib, baricitinib, ruxolitinib, acalabrutinib, ravulizumab, eritoran, ibudilast, HLCM051, LY3127804, and the like.

The prediction method of the present embodiment may include predicting exacerbation of respiratory infection, based on the measured value of the biomarker acquired from the specimen collected from the subject. In the predicting, for example, the acquired measured value of the biomarker is compared with a threshold value corresponding to the biomarker, and based on the comparison result, whether the possibility of exacerbation of respiratory infection of the subject is high or low may be determined. Details of the threshold value corresponding to the biomarker are as described above.

In one embodiment, when the biomarker contains IFNλ3 and the measured value of IFNλ3 is greater than or equal to the threshold value corresponding to IFNλ3, the possibility of exacerbation of respiratory infection of the subject can be determined to be high. When the measured value of IFNλ3 is less than the threshold value corresponding to IFNλ3, the possibility of exacerbation of respiratory infection of the subject can be determined to be low.

In one embodiment, when the biomarker contains CXCL11 and the measured value of CXCL11 is greater than or equal to the threshold value corresponding to CXCL11, the possibility of exacerbation of respiratory infection of the subject can be determined to be high. When the measured value of CXCL11 is less than the threshold value corresponding to CXCL11, the possibility of exacerbation of respiratory infection of the subject can be determined to be low.

In one embodiment, when the biomarker contains IP-10 and the measured value of IP-10 is greater than or equal to the threshold value corresponding to IP-10, the possibility of exacerbation of respiratory infection of the subject can be determined to be high. When the measured value of IP-10 is less than the threshold value corresponding to IP-10, the possibility of exacerbation of respiratory infection of the subject can be determined to be low.

In one embodiment, when the biomarker contains IL-6 and the measured value of IL-6 is greater than or equal to the threshold value corresponding to IL-6, the possibility of exacerbation of respiratory infection of the subject can be determined to be high. When the measured value of IL-6 is less than the threshold value corresponding to IL-6, the possibility of exacerbation of respiratory infection of the subject can be determined to be low.

In one embodiment, when the biomarker contains CXCL9 and the measured value of CXCL9 is greater than or equal to the threshold value corresponding to CXCL9, the possibility of exacerbation of respiratory infection of the subject can be determined to be high. When the measured value of CXCL9 is less than the threshold value corresponding to CXCL9, the possibility of exacerbation of respiratory infection of the subject can be determined to be low.

In one embodiment, when the biomarker contains CCL17 and the measured value of CCL17 is less than the threshold value corresponding to CCL17, the possibility of exacerbation of respiratory infection of the subject can be determined to be high. When the measured value of CCL17 is greater than or equal to the threshold value corresponding to CCL17, the possibility of exacerbation of respiratory infection of the subject can be determined to be low.

In one embodiment, the biomarker contains at least two selected from the group consisting of IFNλ3, CXCL11, IP-10, IL-6 and CXCL9, and the exacerbation risk of the respiratory infection of the subject may be determined based on their measured values. Specifically, when at least one of the measured values of the biomarkers selected from the group is greater than or equal to a threshold value corresponding to the biomarker, the possibility of exacerbation of respiratory infection of the subject can be determined to be high. When all of the measured values of the biomarkers selected from the group are less than the threshold values corresponding to each biomarker, the possibility of exacerbation of respiratory infection of the subject can be determined to be low.

As an example, when the biomarkers are two selected from the group consisting of IFNλ3, CXCL11, IP-10, IL-6 and CXCL9, and either or both of them are greater than or equal to the corresponding threshold values, the possibility of exacerbation of respiratory infection of the subject can be determined to be high. In another example, when the biomarkers are three selected from the group consisting of IFNλ3, CXCL11, IP-10, IL-6 and CXCL9, and at least one of them is greater than or equal to the corresponding threshold values, the possibility of exacerbation of respiratory infection of the subject can be determined to be high. In another example, when the biomarkers are four selected from the group consisting of IFNλ3, CXCL11, IP-10, IL-6 and CXCL9, and at least one of them is greater than or equal to the corresponding threshold values, the possibility of exacerbation of respiratory infection of the subject can be determined to be high. In another example, when the biomarkers are five consisting of IFNλ3, CXCL11, IP-10, IL-6 and CXCL9, and at least one of them is greater than or equal to the corresponding threshold values, the possibility of exacerbation of respiratory infection of the subject can be determined to be high.

In another embodiment, the biomarker contains at least two selected from the group consisting of IFNλ3, CXCL11, IP-10, IL-6 and CXCL9, and the exacerbation risk of the respiratory infection of the subject may be determined in three stages based on their measured values. Specifically:

when all of the measured values of the biomarkers selected from the group are greater than or equal to the threshold values corresponding to each biomarker, the possibility of exacerbation of respiratory infection is determined to be high;

when at least one of the measured values of the biomarkers selected from the group is greater than or equal to the threshold value corresponding to the biomarker, the possibility of exacerbation of respiratory infection is determined to be medium; and when all of the measured values of the biomarkers selected from the group are less than the threshold values corresponding to each biomarker, the possibility of exacerbation of respiratory infection can be determined to be low.

As an example, when the biomarkers are two selected from the group consisting of IFNλ3, CXCL11, IP-10, IL-6 and CXCL9, and both of them are greater than or equal to the corresponding threshold values, the possibility of exacerbation of respiratory infection of the subject is determined to be high. In another example, when the biomarkers are three selected from the group consisting of IFNλ3, CXCL11, IP-10, IL-6 and CXCL9, and all of them are greater than or equal to the corresponding threshold values, the possibility of exacerbation of respiratory infection of the subject is determined to be high. In another example, when the biomarkers are four selected from the group consisting of IFNλ3, CXCL11, IP-10, IL-6 and CXCL9, and all of them are greater than or equal to the corresponding threshold values, the possibility of exacerbation of respiratory infection of the subject is determined to be high. In another example, when the biomarkers are five consisting of IFNλ3, CXCL11, IP-10, IL-6 and CXCL9, and all of them are greater than or equal to the corresponding threshold values, the possibility of exacerbation of respiratory infection of the subject is determined to be high.

In a further embodiment, the biomarker contains at least one selected from the group consisting of IFNλ3, CXCL11, IP-10, IL-6 and CXCL9, and CCL17, and the exacerbation risk of the respiratory infection of the subject may be determined based on their measured values. Specifically, when at least one of the measured values of the biomarkers selected from the group is greater than or equal to a threshold value corresponding to the biomarker, and/or the measured value of CCL17 is less than the threshold value corresponding to CCL17, the possibility of exacerbation of respiratory infection of the subject can be determined to be high. When all of the measured values of the biomarkers selected from the group are lower than the threshold values corresponding to each biomarker, and the measured value of CCL17 is greater than or equal to the threshold value corresponding to CCL17, the possibility of exacerbation of respiratory infection of the subject can be determined to be low.

In another embodiment, the biomarker contains at least one selected from the group consisting of IFNλ3, CXCL11, IP-10, IL-6 and CXCL9, and CCL17, and the exacerbation risk of the respiratory infection of the subject may be determined in three stages based on their measured values. Specifically:

when all of the measured values of the biomarkers selected from the group are greater than or equal to the threshold values corresponding to each biomarker, and the measured value of CCL17 is less than the threshold value corresponding to CCL17, the possibility of exacerbation of respiratory infection of the subject is determined to be high;

when at least one of the measured values of the biomarkers selected from the group is greater than or equal to a threshold value corresponding to the biomarker, and the measured value of CCL17 is greater than or equal to the threshold value corresponding to CCL17, the possibility of exacerbation of respiratory infection of the subject is determined to be medium;

when at least one of the measured values of the biomarkers selected from the group is less than the threshold value corresponding to the biomarker and the measured value of CCL17 is less than the threshold value corresponding to CCL17, the possibility of exacerbation of respiratory infection of the subject is determined to be medium; and when all of the measured values of the biomarkers selected from the group are lower than the threshold values corresponding to each biomarker, and the measured value of CCL17 is greater than or equal to the threshold value corresponding to CCL17, the possibility of exacerbation of respiratory infection of the subject can be determined to be low.

In a more specific example, biomarkers contain IFNλ3 and CCL17, when the measured value of IFNλ3 is greater than or equal to the threshold value corresponding to IFNλ3, and the measured value of CCL17 is less than the threshold value corresponding to CCL17, the possibility of exacerbation of respiratory infection of the subject is determined to be high;

when the measured value of IFNλ3 is greater than or equal to the threshold value corresponding to IFNλ3, and the measured value of CCL17 is greater than or equal to the threshold value corresponding to CCL17, the possibility of exacerbation of respiratory infection of the subject is determined to be medium;

when the measured value of IFNλ3 is less than the threshold value corresponding to IFNλ3, and the measured value of CCL17 is less than the threshold value corresponding to CCL17, the possibility of exacerbation of respiratory infection of the subject is determined to be medium; and when the measured value of IFNλ3 is lower than the threshold value corresponding to IFNλ3, and the measured value of CCL17 is greater than or equal to the threshold value corresponding to CCL17, the possibility of exacerbation of respiratory infection of the subject can be determined to be low.

One embodiment is a method for monitoring a measured value of a biomarker in a specimen collected from a subject (hereinafter, also referred to as "monitoring method"). In the monitoring method of the present embodiment, the measured value of the biomarker is acquired using specimens collected from the subject at a plurality of time points. Details of the subject, the specimen, the biomarker and acquisition of the measured value thereof are the same as those described for the prediction method of the present embodiment described above.

In the present embodiment, the plurality of time points may be two or more different time points. For example, the plurality of time points includes a first time point and a second time point different from the first time point. The first time point is not particularly limited and can be any time point. For example, the first time point may be a time point when the subject is found to have a respiratory infection, a time point when the subject develops symptoms of a respiratory infection, a time point when the subject is hospitalized, or the like The second time point is not particularly limited as long as it differs from the first time point. Preferably, the second time point is a time point when a period within one month has passed from the first time point. Specifically, the second time point is a time point when 0.5 hours, 1 hour, 2 hours, 3 hours, 4 hours, 5 hours, 6 hours, 7 hours, 8 hours, 9 hours, 10 hours, 12 hours, 15 hours, 18 hours, 1 day, 2 days, 3 days, 4 days, 5 days, 6 days, 7 days, 8 days, 9 days, 10 days, 12 days, 2 weeks, 3 weeks, 4 weeks or one month has passed from the first time point.

In the present embodiment, the "specimens collected from the subject at a plurality of time points" are specimens collected from the same subject at each of the plurality of time points. For example, it includes a first specimen collected from a subject at a first time point and a second specimen collected from the subject at a second time point different from the first time point. In the monitoring method of the present embodiment, the biomarker may be measured each time a specimen is collected, or each collected specimen may be stored and measured collectively.

In the monitoring method of the present embodiment, the measured value of the biomarker in the same subject is monitored and used as an index to predict exacerbation of the respiratory infection. In a preferred embodiment, the measured values of the same biomarker at a plurality of time points are acquired. The measured value of the biomarker measured from each specimen is compared with the threshold value corresponding to the biomarker, and based on the comparison result, the possibility of exacerbation of respiratory infection of the subject may be suggested to be high or low. Details of the threshold value corresponding to the biomarker are similar to those described for the prediction method of the present embodiment.

In one embodiment, when the biomarker contains IFNλ3 and the measured value of IFNλ3 is greater than or equal to the threshold value corresponding to IFNλ3 at least one of the plurality of time points, the possibility of exacerbation of respiratory infection of the subject is suggested to be high. When the measured value of IFNλ3 is less than the threshold value corresponding to IFNλ3 at any of the plurality of time points, the possibility of exacerbation of respiratory infection of the subject is suggested to be low.

In one embodiment, when the biomarker contains CXCL11 and the measured value of CXCL11 is greater than or equal to the threshold value corresponding to CXCL11 at at least one of the plurality of time points, the possibility of exacerbation of respiratory infection of the subject is suggested to be high. When the measured value of CXCL11 is less than the threshold value corresponding to CXCL11 at any of the plurality of time points, the possibility of exacerbation of respiratory infection of the subject is suggested to be low.

In one embodiment, when the biomarker contains IP-10 and the measured value of IP-10 is greater than or equal to the threshold value corresponding to IP-10 at at least one of the plurality of time points, the possibility of exacerbation of respiratory infection of the subject is suggested to be high. When the measured value of IP-10 is less than the threshold value corresponding to IP-10 at any of the plurality of time points, the possibility of exacerbation of respiratory infection of the subject is suggested to be low.

In one embodiment, when the biomarker contains IL-6 and the measured value of IL-6 is greater than or equal to the threshold value corresponding to IL-6 at at least one of the plurality of time points, the possibility of exacerbation of respiratory infection of the subject is suggested to be high. When the measured value of IL-6 is less than the threshold value corresponding to IL-6 at any of the plurality of time points, the possibility of exacerbation of respiratory infection of the subject is suggested to be low.

In one embodiment, when the biomarker contains CXCL9 and the measured value of CXCL9 is greater than or equal to the threshold value corresponding to CXCL9 at at least one of the plurality of time points, the possibility of exacerbation of respiratory infection of the subject is suggested to be high. When the measured value of CXCL9 is less than the threshold value corresponding to CXCL9 at any of the plurality of time points, the possibility of exacerbation of respiratory infection of the subject is suggested to be low.

In one embodiment, the biomarker contains at least two selected from the group consisting of IFNλ3, CXCL11, IP-10, IL-6 and CXCL9, and the exacerbation risk of the respiratory infection of the subject may be suggested by the measured values of the biomarkers at a plurality of time points. Specifically, when at least one of the measured values of the biomarkers selected from the group is greater than or equal to a threshold value corresponding to the biomarker at at least one of the plurality of time points, the possibility of exacerbation of respiratory infection of the subject is suggested to be high. When all of the measured values of the biomarkers selected from the group are less than the threshold values corresponding to each biomarker at any of the plurality of time points, the possibility of exacerbation of respiratory infection of the subject is suggested to be low.

The measured value of CCL17 in each of the specimens may be acquired. In one embodiment, when the biomarker contains CCL17 and the measured value of CCL17 is less than the threshold value corresponding to CCL17 at at least one of the plurality of time points, the possibility of exacerbation of respiratory infection of the subject is suggested to be high. When the measured value of CCL17 is greater than or equal to the threshold value corresponding to CCL17 at any of the plurality of time points, the possibility of exacerbation of respiratory infection of the subject is suggested to be low.

In a further embodiment, the biomarker contains at least one selected from the group consisting of IFNλ3, CXCL11, IP-10, IL-6 and CXCL9, and CCL17, and the exacerbation risk of the respiratory infection of the subject may be suggested by the measured values of the biomarkers at a plurality of time points. Specifically, when at least one of the measured values of the biomarkers selected from the group is greater than or equal to a threshold value corresponding to the biomarker at at least one of the plurality of time points, and/or the measured value of CCL17 is less than the threshold value corresponding to CCL17 at at least one of the plurality of time points, the possibility of exacerbation of respiratory infection of the subject is suggested to be high. When all of the measured values of the biomarkers selected from the group are lower than the threshold values corresponding to each biomarker at any of the plurality of time points, and the measured value of CCL17 is greater than or equal to the threshold value corresponding to CCL17 at any of the plurality of time points, the possibility of exacerbation of respiratory infection of the subject is suggested to be low.

The conditions for terminating the monitoring method of the present embodiment are not particularly limited, and a healthcare professional such as a doctor may appropriately determine the conditions. For example, when the possibility of exacerbation of respiratory infection of the subject was suggested to be high by the measured values of the biomarkers acquired from specimens collected from the subject at a plurality of time points, the monitoring method of the present embodiment may be terminated. In this case, it is preferable to perform medical intervention for the exacerbation of respiratory infection on the subject. Details of the medical intervention are as described above. Alternatively, when the possibility of exacerbation of respiratory infection of the subject was suggested to be low by the measured values of the biomarkers acquired from specimens collected from the subject at a plurality of time points, and any symptoms of respiratory infection is not recognized on the subject, the monitoring method of the present embodiment may be terminated.

In each of the embodiments described above, when the measured values of IFNλ3, CXCL11, IP-10, IL-6 and CXCL9 are the same as the threshold values corresponding to each biomarker, it has been stated that the possibility of exacerbation of respiratory infection of the subject is suggested to be high. However, the possibility of exacerbation of respiratory infection of the subject may be suggested to be low. In each of the embodiments described above, when the measured value of CCL17 is the same as the threshold value corresponding to CCL17, it has been stated that the possibility of exacerbation of respiratory infection of the subject is suggested to be low. However, the possibility of exacerbation of respiratory infection of the subject may be suggested to be high.

One embodiment is a reagent kit for use in the prediction method and/or monitoring method of the present embodiment described above. The reagent kit of the present embodiment includes at least one reagent selected from a reagent containing a substance capable of specifically binding to IFNλ3, a reagent containing a substance capable of specifically binding to CCL17, a reagent containing a substance capable of specifically binding to CXCL11, a reagent containing a substance capable of specifically binding to IP-10, a reagent containing a substance capable of specifically binding to IL-6, and a reagent containing a substance capable of specifically binding to CXCL9. In a further embodiment, the reagent kit may include at least one reagent selected from the reagent containing a substance capable of specifically binding to IFNλ3, the reagent containing a substance capable of specifically binding to CXCL11, the reagent containing a substance capable of specifically binding to IP-10, the reagent containing a substance capable of specifically binding to IL-6, and the reagent containing a substance capable of specifically binding to CXCL9, and the reagent containing a substance capable of specifically binding to CCL17. In a preferred embodiment, the reagent kit includes the reagent containing a substance capable of specifically binding to IFNλ3 and the reagent containing a substance capable of specifically binding to CCL17. Examples of the substance capable of specifically binding to each biomarker include an antibody, an aptamer, and the like. The antibody is particularly preferable among them.

FIG. 1A shows an example of the reagent kit of the present embodiment. In FIG. 1A, 11 denotes a reagent kit, 12 denotes a first container containing a reagent containing a substance capable of specifically binding to IFNλ3, 13 denotes a second container containing a reagent containing a substance capable of specifically binding to CCL17, 14 denotes a packing box, and 15 denotes an attached document. Composition, usage, storage method, etc. of each reagent may be described in the attached document. The reagent kit of this example includes the reagent containing a substance capable of specifically binding to IFNλ3 and the reagent containing a substance capable of specifically binding to CCL17, but in place of these reagents, reagents containing a substance capable of specifically binding to another biomarker may be included.

In a preferred embodiment, the reagent kit of the present embodiment includes a capture antibody and a detection antibody for the biomarker. The detection antibody may be labeled with a labeling substance. Details of the capture antibody, the detection antibody and the labeling substance are the same as those described for the prediction method of the present embodiment. The reagent kit may include a solid phase and a substrate. Details of the solid phase and the substrate are the same as those described for the prediction method of the present embodiment.

Figure 1B:
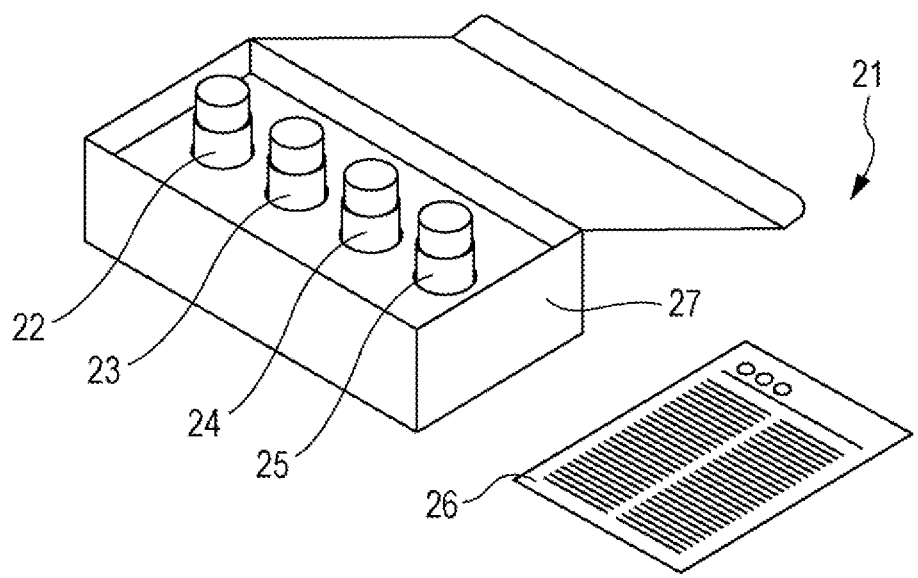
FIG. 1B is a schematic diagram showing an example of the reagent kit of the present embodiment.

FIG. 1B shows an example of a reagent kit of a further embodiment. In FIG. 1B, 21 denotes a reagent kit, 22 denotes a first container containing a reagent containing a capture antibody for IFNλ3, 23 denotes a second container containing a reagent containing a detection labeled antibody for IFNλ3, 24 denotes a third container containing a reagent containing a capture antibody for CCL17, 25 denotes a fourth container containing a reagent containing a detection labeled antibody for CCL17, 26 denotes an attached document, and 27 denotes a packing box. The reagent kit of this example includes reagents each containing the capture antibody and the detection labeled antibody for IFNλ3 and reagents each containing the capture antibody and the detection labeled antibody for CCL17, but in place of these reagents, reagents each containing a capture antibody for another biomarker and a detection labeled antibody for another biomarker may be included.

It is preferable that any of the above reagent kits include a calibrator. Examples of the calibrator include a calibrator for quantifying IFNλ3 (calibrator for IFNλ3), a calibrator for quantifying CXCL11 (calibrator for CXCL11), a calibrator for quantifying IP-10 (calibrator for IP-10), a calibrator for quantifying IL-6 (calibrator for IL-6), a calibrator for quantifying CXCL9 (calibrator for CXCL9), and a calibrator for quantifying CCL17 (calibrator for CCL17). The calibrator for IFNλ3 may include, for example, a buffer solution containing no IFNλ3 (negative control) and a buffer solution containing IFNλ3 at a known concentration. The calibrator for CXCL11 may include, for example, a buffer solution containing no CXCL11 (negative control) and a buffer solution containing CXCL11 at a known concentration. The calibrator for IP-10 may include, for example, a buffer solution containing no IP-10 (negative control) and a buffer solution containing IP-10 at a known concentration. The calibrator for IL-6 may include, for example, a buffer solution containing no IL-6 (negative control) and a buffer solution containing IL-6 at a known concentration. The calibrator for CXCL9 may include, for example, a buffer solution containing no CXCL9 (negative control) and a buffer solution containing CXCL9 at a known concentration. The calibrator for CCL17 may include, for example, a buffer solution containing no CCL17 (negative control) and a buffer solution containing CCL17 at a known concentration.

Figure 1C:
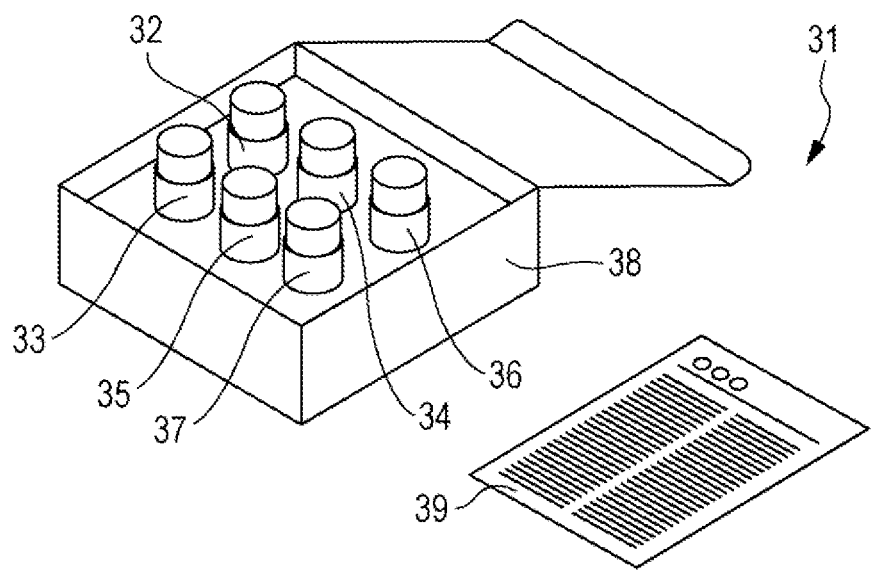
FIG. 1C is a schematic diagram showing an example of the reagent kit of the present embodiment.

FIG. 1C shows an example of a reagent kit of a further embodiment. In FIG. 1C, 31 denotes a reagent kit, 32 denotes a first container containing a reagent containing a capture antibody for IFNλ3, 33 denotes a second container containing a reagent containing a detection labeled antibody for IFNλ3, 34 denotes a third container containing a reagent containing a capture antibody for CCL17, 35 denotes a fourth container containing a reagent containing a detection labeled antibody for CCL17, 36 denotes a fifth container containing a buffer solution containing neither IFNλ3 nor CCL17, 37 denotes a sixth container containing a buffer solution containing IFNλ3 and CCL17 at each predetermined concentrations, 38 denotes a packing box, and 39 denotes an attached document. A buffer solution containing neither IFNλ3 nor CCL17 and a buffer solution containing IFNλ3 and CCL17 at each predetermined concentration can be used as a calibrator for quantifying IFNλ3 and CCL17. The reagent kit of this example includes reagents each containing the capture antibody and the detection labeled antibody for IFNλ3, reagents each containing the capture antibody and the detection labeled antibody for CCL17 and a calibrator for quantifying IFNλ3 and CCL17, but in place of these reagents, reagents each containing a capture antibody for another biomarker and a detection labeled antibody for another biomarker and a calibrator may be included.

Figure 1D:
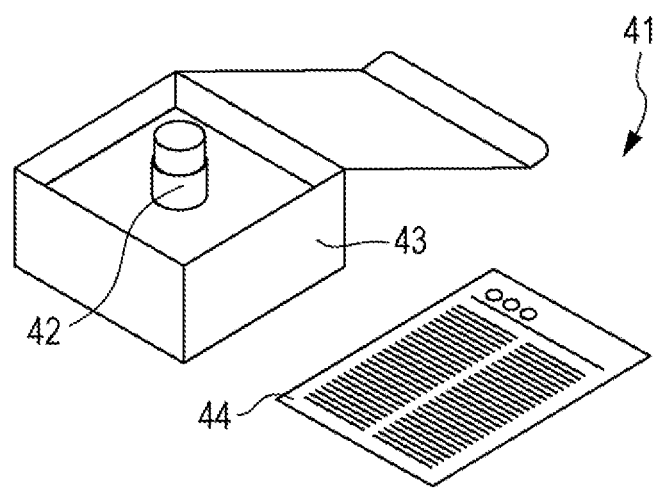
FIG. 1D is a schematic diagram showing an example of the reagent kit of the present embodiment.

In a further embodiment, a container containing one reagent selected from the reagent containing a substance capable of specifically binding to IFNλ3, the reagent containing a substance capable of specifically binding to CCL17, the reagent containing a substance capable of specifically binding to CXCL11, the reagent containing a substance capable of specifically binding to IP-10, the reagent containing a substance capable of specifically binding to IL-6, and the reagent containing a substance capable of specifically binding to CXCL9 may be packed in a box and provided to a user as a reagent kit. The box may contain an attached document. Compositions, usage, storage method, etc. of the reagents may be described in the attached document. FIG. 1D shows an example of the reagent kit. In FIG. 1D, 41 denotes a reagent kit, 42 denotes a container containing a reagent containing a substance capable of specifically binding to IFNλ3, 43 denotes a packing box, and 44 denotes an attached document. The reagent kit of this example includes the reagent containing a substance capable of specifically binding to IFNλ3, but in place of this reagent, reagents containing a substance capable of specifically binding to another biomarker may be included.

One embodiment is a device for performing the prediction method and/or monitoring method of the present embodiment. Such a device is a device to assist in predicting exacerbation of respiratory infection (hereinafter, also simply referred to as "device"). Another embodiment is a computer program for making a computer execute the prediction method and/or monitoring method of the present embodiment. Such a computer program is a computer program to assist in predicting exacerbation of respiratory infection.

Figure 2:
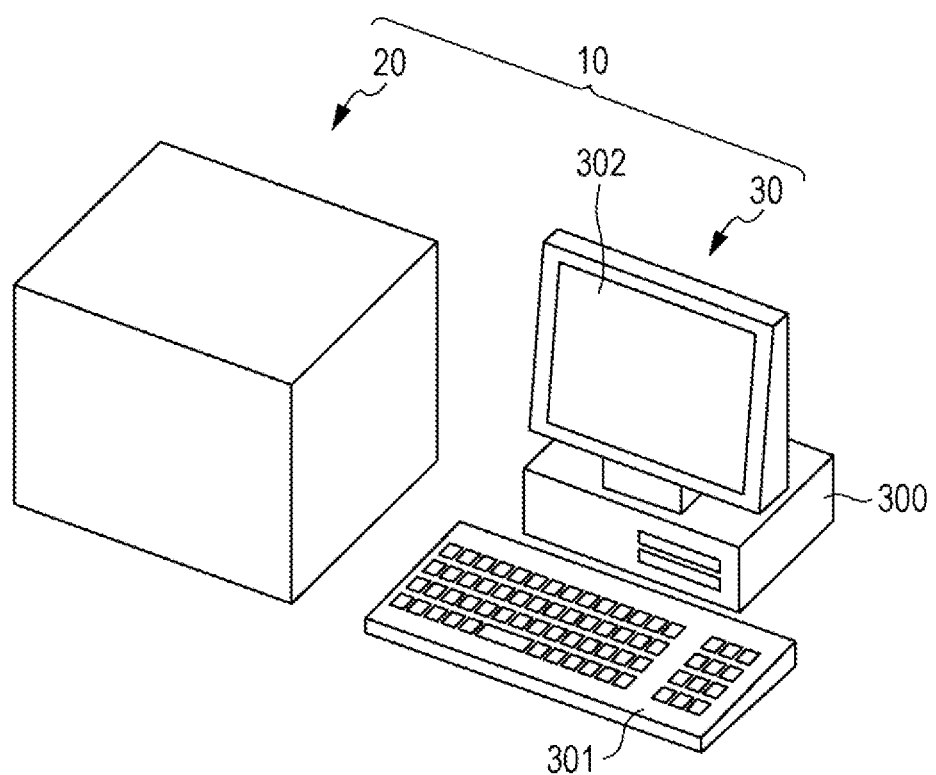
FIG. 2 is a schematic diagram showing an example of the device of the present embodiment.

Hereinbelow, an example of the device for performing the prediction method of the present embodiment will be described with reference to drawings. FIG. 2 is a schematic diagram of a device of the present embodiment. A device 10 shown in FIG. 2 includes an immunoassay device 20 and a computer system 30 connected to the immunoassay device 20.

In the present embodiment, the type of immunoassay device is not particularly limited, and it can be appropriately selected according to the method for measuring a biomarker. In the example shown in FIG. 2, the immunoassay device 20 is a commercially available automated immunoassay device capable of detecting a chemiluminescent signal generated by a sandwich ELISA method using magnetic particles on which a capture antibody is immobilized and an enzyme-labeled detection antibody. The immunoassay device 20 is not particularly limited as long as it can detect a signal based on the used labeling substance, and it can be appropriately selected according to the type of the labeling substance.

When a reagent containing magnetic particles on which a capture antibody is immobilized, a reagent containing an enzyme-labeled detection antibody and a specimen collected from a subject are set in the immunoassay device 20, the immunoassay device 20 performs an antigen-antibody reaction using each reagent, acquires a chemiluminescent signal as optical information based on the enzyme-labeled antibody specifically bound to a biomarker, and transmits the obtained optical information to the computer system 30.

The computer system 30 includes a computer main body 300, an input unit 301, and a display unit 302 that displays specimen information, a determination result, and the like. The computer system 30 receives the optical information from the immunoassay device 20. Then, a processor of the computer system 30 executes a computer program to assist in predicting exacerbation of respiratory infection, installed in a hard disk 313, based on the optical information. As shown in FIG. 2, the computer system 30 may be equipment separate from the immunoassay device 20, or may be equipment including the immunoassay device 20. In the latter case, the computer system 30 may itself be the prediction assisting device 10. A commercially available automated immunoassay device may be loaded with the computer program to assist in predicting exacerbation of respiratory infection. The device 10 may be a device in which the immunoassay device 20 and the computer system 30 are integrally configured.

Figure 3:
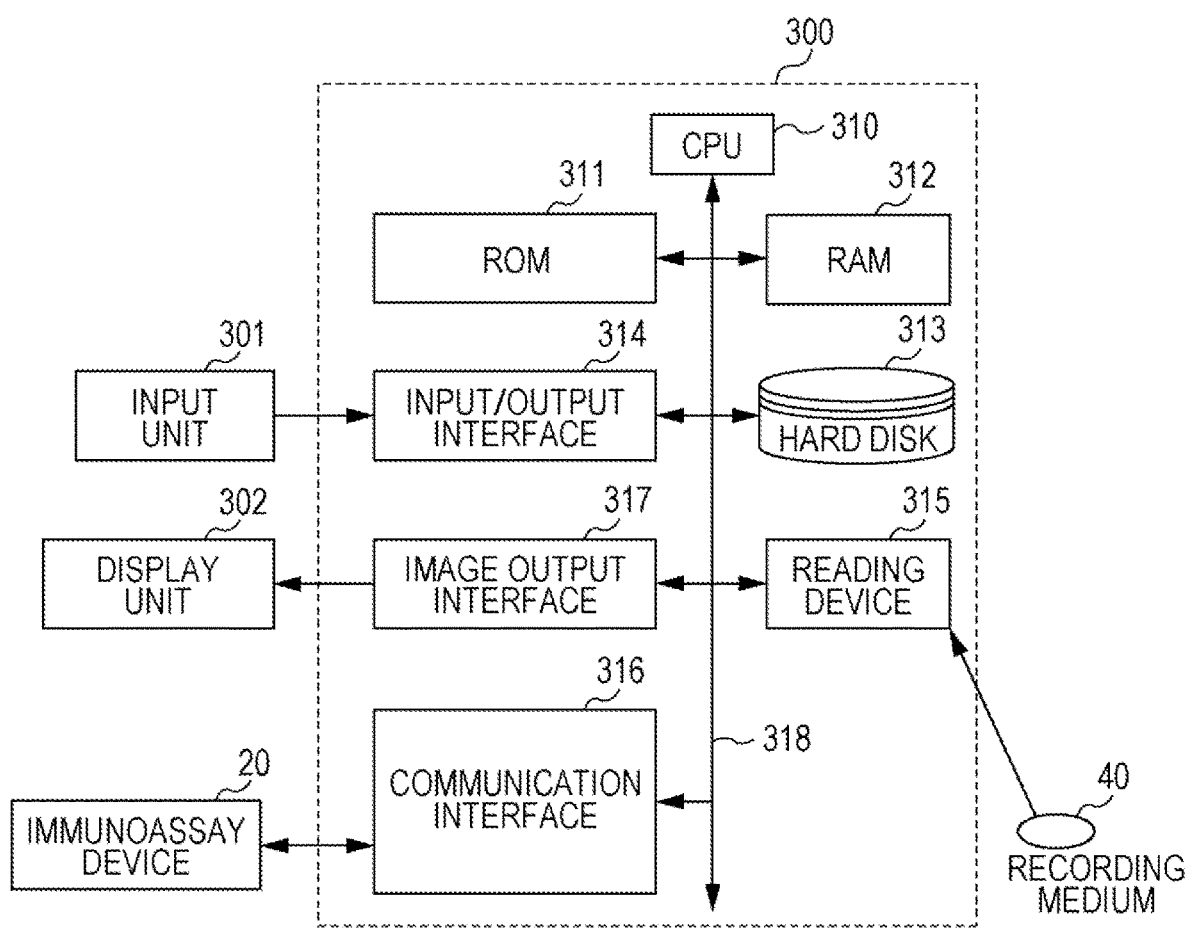
FIG. 3 is a block diagram showing a hardware configuration of the device of the present embodiment.

With reference to FIG. 3, the computer main body 300 includes a central processing unit (CPU) 310, a read only memory (ROM) 311, a random access memory (RAM) 312, a hard disk 313, an input/output interface 314, a reading device 315, a communication interface 316, and an image output interface 317. The CPU 310, the ROM 311, the RAM 312, the hard disk 313, the input/output interface 314, the reading device 315, the communication interface 316 and the image output interface 317 are data-communicably connected by a bus 318. The immunoassay device 20 is communicably connected to the computer system 30 via the communication interface 316.

The CPU 310 can execute a program stored in the ROM 311 or the hard disk 313 and a program loaded in the RAM 312. The CPU 310 calculates the measured value of the biomarker and displays it on the display unit 302.

The ROM 311 includes a mask ROM, PROM, EPROM, EEPROM, and the like. In the ROM 311, a computer program executed by the CPU 310 and data used for executing the computer program are recorded as described above. The computer program recorded in ROM 311 includes a basic input output system (BIOS).

The RAM 312 includes SRAM, DRAM, and the like. The RAM 312 is used for reading the program recorded in the ROM 311 and the hard disk 313. The RAM 312 is also used as a work area of the CPU 310 when these programs are executed.

In the hard disk 313, an operating system and a computer program such as an application program to be executed by the CPU 310, and data used for executing the computer program are installed.

The reading device 315 includes a flexible disk drive, a CD-ROM drive, a DVD-ROM drive, a USB port, an SD card reader, a CF card reader, a memory stick reader, a solid state drive, and the like. The reading device 315 can read a program or data recorded on a portable recording medium 40.

The input/output interface 314 includes, for example, a serial interface such as USB, IEEE1394 and RS-232C, a parallel interface such as SCSI, IDE and IEEE1284, and an analog interface including a D/A converter, an A/D converter and the like. The input unit 301 such as a keyboard and a mouse is connected to the input/output interface 314. An operator can input various commands to the computer main body 300 through the input unit 301.

The communication interface 316 is, for example, an Ethernet (registered trademark) interface or the like. The computer main body 300 can also transmit print data to a printer or the like through the communication interface 316.

The image output interface 317 is connected to the display unit 302 including an LCD, a CRT, and the like. As a result, the display unit 302 can output a video signal corresponding to the image data coming from the CPU 310. The display unit 302 displays an image (screen) according to the input video signal.

Figure 4A:
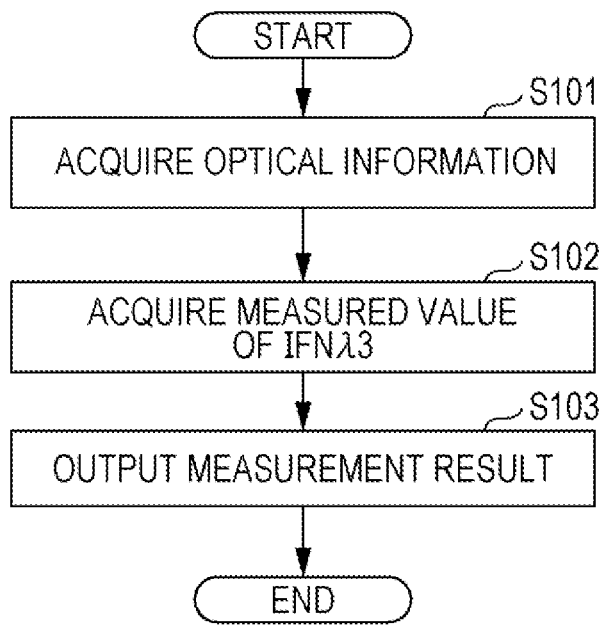
FIG. 4A is a flowchart showing a processing procedure by the device of the present embodiment.

A processing procedure to be executed by the device 10 of the present embodiment will be described with reference to FIG. 4A. Here, it will be described as an example a case where a measured value of IFNλ3 is acquired from a chemiluminescent signal generated by a sandwich ELISA method using magnetic particles on which a capture antibody is immobilized, and an enzyme-labeled detection antibody and output. In place of the measured value of IFNλ3, a measured value of CCL17, CXCL11, IP-10, IL-6 or CXCL9 may be acquired.

In step S101, the CPU 310 acquires optical information (chemiluminescent signal) from the immunoassay device 20. In step S102, the CPU 310 calculates a measured value of IFNλ3 from the acquired optical information, and the CPU 310 stores the measured value of IFNλ3 in the hard disk 313. In step S103, the CPU 310 outputs the measured value of IFNλ3, and the CPU 310 displays the determination result on the display unit 302 or makes a printer to print the measured value. When outputting the measured value of IFNλ3, a threshold value corresponding to INFλ3 may also be displayed on the display unit 302 as reference information. As a result, it is possible to provide a doctor or the like with an index to assist in predicting exacerbation of respiratory infection.

Figure 4B:
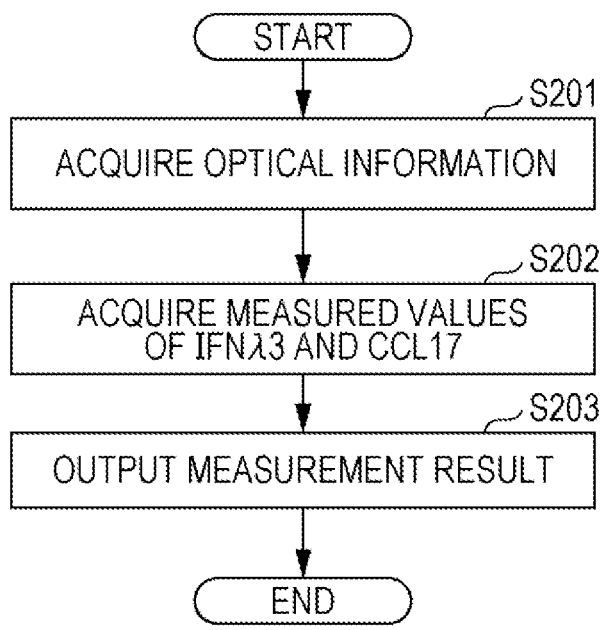
FIG. 4B is a flowchart showing a processing procedure by the device of the present embodiment.

Other processing procedures to be executed by the device 10 of the present embodiment will be described with reference to FIG. 4B. Here, a case where the measured values of IFNλ3 and CCL17 are acquired and output will be described as an example. In step S201, the CPU 310 acquires optical information (chemiluminescent signal) from the immunoassay device 20. In step S202, the CPU 310 calculates measured values of IFNλ3 and CCL17 from the acquired optical information, and the CPU 310 stores the measured values of IFNλ3 and CCL17 in the hard disk 313. In step S203, the CPU 310 outputs the determination result, and the CPU 310 displays the determination result on the display unit 302 or makes a printer to print the measured values. When outputting the measured values of IFNλ3 and CCL17, threshold values corresponding to each of IFNλ3 and CCL17 may also be displayed on the display unit 302 as reference information. As a result, it is possible to provide a doctor or the like with an index to assist in predicting exacerbation of respiratory infection.

Figure 4C:
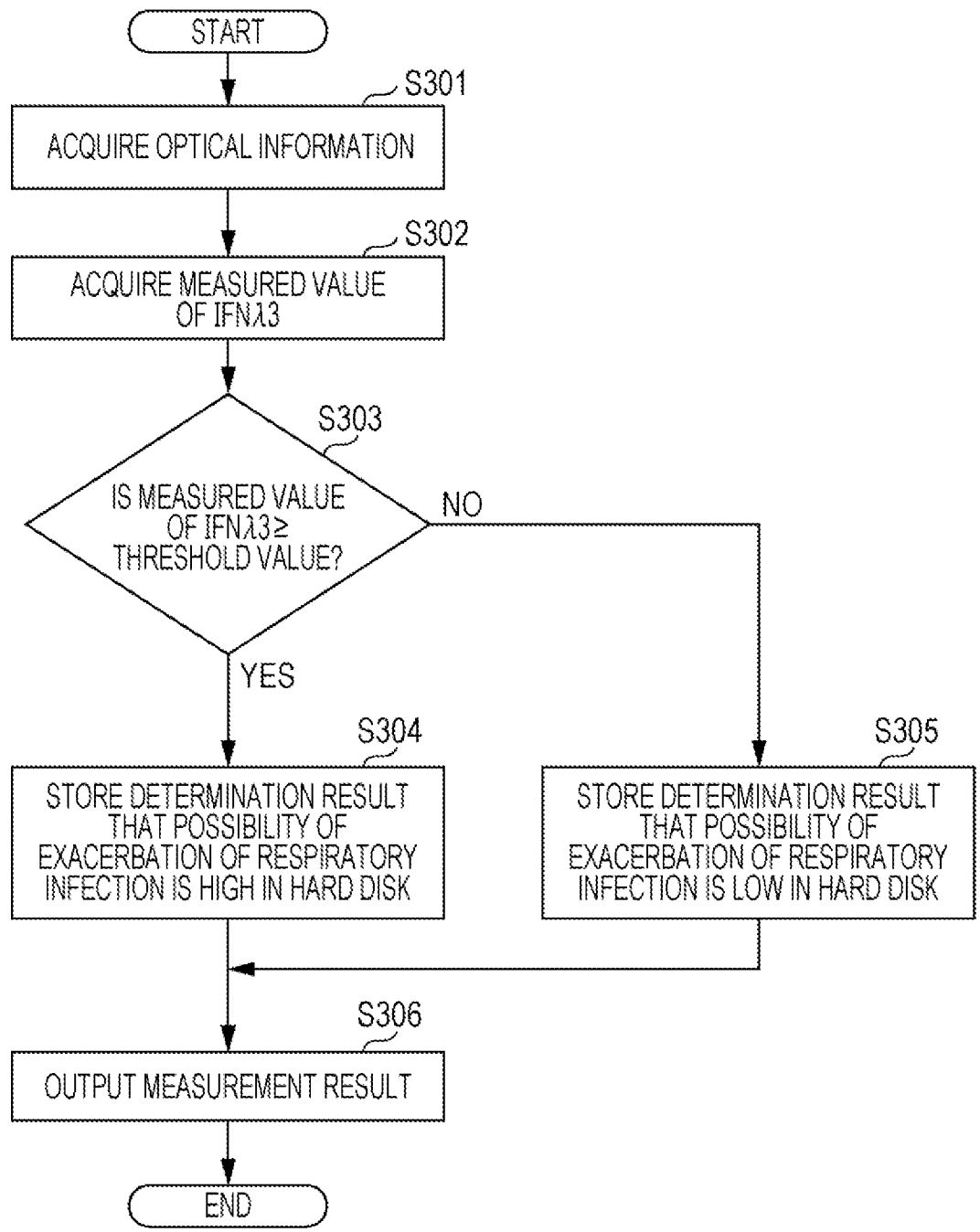
FIG. 4C is a flowchart showing a processing procedure by the device of the present embodiment.

A flow for predicting exacerbation of respiratory infection based on the measured value of IFNλ3 will be described with reference to FIG. 4C. In step S301, the CPU 310 acquires optical information (chemiluminescent signal) from the immunoassay device 20. In step S302, the CPU 310 calculates a measured value of IFNλ3 from the acquired optical information, and the CPU 310 stores the measured value of IFNλ3 in the hard disk 313. In step S303, the CPU 310 compares the calculated measured value of IFNλ3 with a threshold value corresponding to IFNλ3 stored in the hard disk 313. When the measured value of IFNλ3 is greater than or equal to the threshold value, the process proceeds to step S304. In step S304, the CPU 310 stores in the hard disk 313 a determination result that the possibility of exacerbation of respiratory infection of the subject is high.

On the other hand, in step S303, when the measured value of IFNλ3 is less than the threshold value, the process proceeds to step S305. In step S305, the CPU 310 stores in the hard disk 313 a determination result that the possibility of exacerbation of respiratory infection of the subject is low. In step S306, the CPU 310 outputs the determination result, and the CPU 310 displays the determination result on the display unit 302 or makes a printer to print the determination result. As a result, it is possible to provide a doctor or the like with an index to assist in predicting exacerbation of respiratory infection.

Figure 4D:
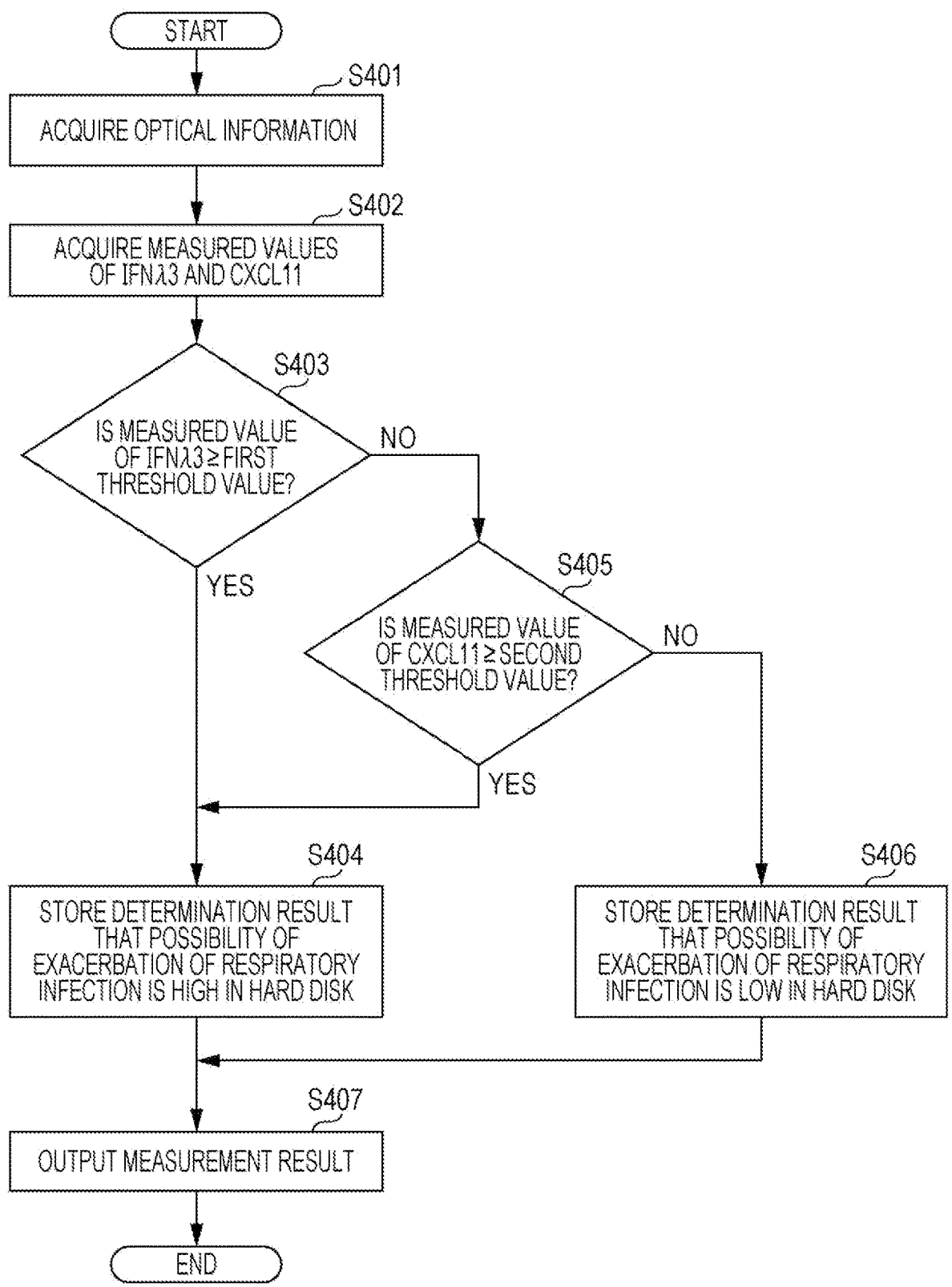
FIG. 4D is a flowchart showing a processing procedure by the device of the present embodiment.

A flow for predicting exacerbation of respiratory infection based on the measured values of IFNλ3 and CXCL11 will be described with reference to FIG. 4D. In FIG. 4D, the threshold value corresponding to the measured value of IFNλ3 is referred to as "first threshold value", and the threshold value corresponding to the measured value of CXCL11 is referred to as "second threshold value".

In step S401, the CPU 310 acquires optical information (chemiluminescent signal) from the immunoassay device 20. In step S402, the CPU 310 calculates measured values of IFNλ3 and CXCL11 from the acquired optical information, and the CPU 310 stores the measured values of IFNλ3 and CXCL11 in the hard disk 313. In step S403, the CPU 310 compares the calculated measured value of IFNλ3 with the first threshold value stored in the hard disk 313. When the measured value of IFNλ3 is greater than or equal to the first threshold value, the process proceeds to step S404. In step S404, the CPU 310 stores in the hard disk 313 a determination result that the possibility of exacerbation of respiratory infection of the subject is high.

In step S403, when the measured value of IFNλ3 is less than the first threshold value, the process proceeds to step S405. In step S405, the CPU 310 compares the calculated measured value of CXCL11 with the second threshold value stored in the hard disk 313. When the measured value of CXCL11 is greater than or equal to the second threshold value, the process proceeds to step S404, and the CPU 310 stores in the hard disk 313 a determination result that the possibility of exacerbation of respiratory infection of the subject is high. In step S405, when the measured value of CXCL11 is less than the second threshold value, the process proceeds to step S406. In step S406, the CPU 310 stores in the hard disk 313 a determination result that the possibility of exacerbation of respiratory infection of the subject is low. In step S407, the CPU 310 outputs the determination result, and the CPU 310 displays the determination result on the display unit 302 or makes a printer to print the determination result. As a result, it is possible to provide a doctor or the like with an index to assist in predicting exacerbation of respiratory infection.

Figure 4E:
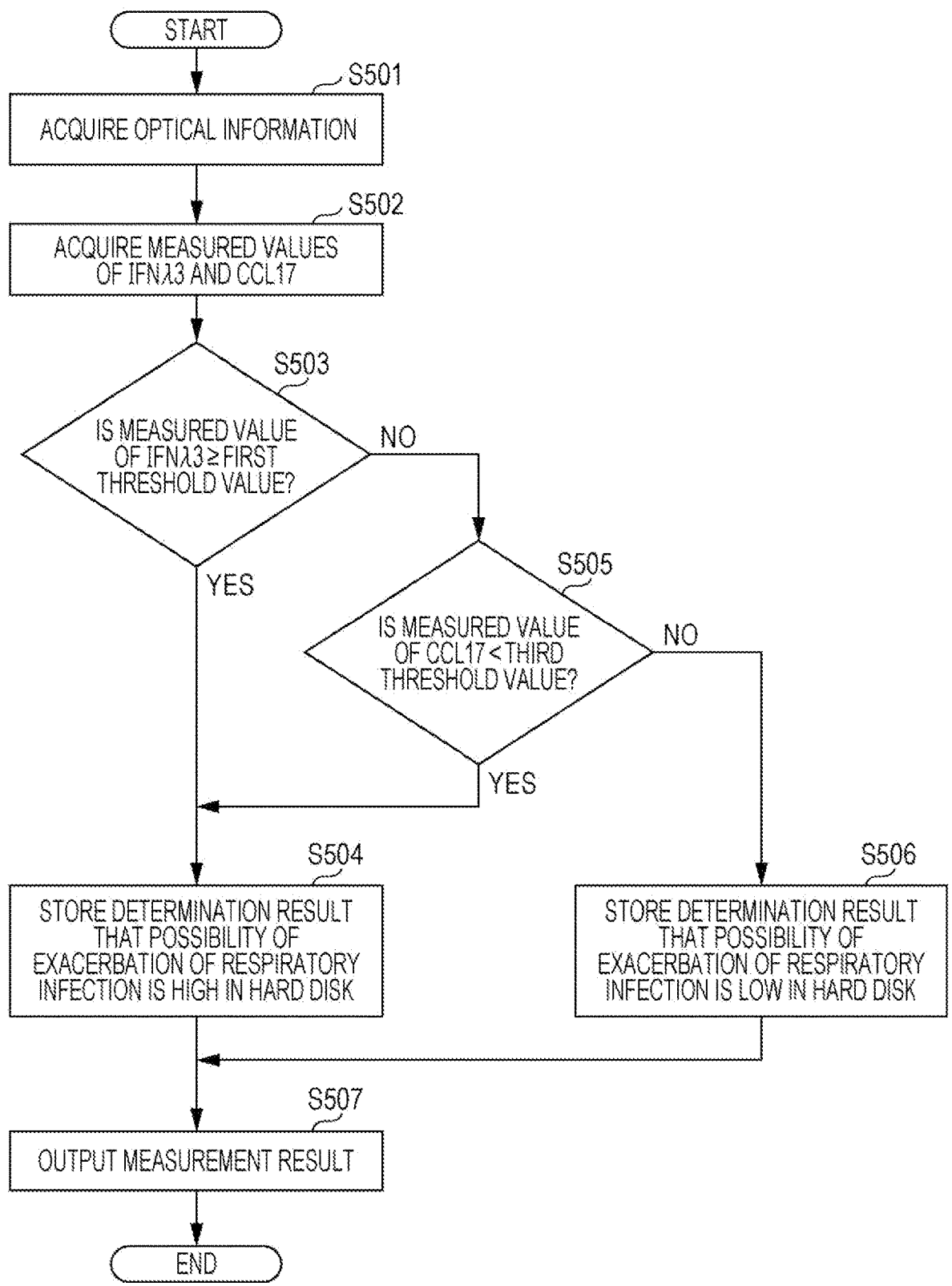
FIG. 4E is a flowchart showing a processing procedure by the device of the present embodiment.

A flow for predicting exacerbation of respiratory infection based on the measured values of IFNλ3 and CCL17 will be described with reference to FIG. 4E. In FIG. 4E, the threshold value corresponding to the measured value of IFNλ3 is referred to as "first threshold value", and the threshold value corresponding to the measured value of CCL17 is referred to as "third threshold value".

In step S501, the CPU 310 acquires optical information (chemiluminescent signal) from the immunoassay device 20. In step S502, the CPU 310 calculates measured values of IFNλ3 and CCL17 from the acquired optical information, and the CPU 310 stores the measured values of IFNλ3 and CCL17 in the hard disk 313. In step S503, the CPU 310 compares the calculated measured value of IFNλ3 with the first threshold value stored in the hard disk 313. When the measured value of IFNλ3 is greater than or equal to the first threshold value, the process proceeds to step S504. In step S504, the CPU 310 stores in the hard disk 313 a determination result that the possibility of exacerbation of respiratory infection of the subject is high. In step S503, when the measured value of IFNλ3 is less than the first threshold value, the process proceeds to step S505. In step S505, the CPU 310 compares the calculated measured value of CCL17 with the third threshold value stored in the hard disk 313. When the measured value of CCL17 is greater than or equal to the third threshold value, the process proceeds to step S506. In step S506, the CPU 310 stores in the hard disk 313 a determination result that the possibility of exacerbation of respiratory infection of the subject is low.

In step S505, when the measured value of CCL17 is less than the third threshold value, the process proceeds to step S504, and the CPU 310 stores in the hard disk 313 a determination result that the possibility of exacerbation of respiratory infection of the subject is high. In step S507, the CPU 310 outputs the determination result, and the CPU 310 displays the determination result on the display unit 302 or makes a printer to print the determination result. As a result, it is possible to provide a doctor or the like with an index to assist in predicting exacerbation of respiratory infection.

Figure 4F:
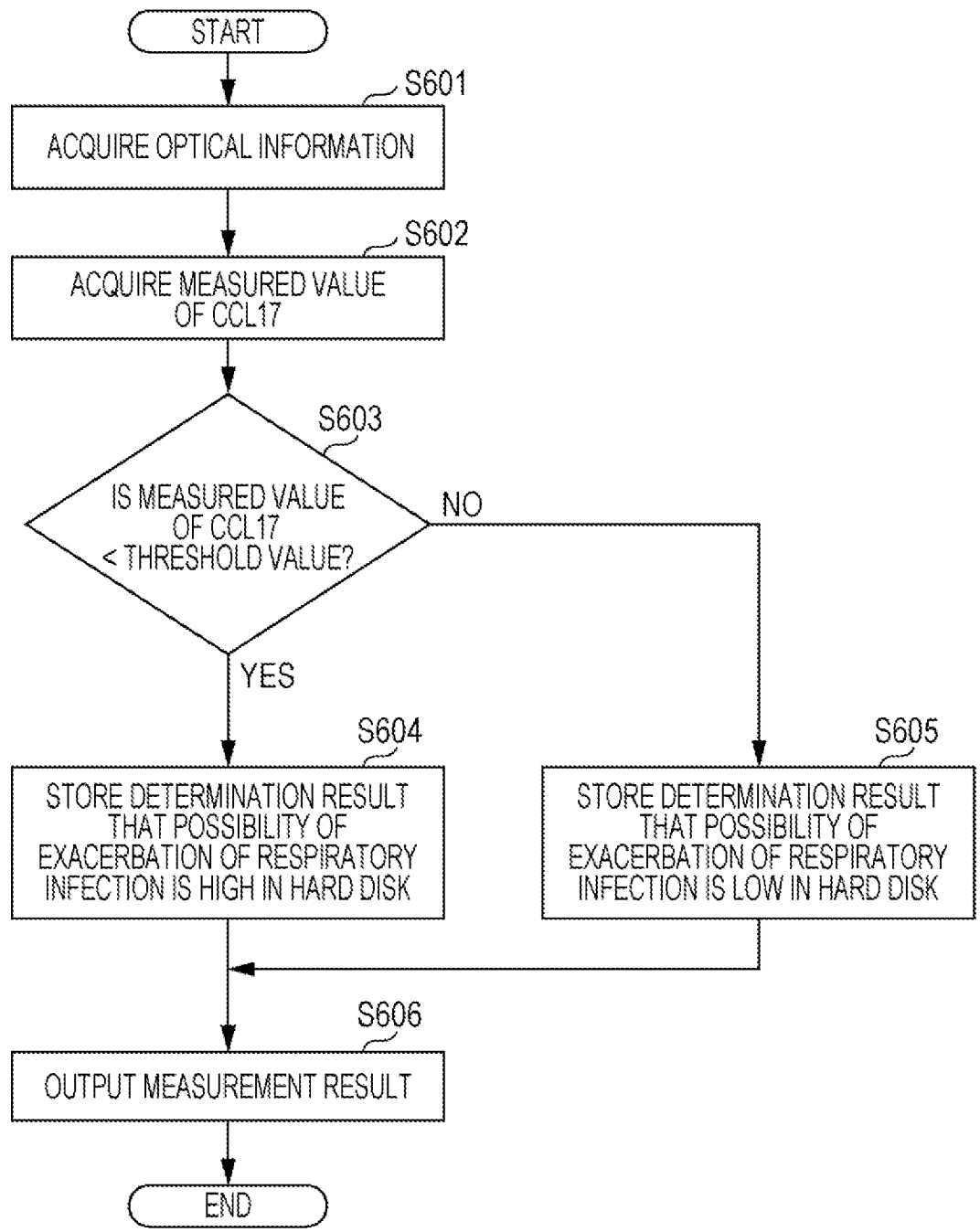
FIG. 4F is a flowchart showing a processing procedure by the device of the present embodiment.
Figure 5A:
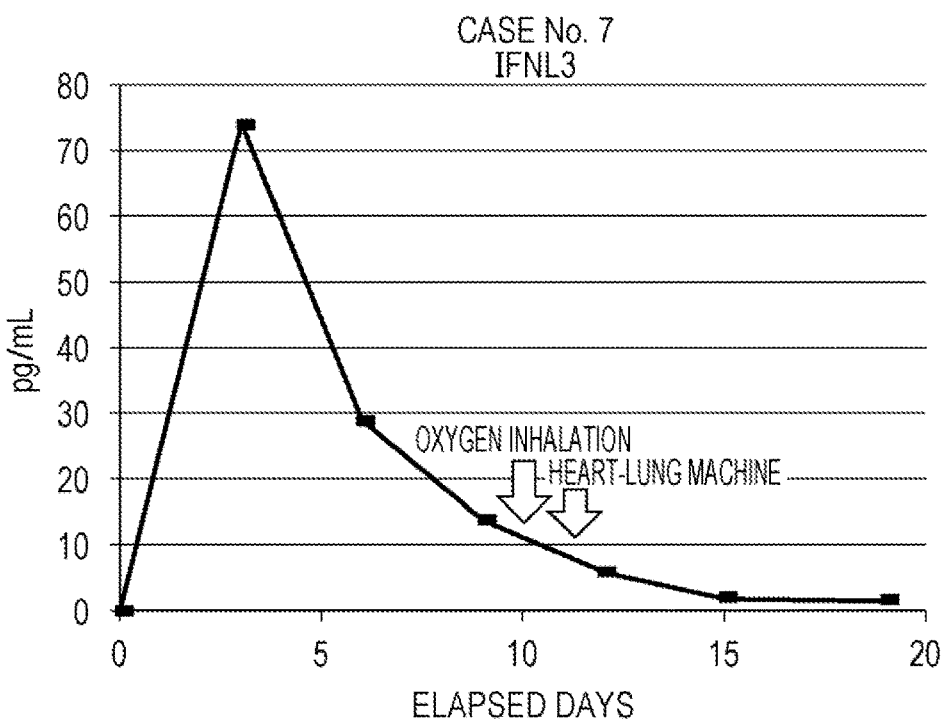
FIG. 5A is a graph showing transition of IFNλ3 concentration in serum of a patient in case No. 7.
Figure 5B:
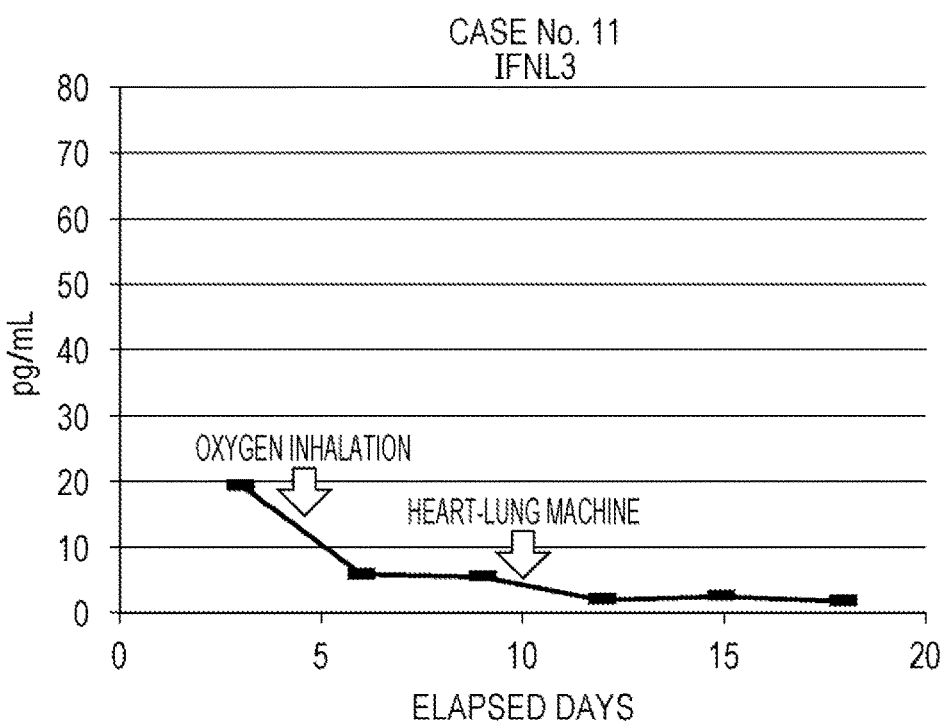
FIG. 5B is a graph showing transition of IFNλ3 concentration in serum of a patient in case No. 11.
Figure 5C:
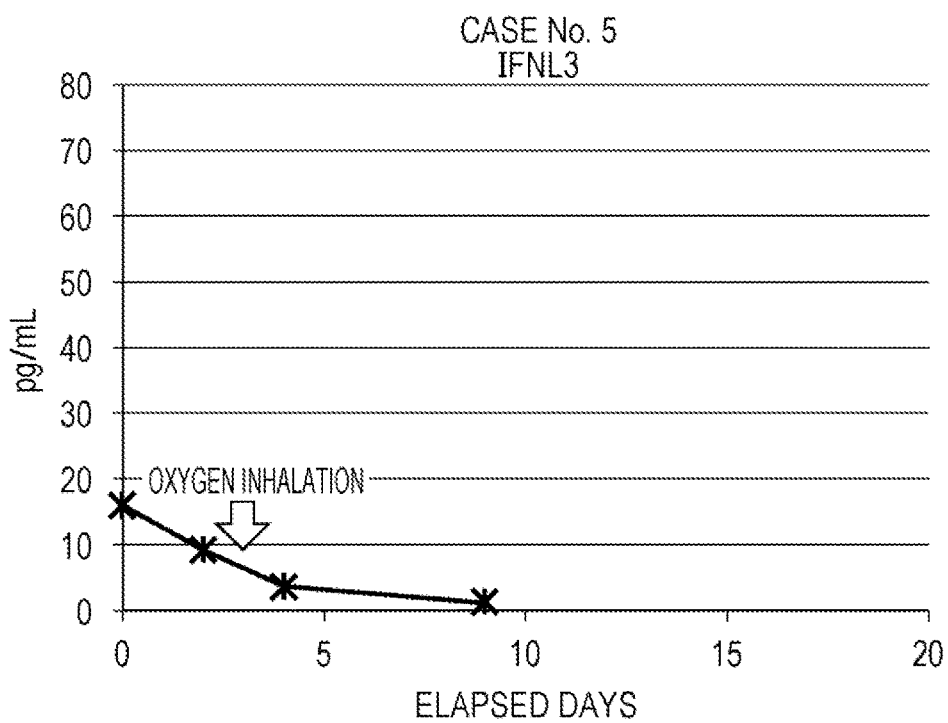
FIG. 5C is a graph showing transition of IFNλ3 concentration in serum of a patient in case No. 5.
Figure 5D:
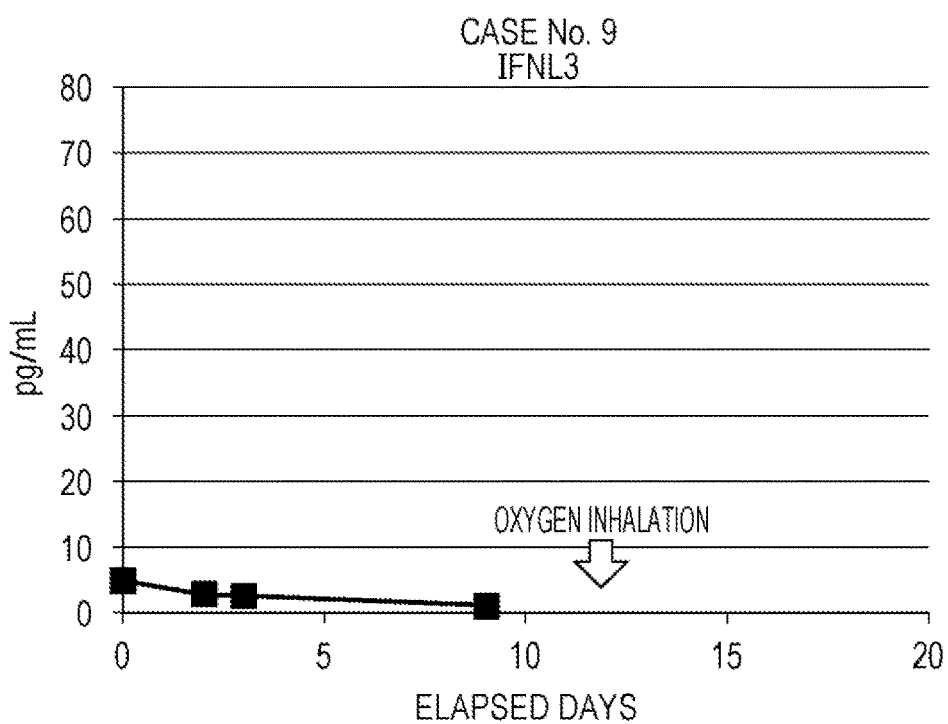
FIG. 5D is a graph showing transition of IFNλ3 concentration in serum of a patient in case No. 9.
Figure 5E:
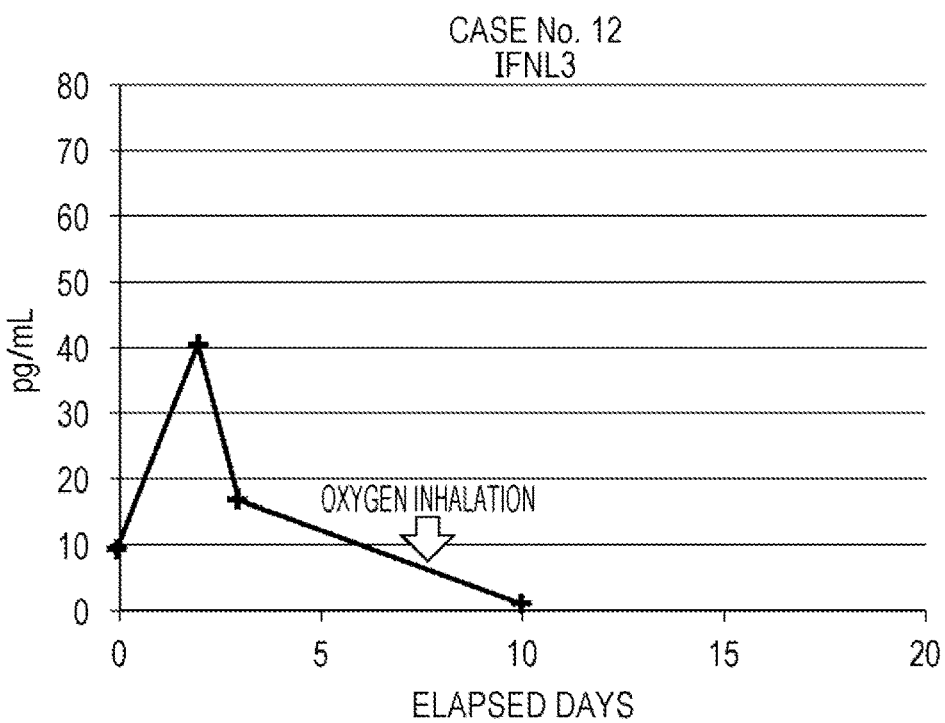
FIG. 5E is a graph showing transition of IFNλ3 concentration in serum of a patient in case No. 12.
Figure 5F:
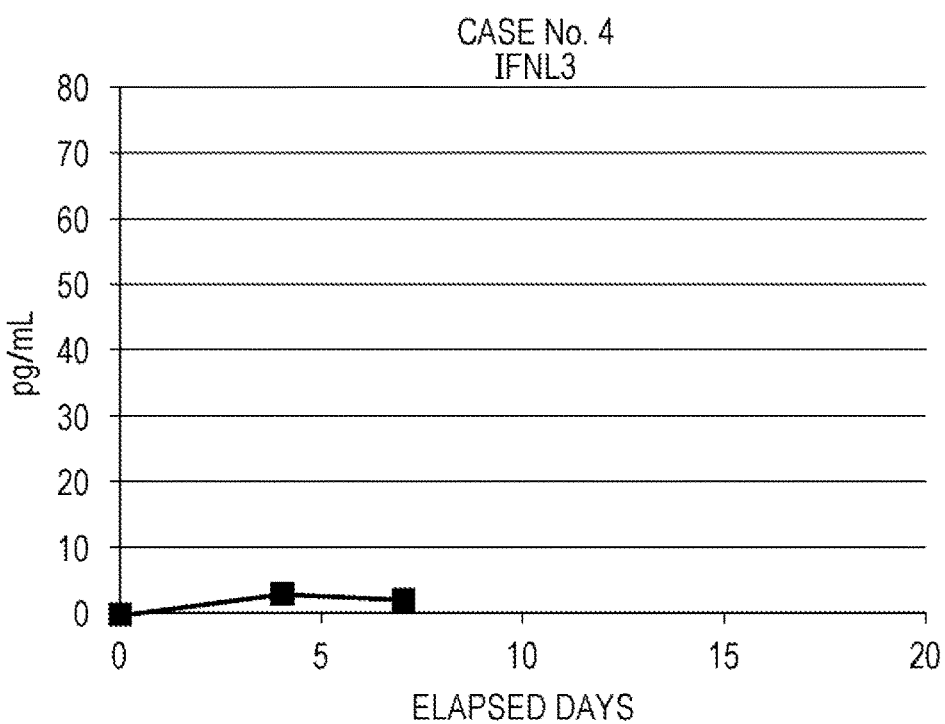
FIG. 5F is a graph showing transition of IFNλ3 concentration in serum of a patient in case No. 4.
Figure 5G:
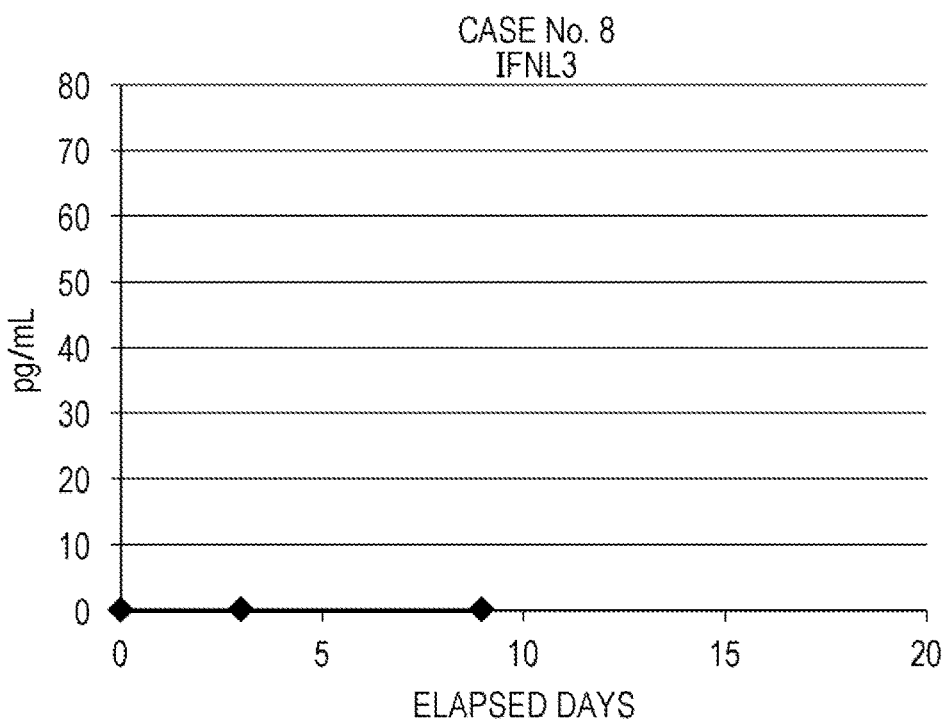
FIG. 5G is a graph showing transition of IFNλ3 concentration in serum of a patient in case No. 8.
Figure 5H:
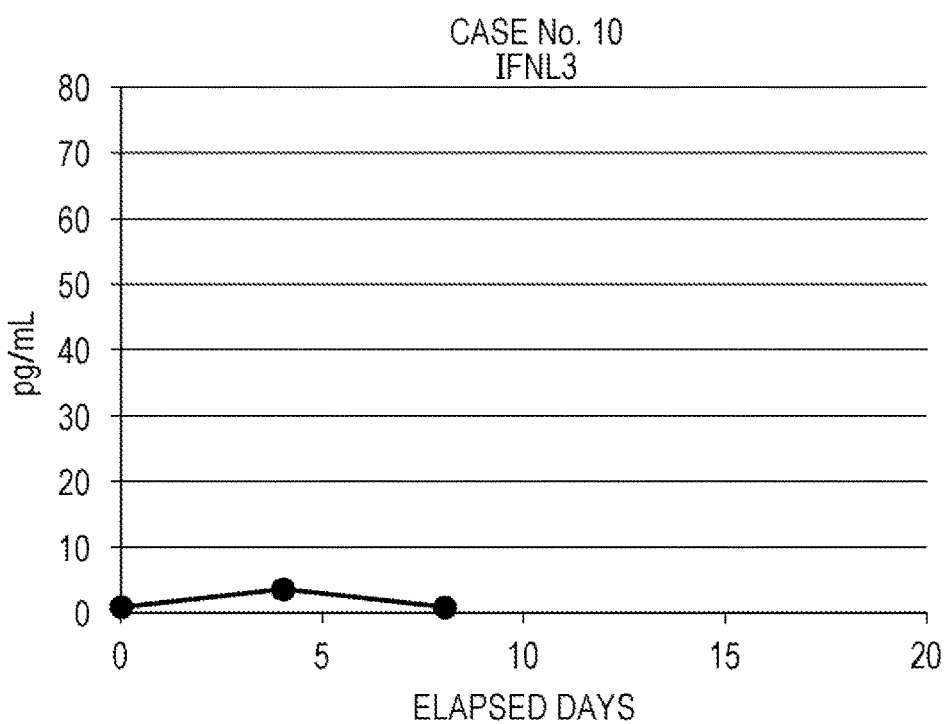
FIG. 5H is a graph showing transition of IFNλ3 concentration in serum of a patient in case No. 10.
Figure 6A:
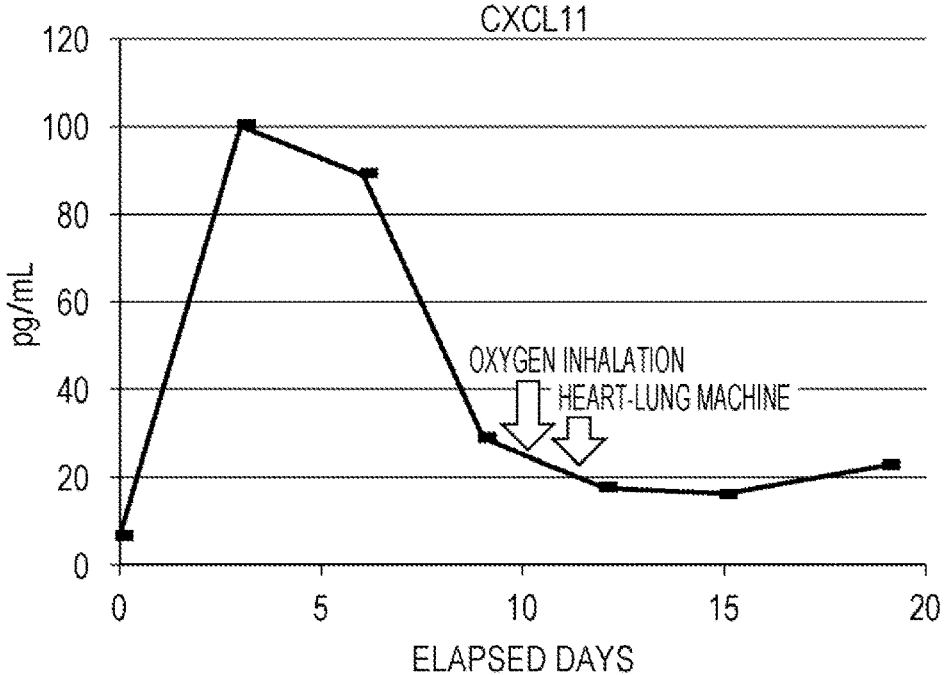
FIG. 6A is a graph showing transition of CXCL11 concentration in serum of a patient in case No. 7.
Figure 6B:
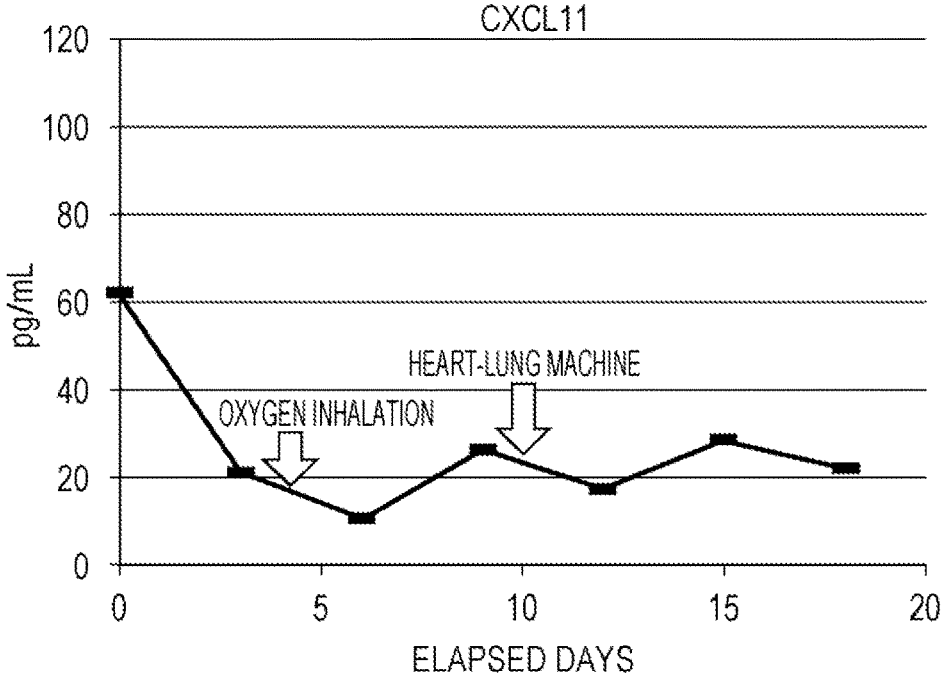
FIG. 6B is a graph showing transition of CXCL11 concentration in serum of a patient in case No. 11.
Figure 6C:
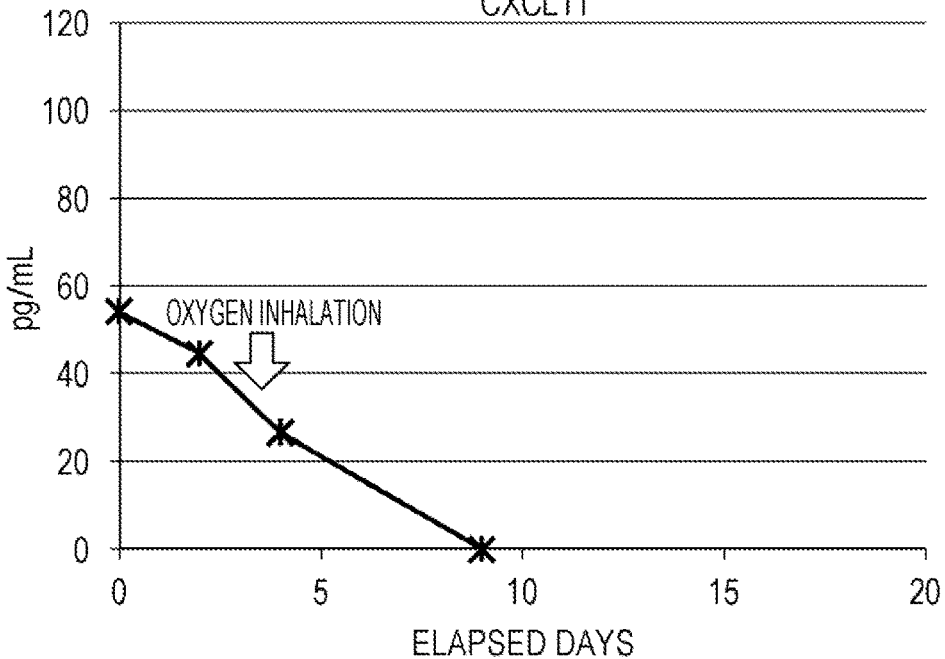
FIG. 6C is a graph showing transition of CXCL11 concentration in serum of a patient in case No. 5.
Figure 6D:
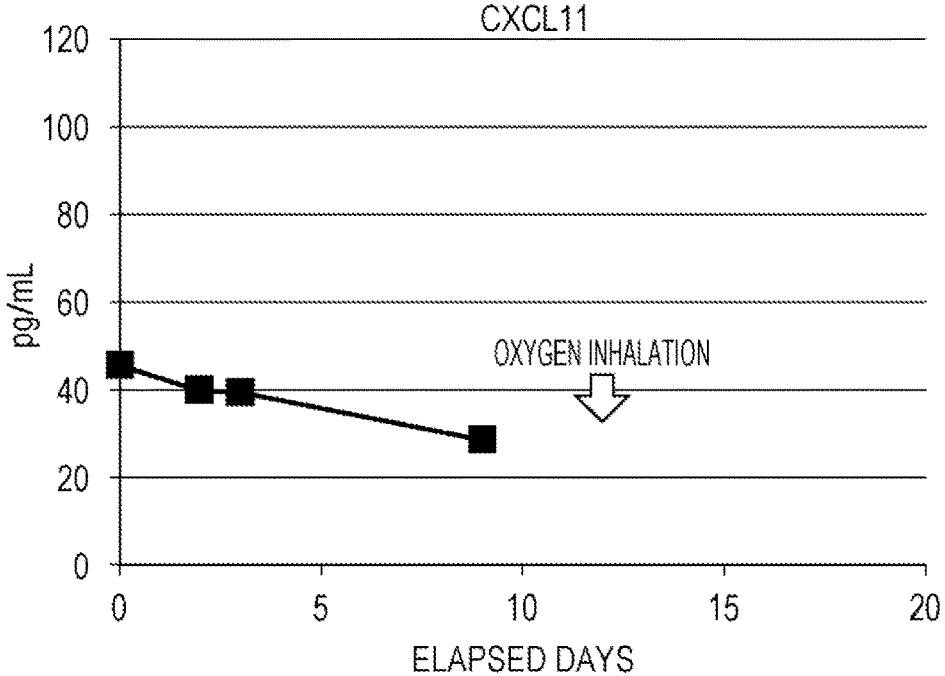
FIG. 6D is a graph showing transition of CXCL11 concentration in serum of a patient in case No. 9.
Figure 6E:
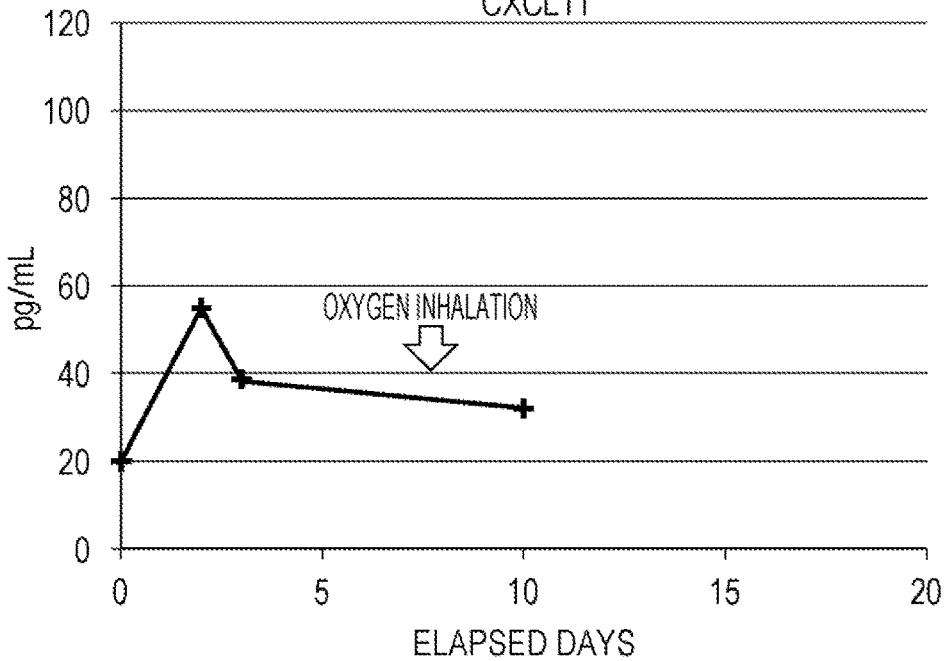
FIG. 6E is a graph showing transition of CXCL11 concentration in serum of a patient in case No. 12.
Figure 6F:
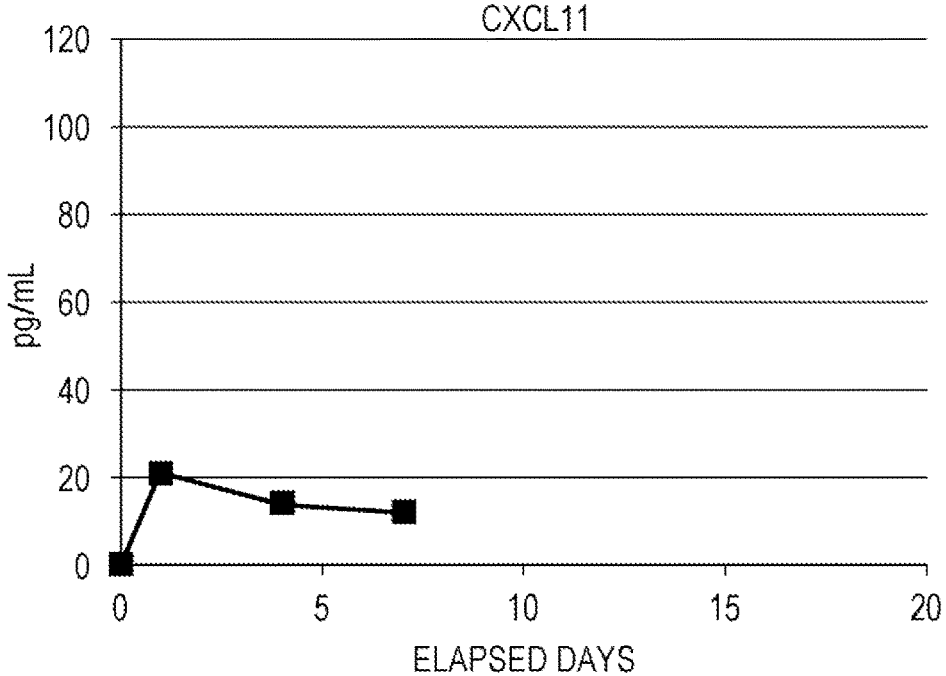
FIG. 6F is a graph showing transition of CXCL11 concentration in serum of a patient in case No. 4.
Figure 6G:
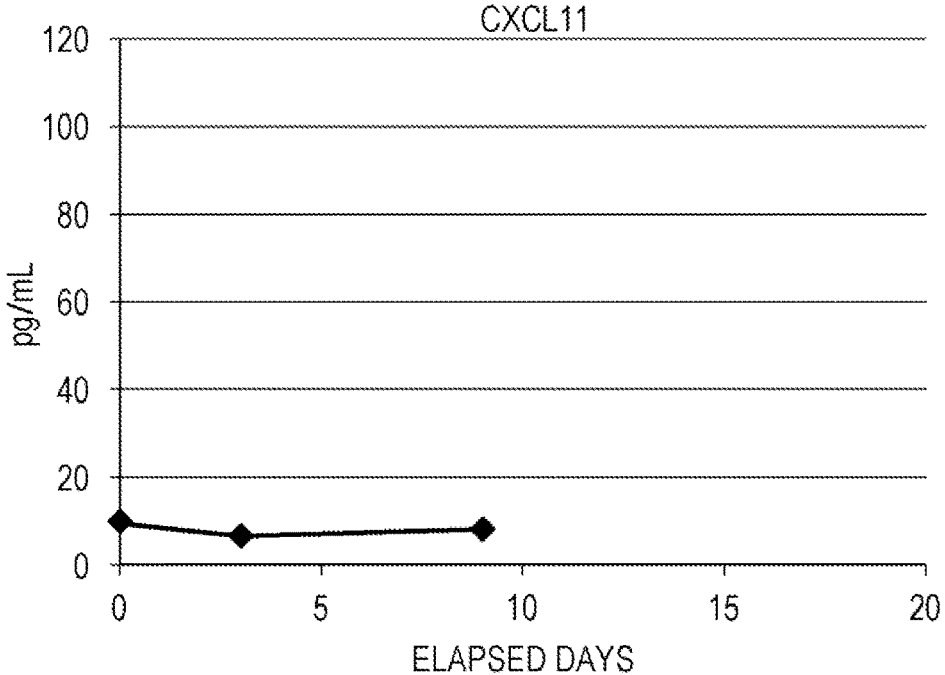
FIG. 6G is a graph showing transition of CXCL11 concentration in serum of a patient in case No. 8.
Figure 6H:
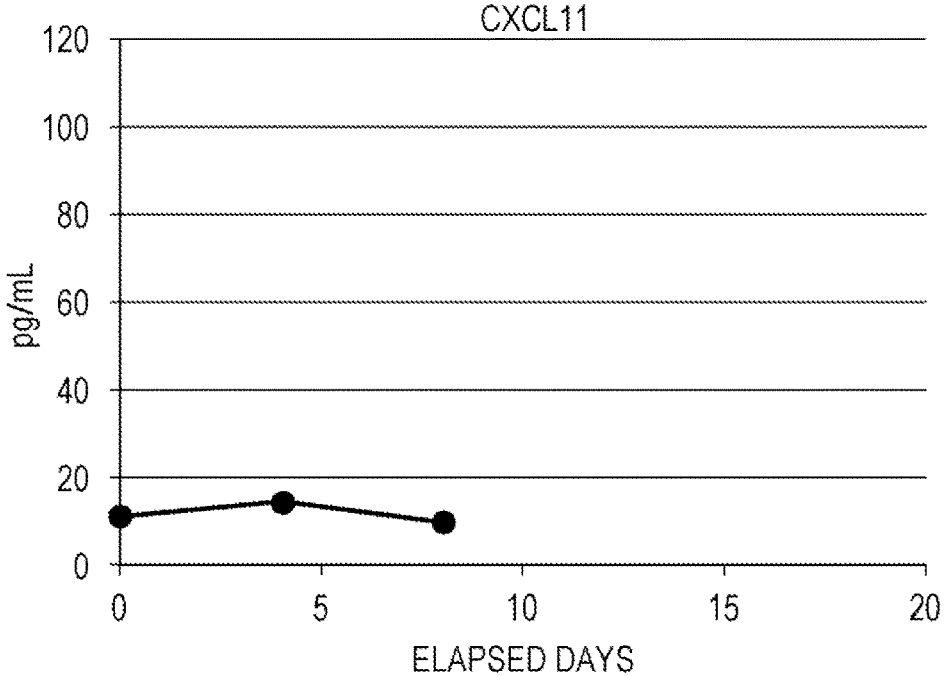
FIG. 6H is a graph showing transition of CXCL11 concentration in serum of a patient in case No. 10.
Figure 7C:
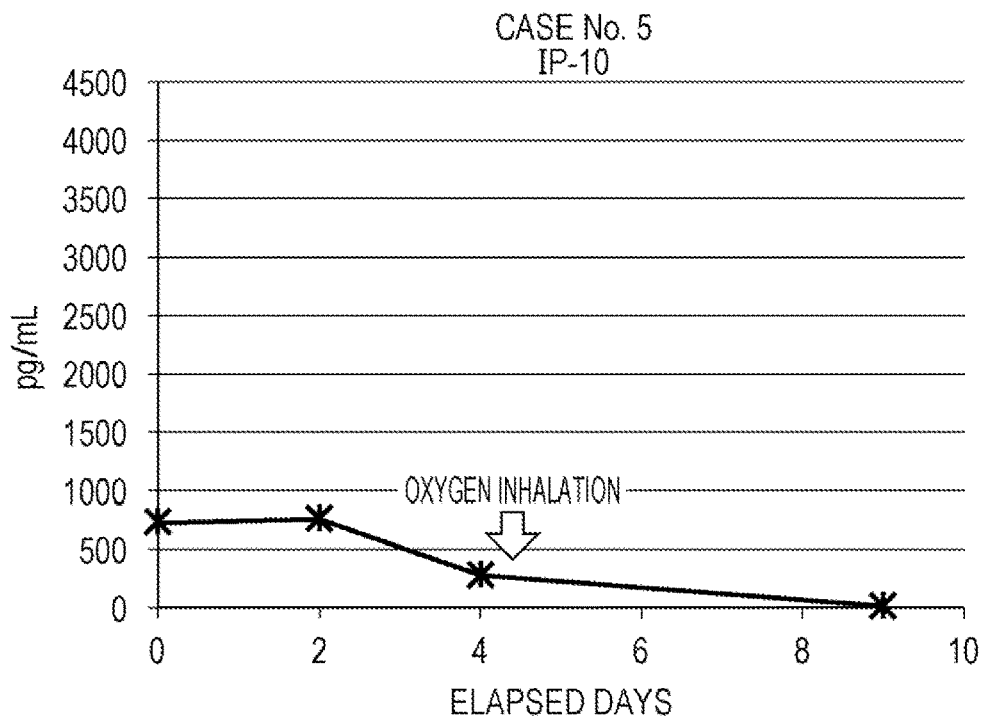
FIG. 7C is a graph showing transition of IP-10 concentration in serum of a patient in case No. 5.
Figure 7D:
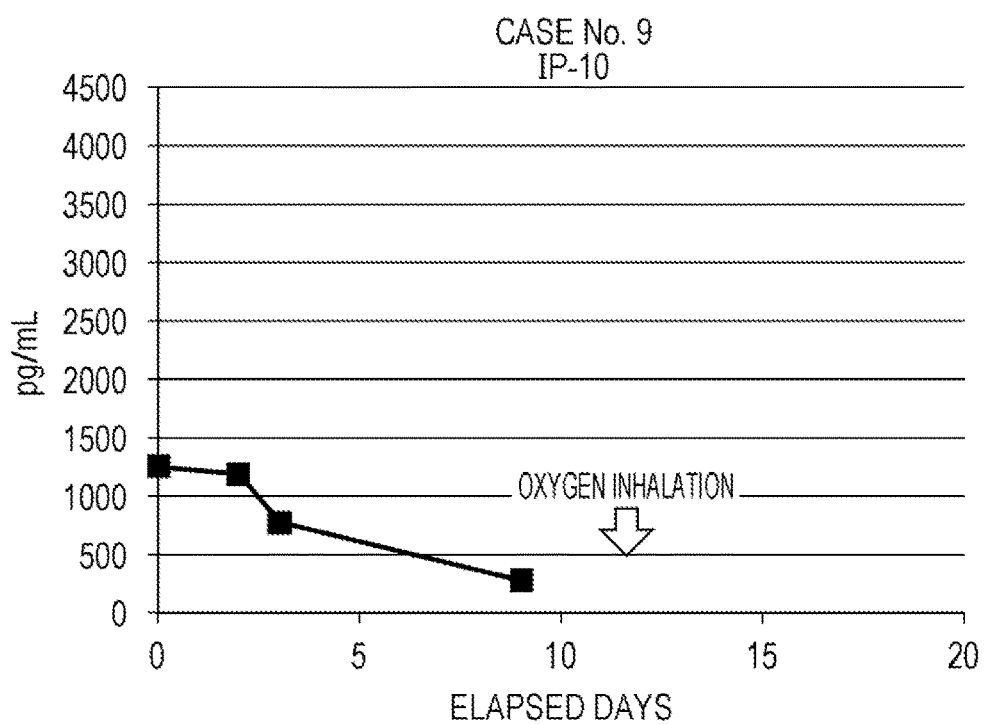
FIG. 7D is a graph showing transition of IP-10 concentration in serum of a patient in case No. 9.
Figure 7E:
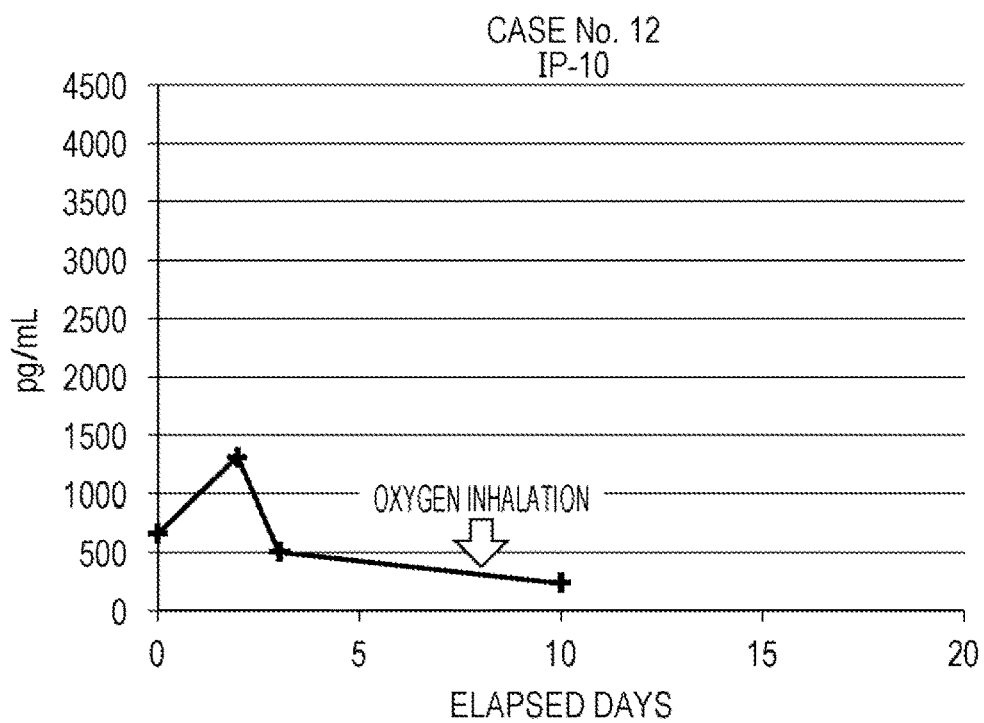
FIG. 7E is a graph showing transition of IP-10 concentration in serum of a patient in case No. 12.
Figure 7F:
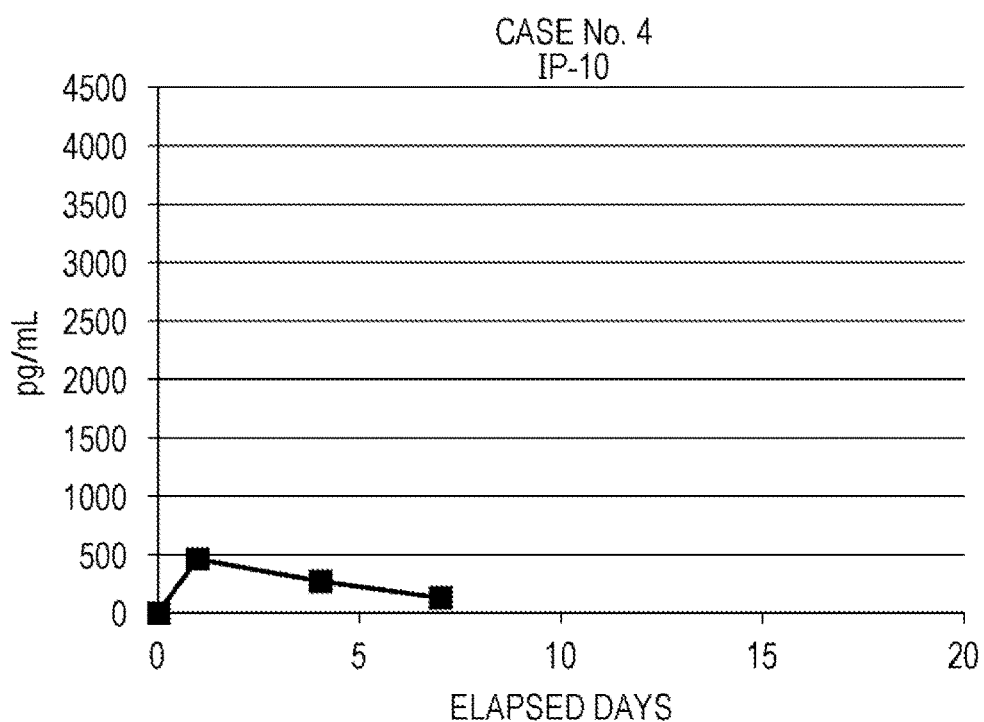
FIG. 7F is a graph showing transition of IP-10 concentration in serum of a patient in case No. 4.
Figure 7G:
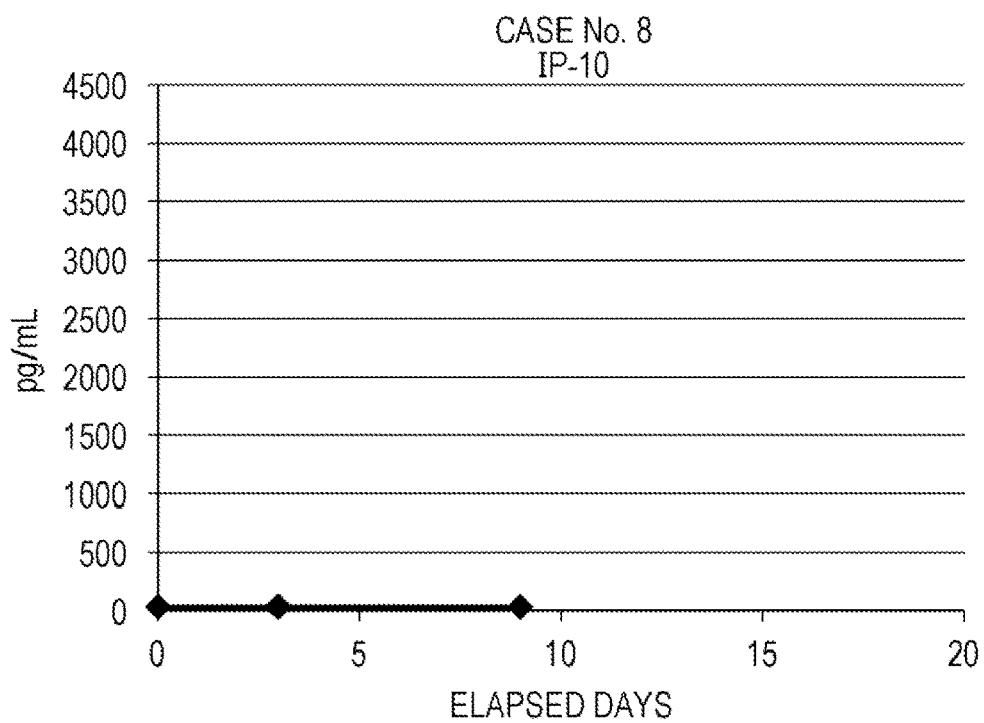
FIG. 7G is a graph showing transition of IP-10 concentration in serum of a patient in case No. 8.
Figure 7H:
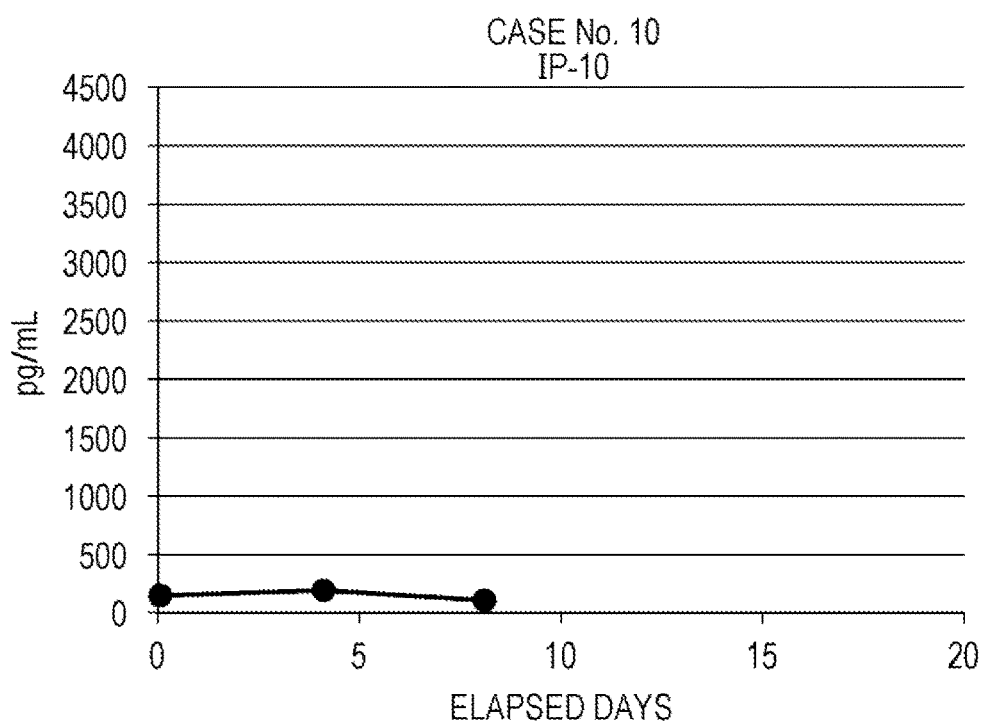
FIG. 7H is a graph showing transition of IP-10 concentration in serum of a patient in case No. 10.
Figure 8A:
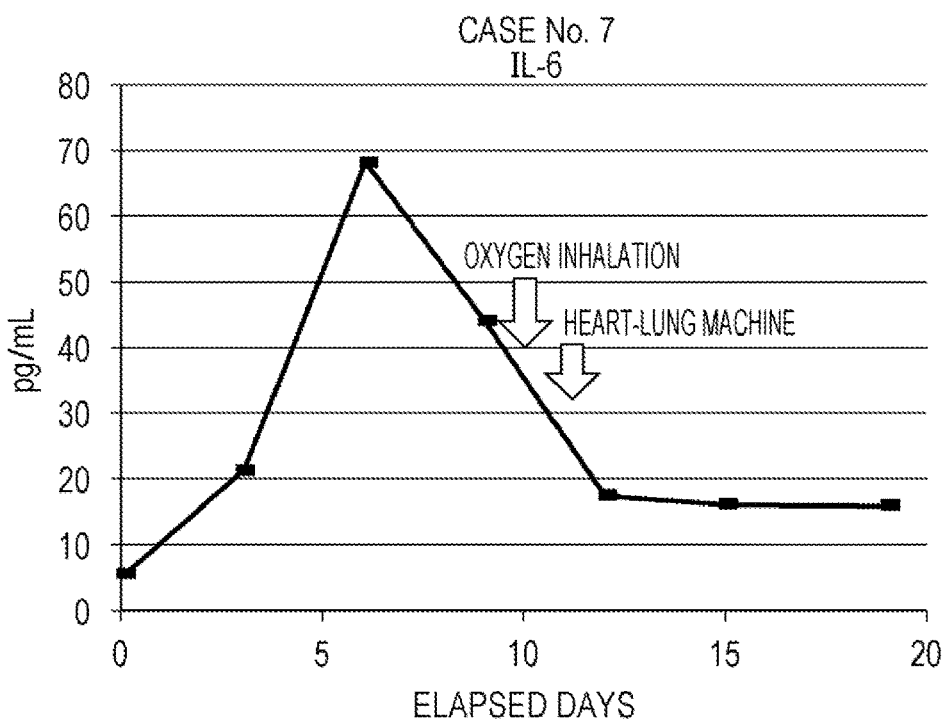
FIG. 8A is a graph showing transition of IL-6 concentration in serum of a patient in case No. 7.
Figure 8B:
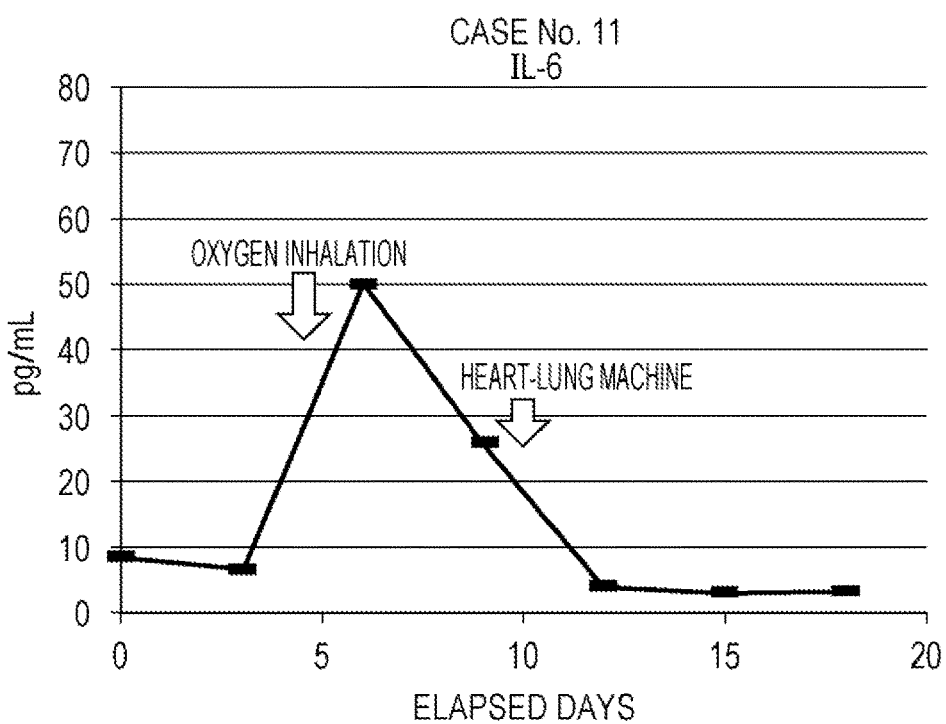
FIG. 8B is a graph showing transition of IL-6 concentration in serum of a patient in case No. 11.
Figure 8C:
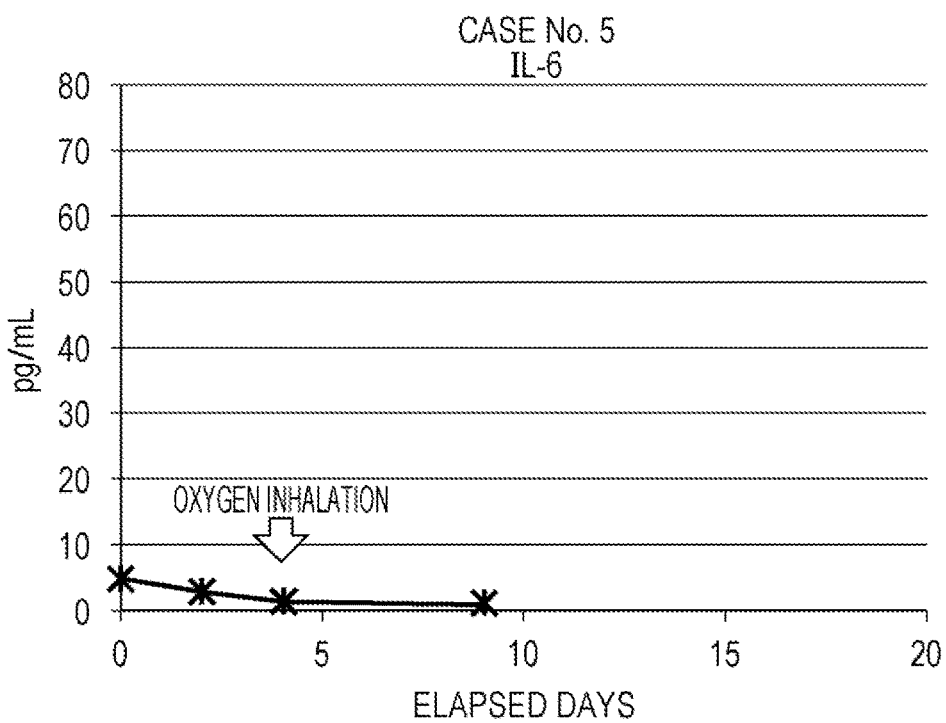
FIG. 8C is a graph showing transition of IL-6 concentration in serum of a patient in case No. 5.
Figure 8D:
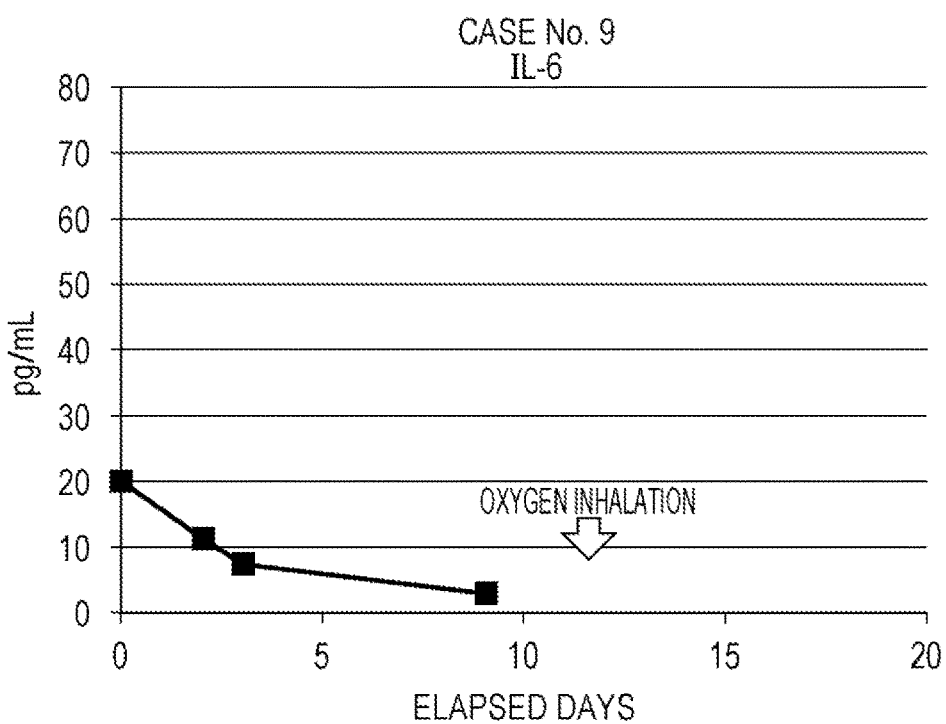
FIG. 8D is a graph showing transition of IL-6 concentration in serum of a patient in case No. 9.
Figure 8E:
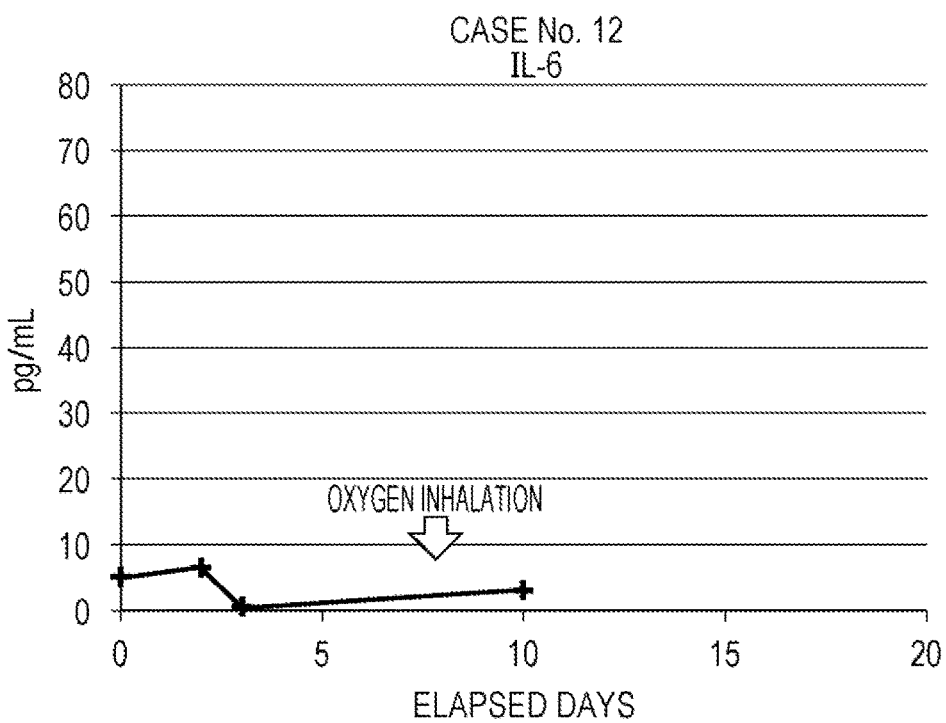
FIG. 8E is a graph showing transition of IL-6 concentration in serum of a patient in case No. 12.
Figure 8F:
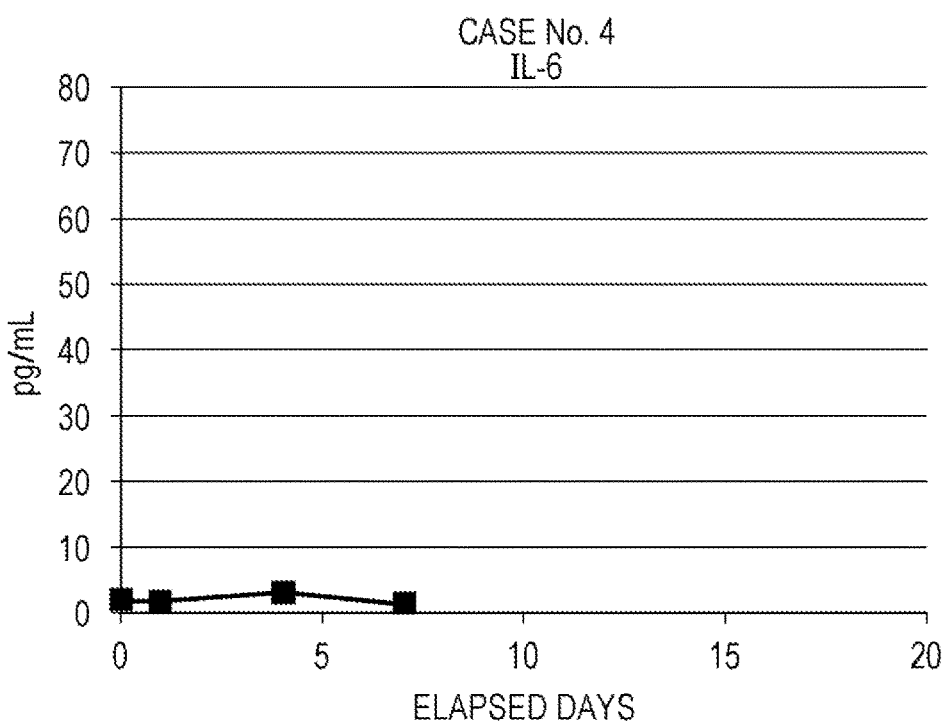
FIG. 8F is a graph showing transition of IL-6 concentration in serum of a patient in case No. 4.
Figure 8G:
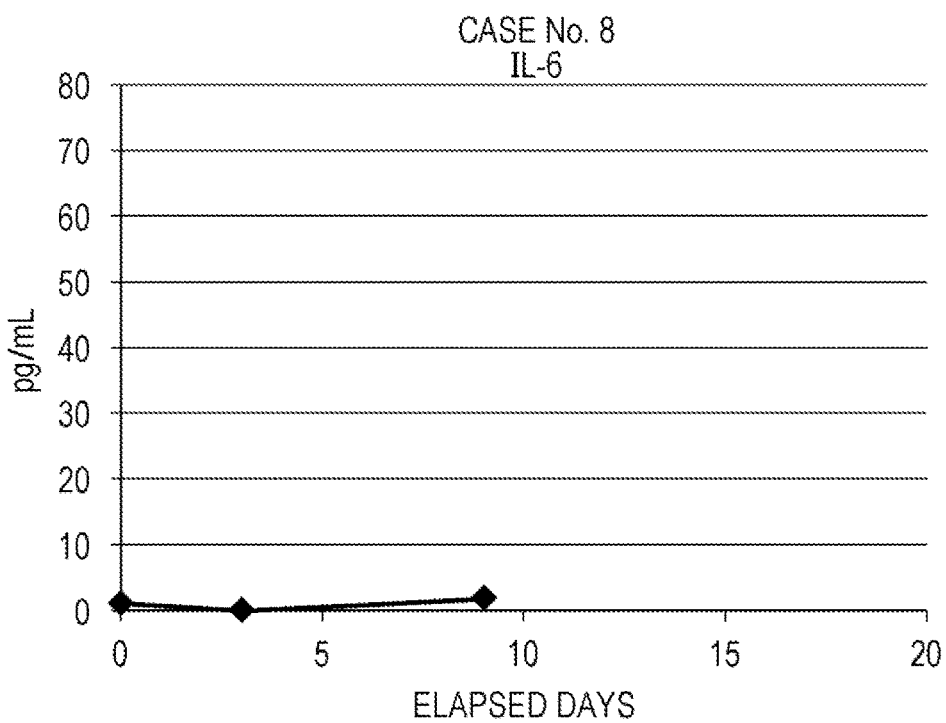
FIG. 8G is a graph showing transition of IL-6 concentration in serum of a patient in case No. 8.
Figure 8H:
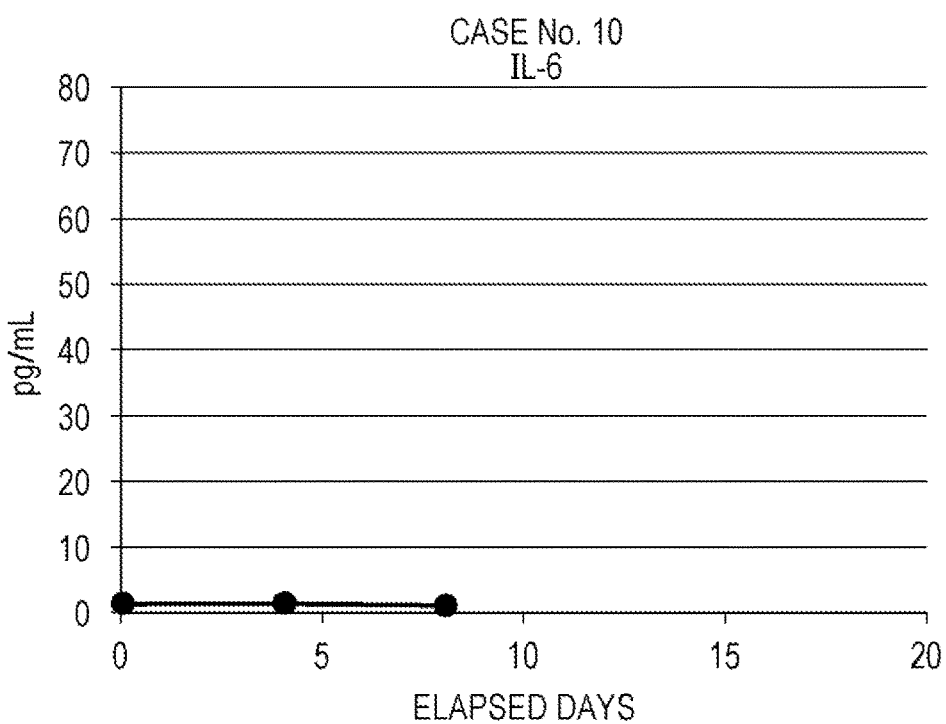
FIG. 8H is a graph showing transition of IL-6 concentration in serum of a patient in case No. 10.
Figure 9A:
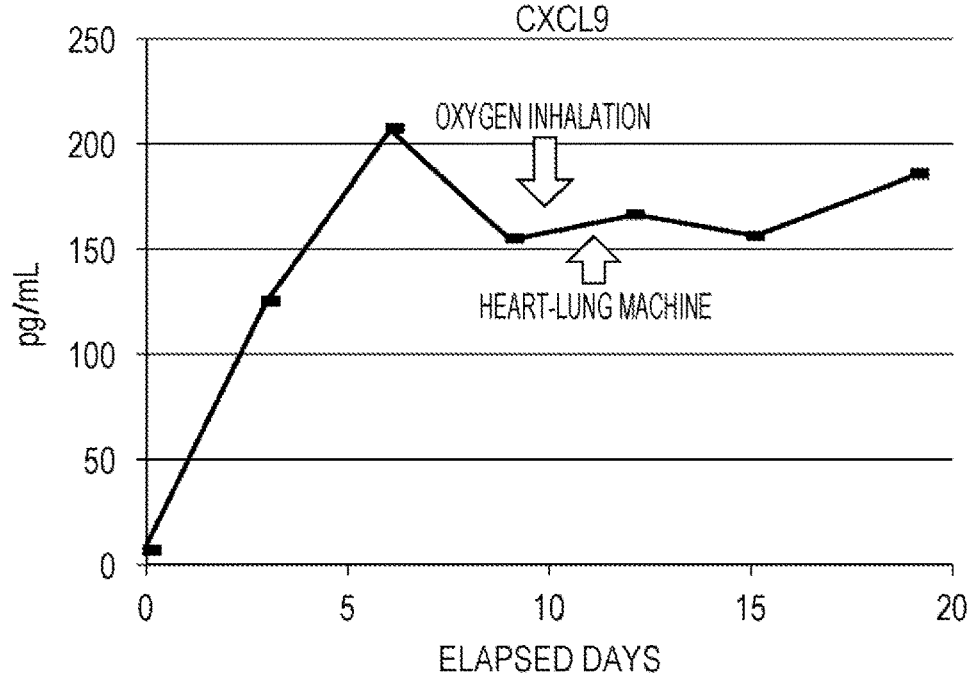
FIG. 9A is a graph showing transition of CXCL9 concentration in serum of a patient in case No. 7.
Figure 9B:
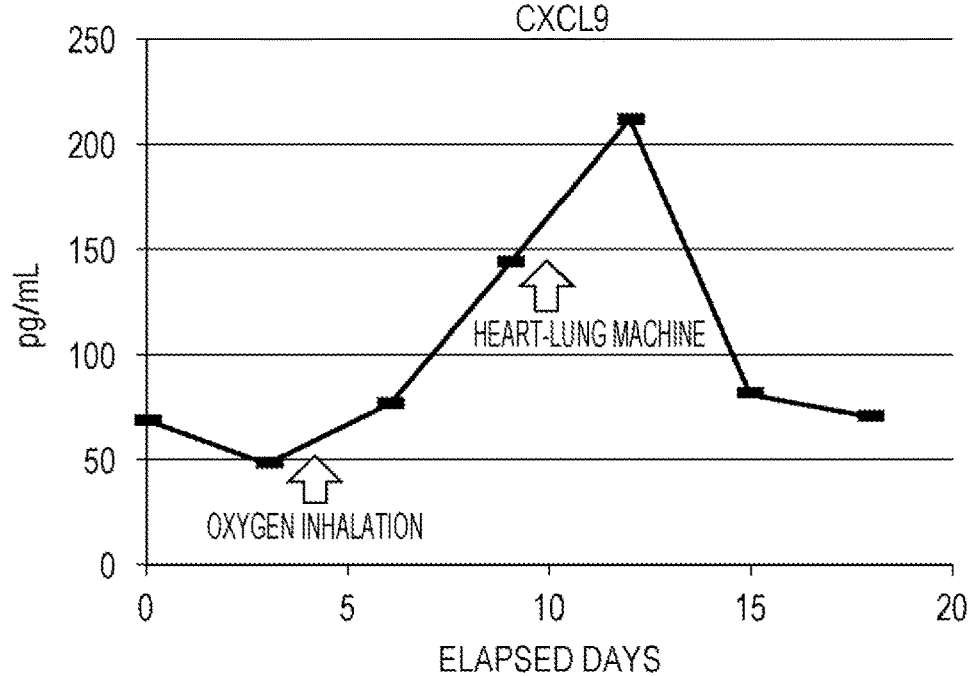
FIG. 9B is a graph showing transition of CXCL9 concentration in serum of a patient in case No. 11.
Figure 9C:
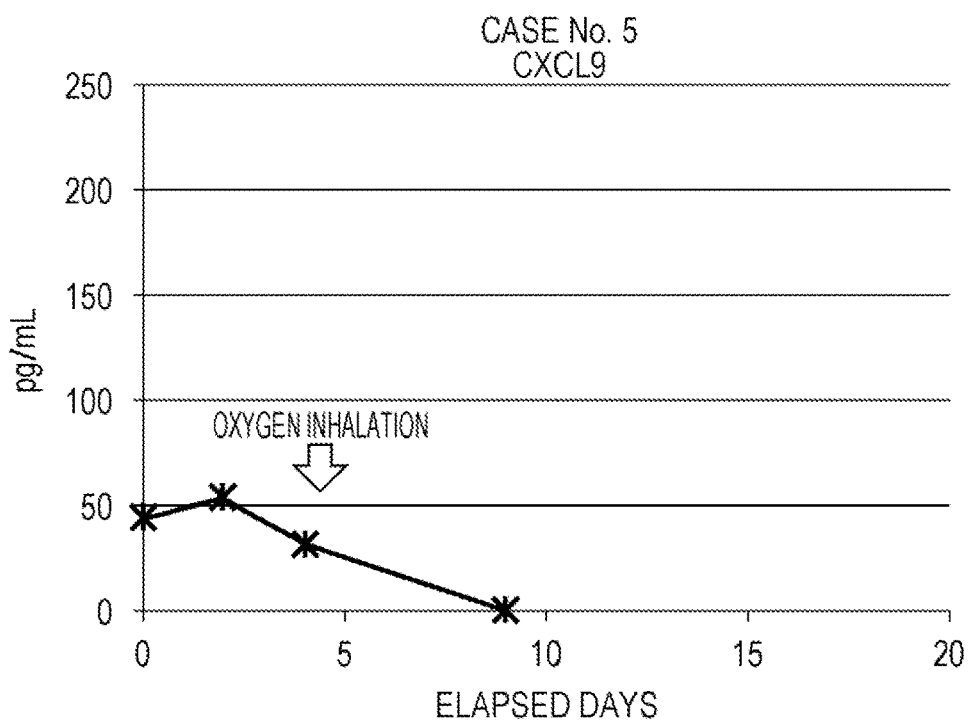
FIG. 9C is a graph showing transition of CXCL9 concentration in serum of a patient in case No. 5.
Figure 9D:
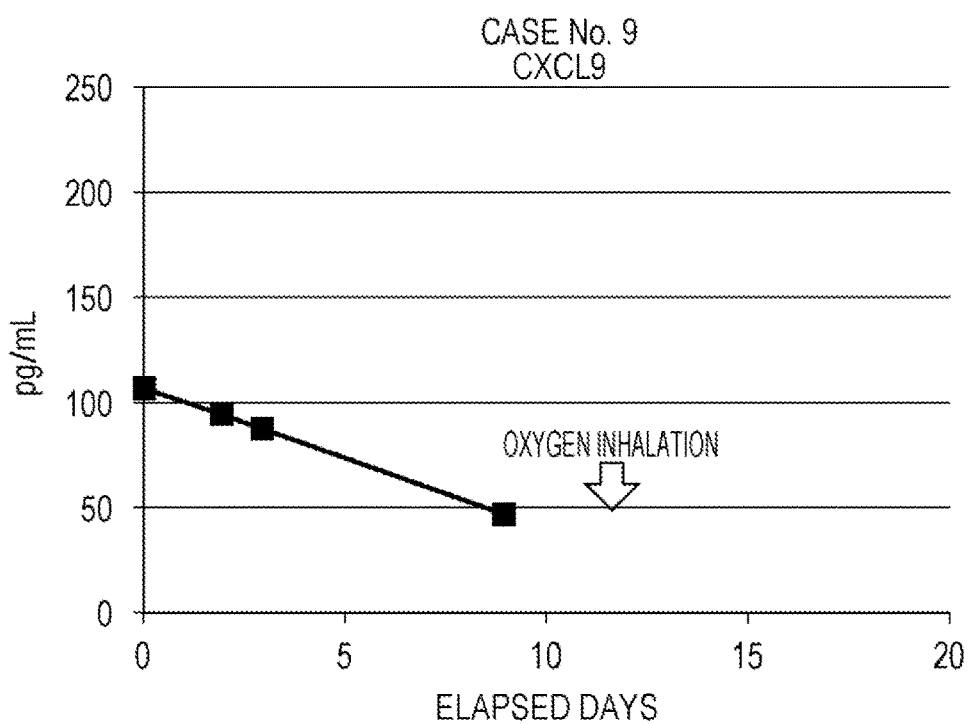
FIG. 9D is a graph showing transition of CXCL9 concentration in serum of a patient in case No. 9.
Figure 9E:
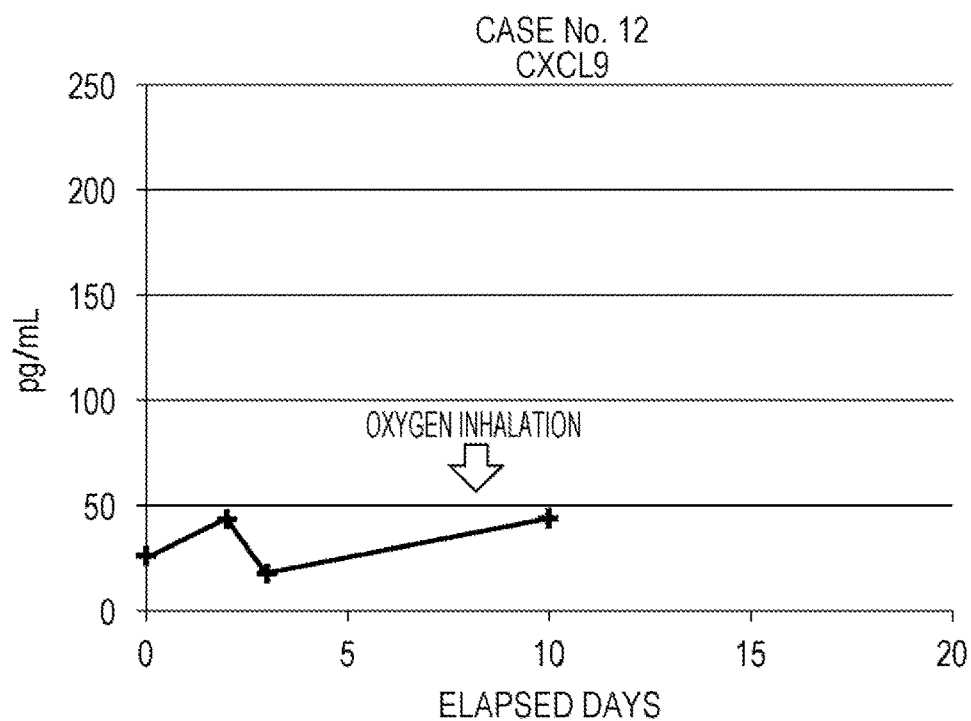
FIG. 9E is a graph showing transition of CXCL9 concentration in serum of a patient in case No. 12.
Figure 9F:
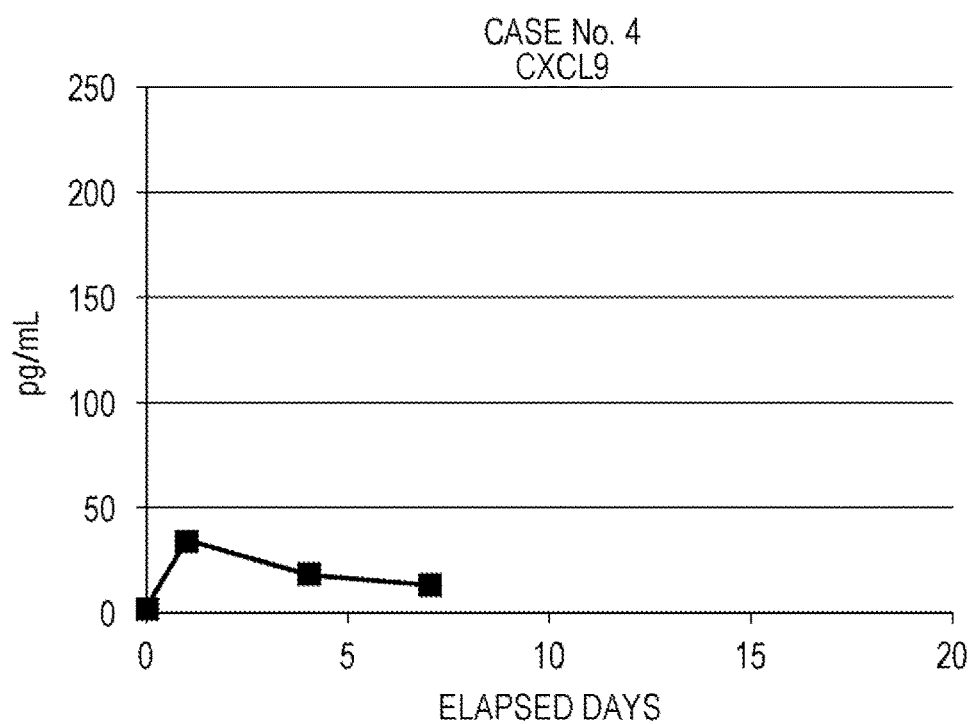
FIG. 9F is a graph showing transition of CXCL9 concentration in serum of a patient in case No. 4.
Figure 9G:
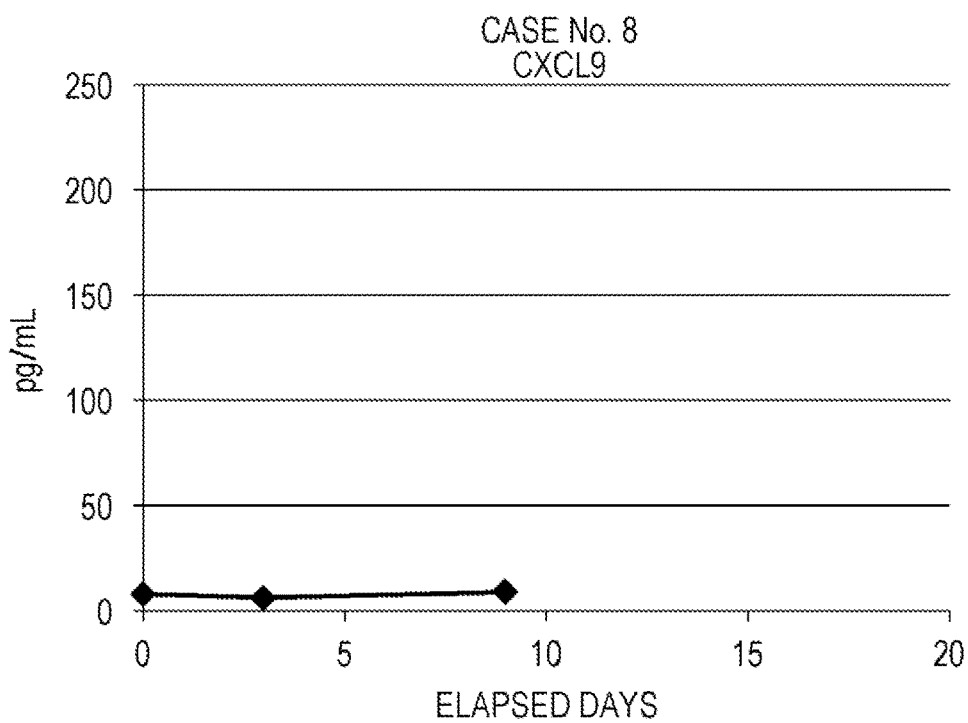
FIG. 9G is a graph showing transition of CXCL9 concentration in serum of a patient in case No. 8.
Figure 9H:
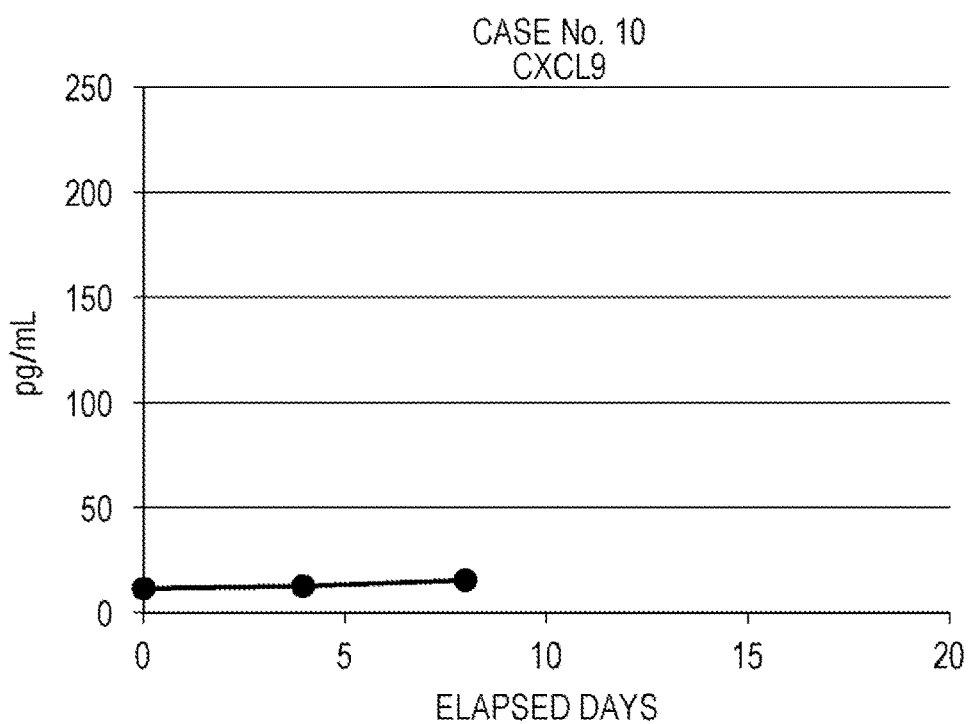
FIG. 9H is a graph showing transition of CXCL9 concentration in serum of a patient in case No. 10.
Figure 10A:
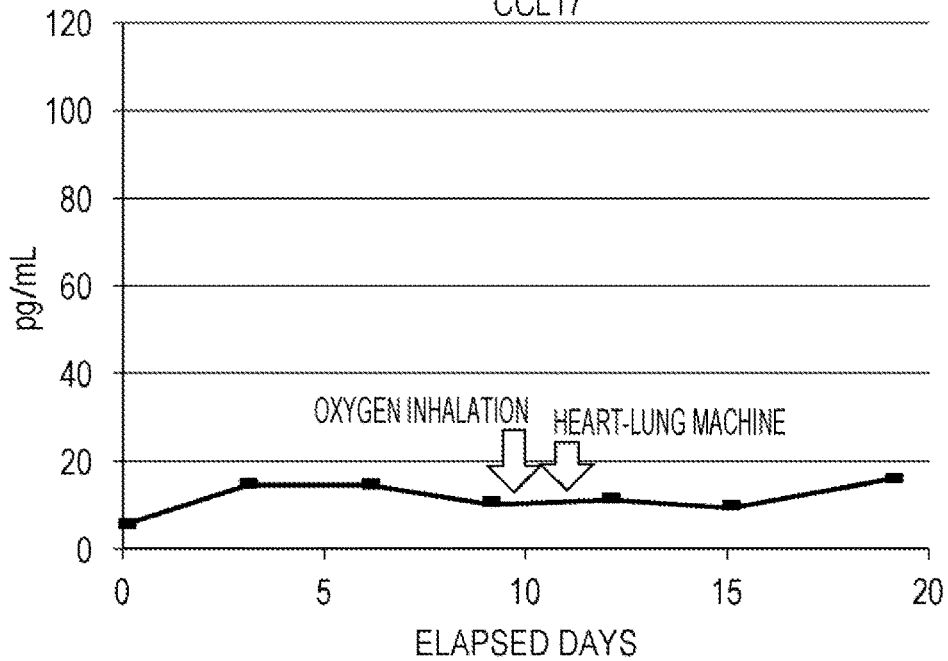
FIG. 10A is a graph showing transition of CCL17 concentration in serum of a patient in case No. 7.
Figure 10B:
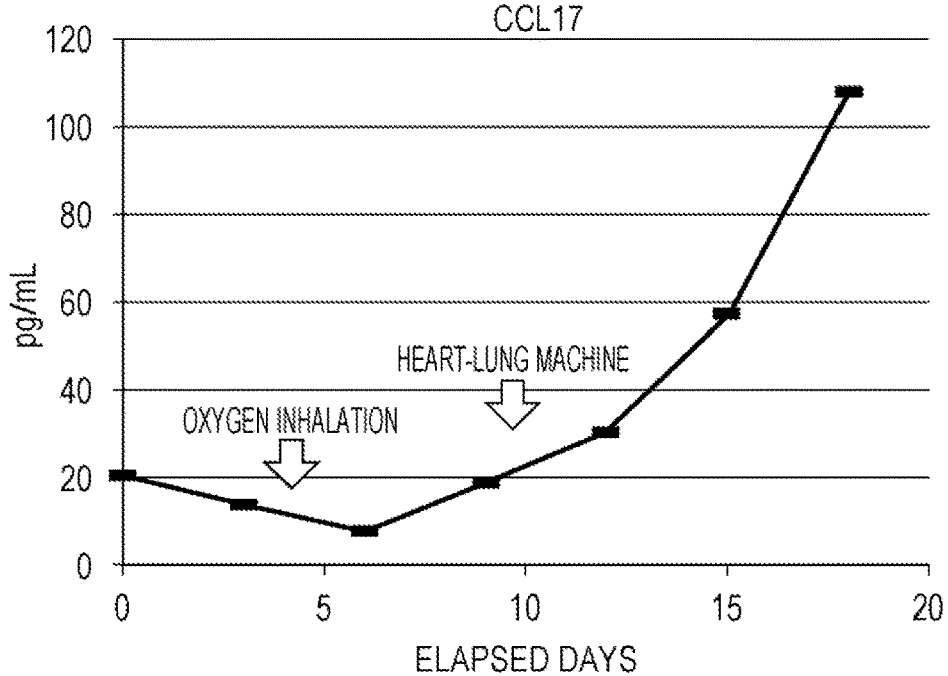
FIG. 10B is a graph showing transition of CCL17 concentration in serum of a patient in case No. 11.
Figure 10C:
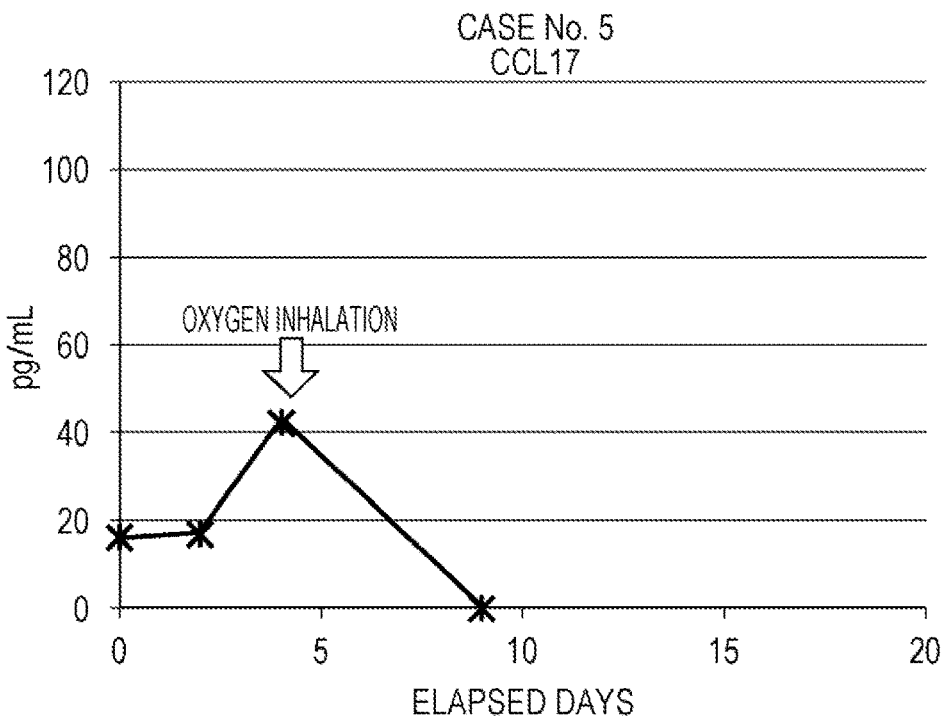
FIG. 10C is a graph showing transition of CCL17 concentration in serum of a patient in case No. 5.
Figure 10D:
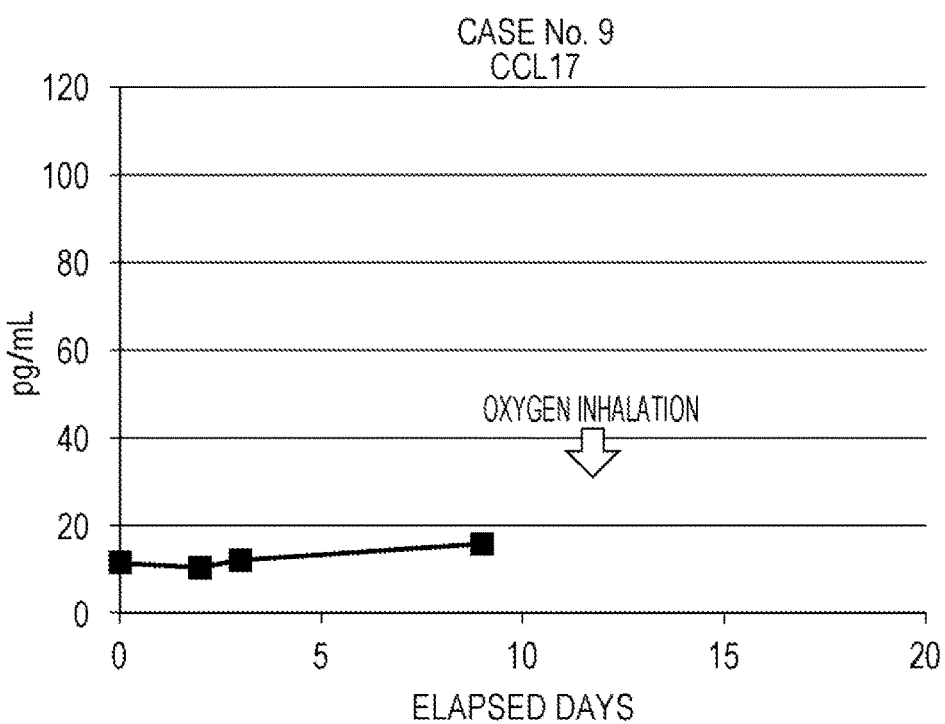
FIG. 10D is a graph showing transition of CCL17 concentration in serum of a patient in case No. 9.
Figure 10E:
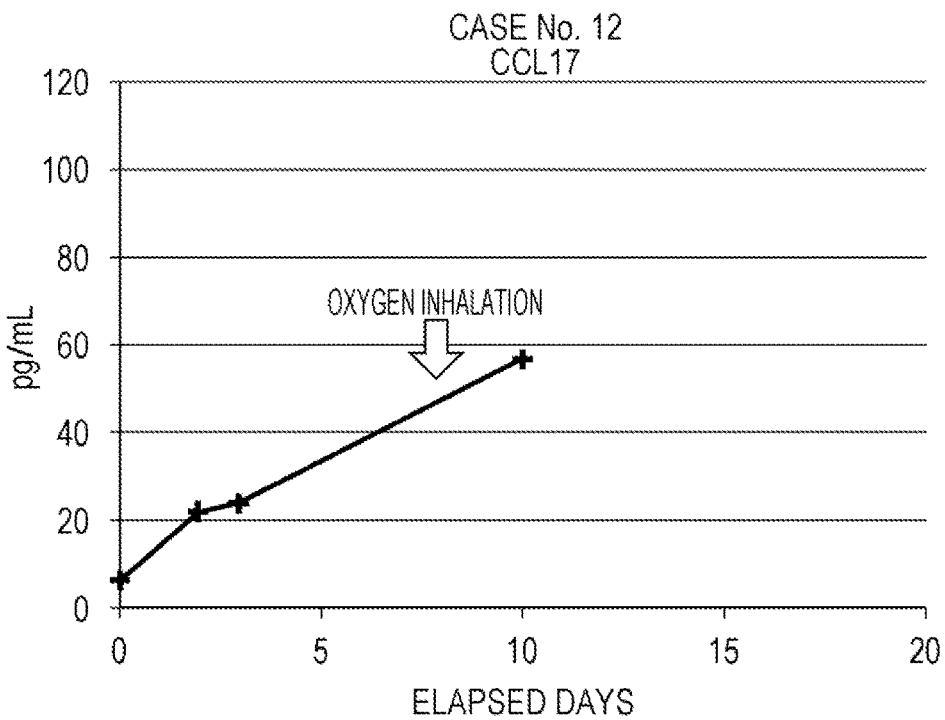
FIG. 10E is a graph showing transition of CCL17 concentration in serum of a patient in case No. 12.
Figure 10F:
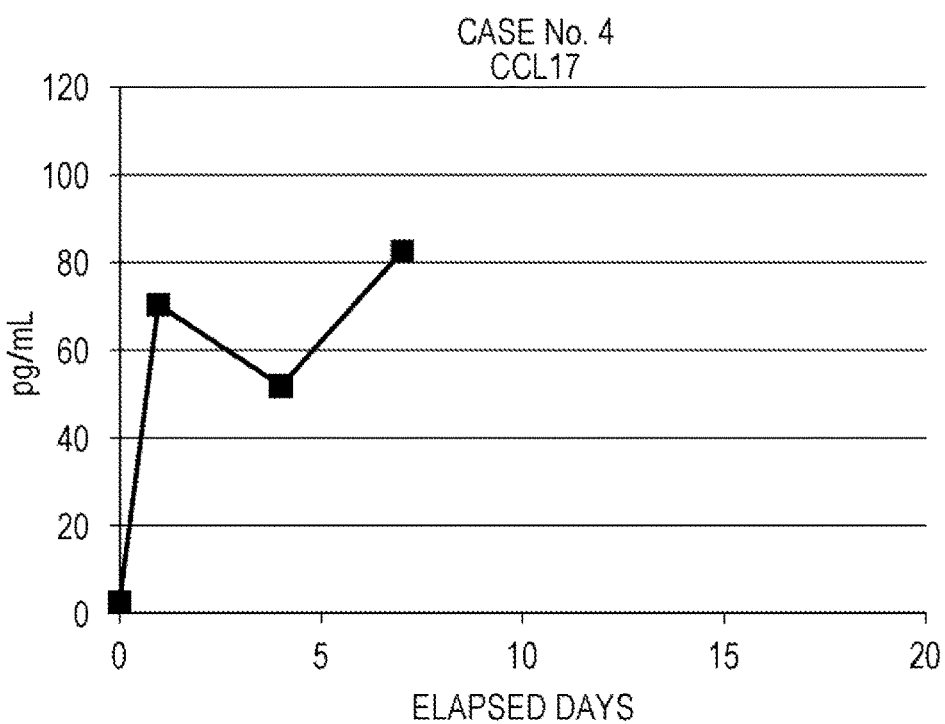
FIG. 10F is a graph showing transition of CCL17 concentration in serum of a patient in case No. 4.
Figure 10G:
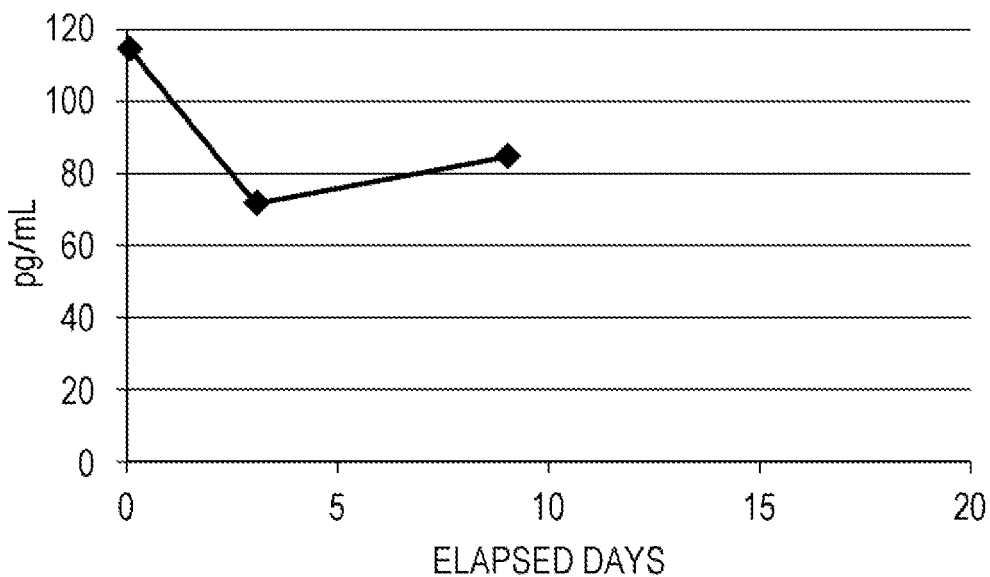
FIG. 10G is a graph showing transition of CCL17 concentration in serum of a patient in case No. 8.
Figure 10H:
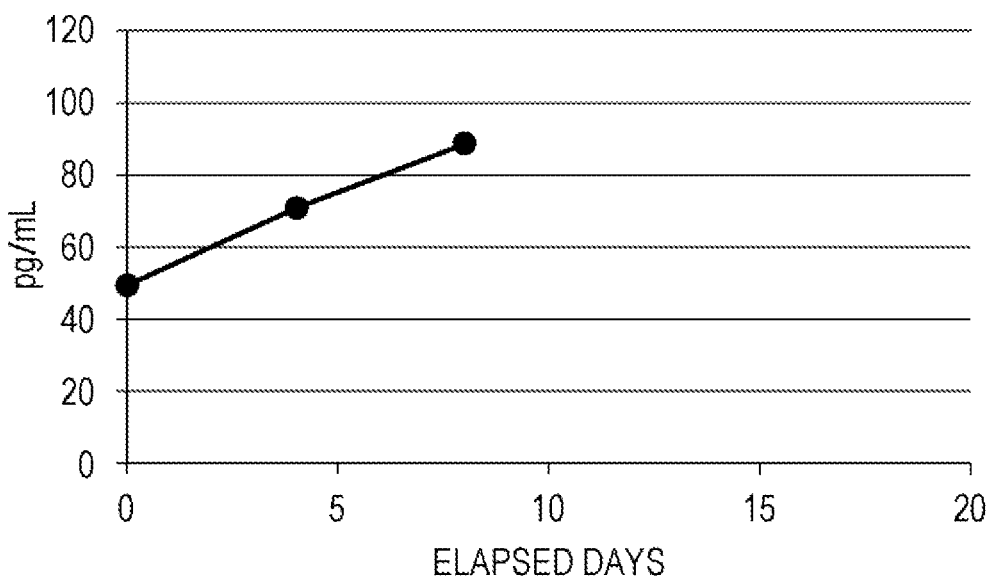
FIG. 10H is a graph showing transition of CCL17 concentration in serum of a patient in case No. 10.

A flow for predicting exacerbation of respiratory infection based on the measured value of CCL17 will be described with reference to FIG. 4F. In step S601, the CPU 310 acquires optical information (chemiluminescent signal) from the immunoassay device 20. In step S602, the CPU 310 calculates a measured value of CCL17 from the acquired optical information, and the CPU 310 stores the measured value of CCL17 in the hard disk 313. In step S603, the CPU 310 compares the calculated measured value of CCL17 with the threshold value corresponding to CCL17 stored in the hard disk 313. When the measured value of CCL17 is less than the threshold value, the process proceeds to step S604. In step S604, the CPU 310 stores in the hard disk 313 a determination result that the possibility of exacerbation of respiratory infection of the subject is high.

On the other hand, in step S603, when the measured value of CCL17 is greater than or equal to the threshold value, the process proceeds to step S605. In step S605, the CPU 310 stores in the hard disk 313 a determination result that the possibility of exacerbation of respiratory infection of the subject is low. In step S606, the CPU 310 outputs the determination result, and the CPU 310 displays the determination result on the display unit 302 or makes a printer to print the determination result. As a result, it is possible to provide a doctor or the like with an index to assist in predicting exacerbation of respiratory infection.

In another embodiment, three selected from the group consisting of IFNλ3, CXCL11, IP-10, IL-6 and CXCL9 are used as biomarkers. In this case, the CPU 310 acquires optical information (chemiluminescence signal) from the immunoassay device 20 for these three biomarkers. The CPU 310 calculates a measured value of each biomarker from the acquired optical information. The CPU 310 stores the measured value of each biomarker in the hard disk 313. The CPU 310 compares the measured value of each biomarker with the corresponding threshold value, and when the measured value of at least one biomarker is greater than or equal to the threshold value, the CPU 310 stores in the hard disk 313 a determination result that the possibility of exacerbation of respiratory infection of the subject is high. When the measured values of all biomarkers are less than the threshold value, the CPU 310 stores in the hard disk 313 a determination result that the possibility of exacerbation of respiratory infection of the subject is low. The CPU 310 outputs the determination result, and the CPU 310 displays the determination result on the display unit 302 or makes a printer to print the determination result.

In another embodiment, three selected from the group consisting of IFNλ3, CXCL11, IP-10, IL-6 and CXCL9 are used as biomarkers. In this case, the CPU 310 acquires optical information (chemiluminescence signal) from the immunoassay device 20 for these three biomarkers. The CPU 310 calculates a measured value of each biomarker from the acquired optical information. The CPU 310 stores the measured value of each biomarker in the hard disk 313. The CPU 310 compares the measured value of each biomarker with the corresponding threshold value, and when the measured values of all biomarkers are greater than or equal to the threshold value, the CPU 310 stores in the hard disk 313 a determination result that the possibility of exacerbation of respiratory infection of the subject is high. When the measured value of at least biomarker is less than the threshold value, the CPU 310 stores in the hard disk 313 a determination result that the possibility of exacerbation of respiratory infection of the subject is low. The CPU 310 outputs the determination result, and the CPU 310 displays the determination result on the display unit 302 or makes a printer to print the determination result.

In another embodiment, four selected from the group consisting of IFNλ3, CXCL11, IP-10, IL-6 and CXCL9 are used as biomarkers. In this case, the CPU 310 acquires optical information (chemiluminescence signal) from the immunoassay device 20 for these four biomarkers. The CPU 310 calculates a measured value of each biomarker from the acquired optical information. The CPU 310 stores the measured value of each biomarker in the hard disk 313. The CPU 310 compares the measured value of each biomarker with the corresponding threshold value, and when the measured value of at least one biomarker is greater than or equal to the threshold value, the CPU 310 stores in the hard disk 313 a determination result that the possibility of exacerbation of respiratory infection of the subject is high. When the measured values of all biomarkers are less than the threshold value, the CPU 310 stores in the hard disk 313 a determination result that the possibility of exacerbation of respiratory infection of the subject is low. The CPU 310 outputs the determination result, and the CPU 310 displays the determination result on the display unit 302 or makes a printer to print the determination result.

In another embodiment, four selected from the group consisting of IFNλ3, CXCL11, IP-10, IL-6 and CXCL9 are used as biomarkers. In this case, the CPU 310 acquires optical information (chemiluminescence signal) from the immunoassay device 20 for these four biomarkers. The CPU 310 calculates a measured value of each biomarker from the acquired optical information. The CPU 310 stores the measured value of each biomarker in the hard disk 313. The CPU 310 compares the measured value of each biomarker with the corresponding threshold value, and when the measured values of all biomarkers are greater than or equal to the threshold value, the CPU 310 stores in the hard disk 313 a determination result that the possibility of exacerbation of respiratory infection of the subject is high. When the measured value of at least biomarker is less than the threshold value, the CPU 310 stores in the hard disk 313 a determination result that the possibility of exacerbation of respiratory infection of the subject is low. The CPU 310 outputs the determination result, and the CPU 310 displays the determination result on the display unit 302 or makes a printer to print the determination result.

In another embodiment, five consisting of IFNλ3, CXCL11, IP-10, IL-6 and CXCL9 are used as biomarkers. In this case, the CPU 310 acquires optical information (chemiluminescence signal) from the immunoassay device 20 for five biomarkers. The CPU 310 calculates a measured value of each biomarker from the acquired optical information. The CPU 310 stores the measured value of each biomarker in the hard disk 313. The CPU 310 compares the measured value of each biomarker with the corresponding threshold value, and when the measured value of at least one biomarker is greater than or equal to the threshold value, the CPU 310 stores in the hard disk 313 a determination result that the possibility of exacerbation of respiratory infection of the subject is high. When the measured values of all biomarkers are less than the threshold value, the CPU 310 stores in the hard disk 313 a determination result that the possibility of exacerbation of respiratory infection of the subject is low. The CPU 310 outputs the determination result, and the CPU 310 displays the determination result on the display unit 302 or makes a printer to print the determination result.

In another embodiment, five consisting of IFNλ3, CXCL11, IP-10, IL-6 and CXCL9 are used as biomarkers. In this case, the CPU 310 acquires optical information (chemiluminescence signal) from the immunoassay device 20 for five biomarkers. The CPU 310 calculates a measured value of each biomarker from the acquired optical information. The CPU 310 stores the measured value of each biomarker in the hard disk 313. The CPU 310 compares the measured value of each biomarker with the corresponding threshold value, and when the measured values of all biomarkers are greater than or equal to the threshold value, the CPU 310 stores in the hard disk 313 a determination result that the possibility of exacerbation of respiratory infection of the subject is high. When the measured value of at least biomarker is less than the threshold value, the CPU 310 stores in the hard disk 313 a determination result that the possibility of exacerbation of respiratory infection of the subject is low. The CPU 310 outputs the determination result, and the CPU 310 displays the determination result on the display unit 302 or makes a printer to print the determination result.

One embodiment relates to a method for treating a respiratory infection. The method for treating a respiratory infection of the present embodiment includes measuring a biomarker in a specimen collected from a subject suffering from a respiratory infection or a subject suspected of having a respiratory infection, predicting exacerbation of respiratory infection based on a measured value of the biomarker, and performing medical intervention on a subject predicted to exacerbate respiratory infection in the predicting. Examples of the "medical intervention" include drug administration, surgery, immunotherapy, gene therapy, oxygenation procedures, heart-lung machine procedures, and the like. The drug can be appropriately selected from known therapeutic drugs for respiratory infections or candidate medicines therefor. For example, when the respiratory infection is SARS-CoV-2 infection, examples of the drug include drugs having an antiviral action, drugs that reduce inflammation, ACE inhibitors, and the like. Specific examples of the drug include favipiravir, lopinavir, ritonavir, nafamostat, camostat, remdesivir, ribavirin, ivermectin, ciclesonide, chloroquine, hydroxychloroquine, interferon, tocilizumab, sarilumab, tofasitinib, baricitinib, ruxolitinib, acalabrutinib, ravulizumab, eritoran, ibudilast, HLCM051, LY3127804, and the like.

Hereinafter, the present disclosure will be described in more detail by way of examples. Hereinafter, "HISCL" refers to a registered trademark of Sysmex Corporation.

EXAMPLES

Example 1

(1) Biological Sample

Serum obtained from 8 patients whose SARS-CoV-2 infection was confirmed by PCR test was used as a biological sample. The serum was prepared from blood collected at a plurality of time point from the day the patient was hospitalized. Information on each patient is shown in Table 1. In the table, "onset date" indicates the day when cold symptoms such as fever and cough appeared. "Severity" indicates a final medical condition of each patient after hospitalization. "Mild" indicates a case without pneumonia. "Moderate" indicates a case with pneumonia without oxygen demand. "Severe" indicates a case with pneumonia with oxygen demand. "Critical" indicates a case requiring intensive care management including mechanical ventilation management.

TABLE 1

| Case No. | Onset date | Hospitalization date | Age | Sex | Severity |
|---|---|---|---|---|---|
| 4 | 2020 Jan. 31 | 2020 Jan. 31 | 41 | M | moderate |
| 5 | 2020 Jan. 30 | 2020 Jan. 30 | 50 | F | severe |
| 7 | 2020 Feb. 5 | 2020 Feb. 11 | 63 | M | critical |
| 8 | 2020 Feb. 8 | 2020 Feb. 11 | 28 | F | mild |
| 9 | 2020 Jan. 27 | 2020 Feb. 12 | 83 | M | severe |
| 10 | 2020 Feb. 7 | 2020 Feb. 12 | 64 | F | mild |
| 11 | 2020 Feb. 6 | 2020 Feb. 13 | 63 | M | critical |
| 12 | 2020 Feb. 13 | 2020 Feb. 17 | 53 | M | severe |

(2) Measurement of Biomarkers
(2.1) Measurement of Chemokines and Cytokines

Concentrations of various chemokines and cytokines were measured using Bio-Plex Pro (trademark) Human Chemokine 40-Plex Panel (#171AK99MR2, Bio-Rad Laboratories, Inc.) and Bio-Plex Pro (trademark) Human Cytokine Screening 48-Plex Panel (#12007283, Bio-Rad Laboratories, Inc.). A Bio-Plex MAGPIX system (Bio-Rad Laboratories, Inc.) was used as a measuring device. Specific operation was performed according to an attached document of the kits and an attached document of the measuring device.

(2.2) Measurement of INFλ3 (IL-28B)

Concentration of INFλ3 as a cytokine not included in measurement items of the above kits was measured by a fully automatic immunoassay device HISCL-5000 (Sysmex Corporation) using the following R1 to R5 reagents. An R1 reagent (capture antibody reagent) was prepared by labeling an anti-hIL-28B antibody (clone name: Hyb-TA2650B) provided by the National Center for Global Health and Medicine with biotin by a conventional method, and dissolving the labeled antibody in 1% bovine serum albumin (BSA) and a 0.5% casein-containing buffer. As an R2 reagent (solid phase), a HISCL (registered trademark) R2 reagent (Sysmex Corporation) containing streptavidin-coupled magnetic particles was used. An R3 reagent (detection antibody reagent) was prepared by making an anti-rhIL-28B antibody (clone name: Hyb-TA2664) provided by the National Center for Global Health and Medicine into a Fab' fragment by a conventional method, labeling this Fab' fragment with ALP by a conventional method, and dissolving the labeled antibody in 1% BSA and a 0.5% casein-containing buffer. As an R4 reagent (measurement buffer solution), a HISCL R4 reagent (Sysmex Corporation) was used. As an R5 reagent (ALP substrate solution), a HISCL R5 reagent (Sysmex Corporation) was used. A method for preparing an anti-hIL-28B antibody and an anti-rhIL-28B antibody is described in Japanese Examined Patent No. 6081699.

A measurement procedure according to HISCL-5000 was as follows. After mixing serum (30 µL) and the R1 reagent (100 µL), the R2 reagent (30 µL) was added thereto. The magnetic particles in the obtained mixed solution were magnetically collected to remove the supernatant, and a HISCL washing solution (300 µL) was added to wash the magnetic particles. The supernatant was removed, and the R3 reagent (100 µL) was added to the magnetic particles and mixed. The magnetic particles in the obtained mixed solution were magnetically collected to remove the supernatant, and a HISCL washing solution (300 µL) was added to wash the magnetic particles. Supernatant was removed, and the R4 reagent (50 µL) and the R5 reagent (100 µL) were added to the magnetic particles, and the chemiluminescence intensity was measured. As a calibrator (antigen for preparing a calibration curve), hIL-28B (10-046) provided by the National Center for Global Health and Medicine was used. The calibrator was measured in the same manner as serum to prepare a calibration curve. The chemiluminescence intensity obtained by the measurement of each serum was applied to the calibration curve to determine the concentration of INFλ3.

(3) Measurement Results

From the measurement results of various chemokines and cytokines, IFNλ3, CXCL11, IP-10, IL-6, CXCL9 and CCL17 were found as biomarkers that can predict prognosis of SARS-CoV-2 infection. FIGS. 5 to 10 show graphs plotting measured values of each patient for IFNλ3, CXCL11, IP-10, IL-6, CXCL9 and CCL17. In the figures, "elapsed days" indicates the number of days from the day when the patient was hospitalized (elapsed days 0). Arrows in the figures indicate a time point when the patient was treated with an oxygen inhaling apparatus or a heart-lung machine. In the figures, "IFNL3" means IFNλ3.

As can be seen from A to E in FIGS. 5 to 9, patients in case Nos. 5, 7, 9, 11 and 12 tended to exacerbate infection after IFNλ3, CXCL11, IP-10, IL-6 and CXCL9 showed high values. The patient in case No. 9 had relatively low measured values of IFNλ3 as compared to other severely ill patients, but tended to have high measured values of CXCL11, IP-10, IL-6 and CXCL9. On the other hand, as can be seen from F, G and H in FIGS. 5 to 9, patients in case Nos. 4, 8 and 10 tended to show low measured values of IFNλ3, CXCL11, IP-10, IL-6 and CXCL9 as compared to severely ill patients. These results suggested that IFNλ3, CXCL11, IP-10, IL-6 and CXCL9 can be used as biomarkers to predict exacerbation of the respiratory infection.

As can be seen from FIGS. 10A to 10H, the measured values of CCL17 tended to show high values in mildly ill patients as compared to severely ill patients. This result suggested that CCL17 can be used as a biomarker to find a patient with the possibility of exacerbation of respiratory infection of the subject is low, by using in combination with IFNλ3, CXCL11, IP-10, IL-6 or CXCL9.

Example 2

Figure 11A:
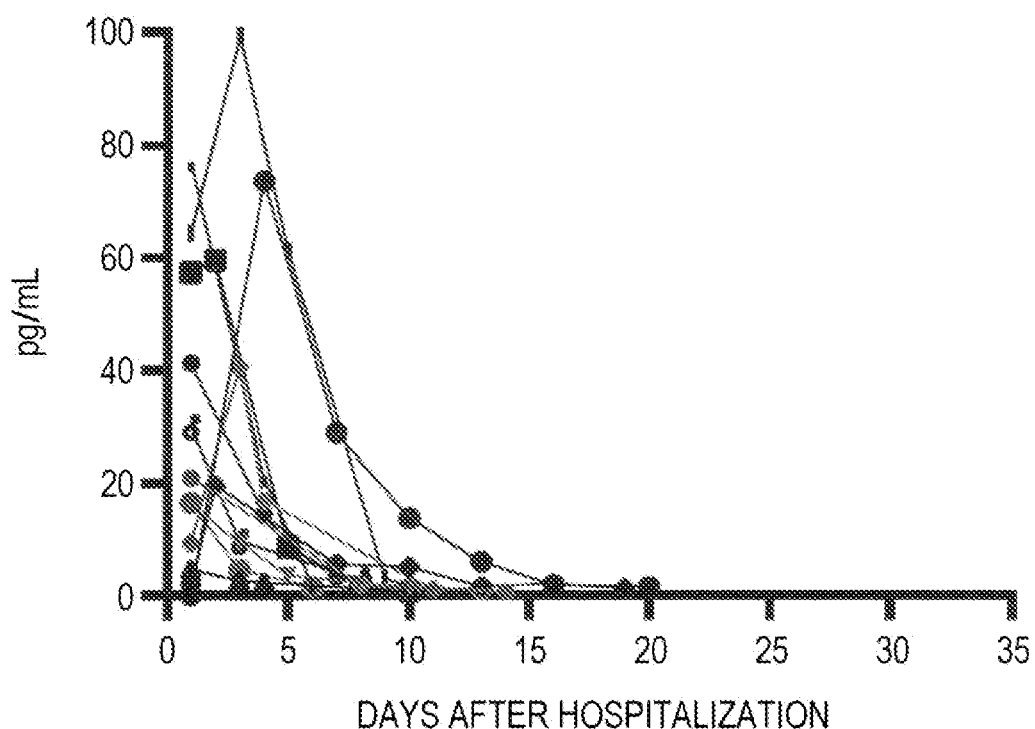
FIG. 11A is a graph showing transition of IFNλ3 concentrations in sera of patients in group H.
Figure 11B:
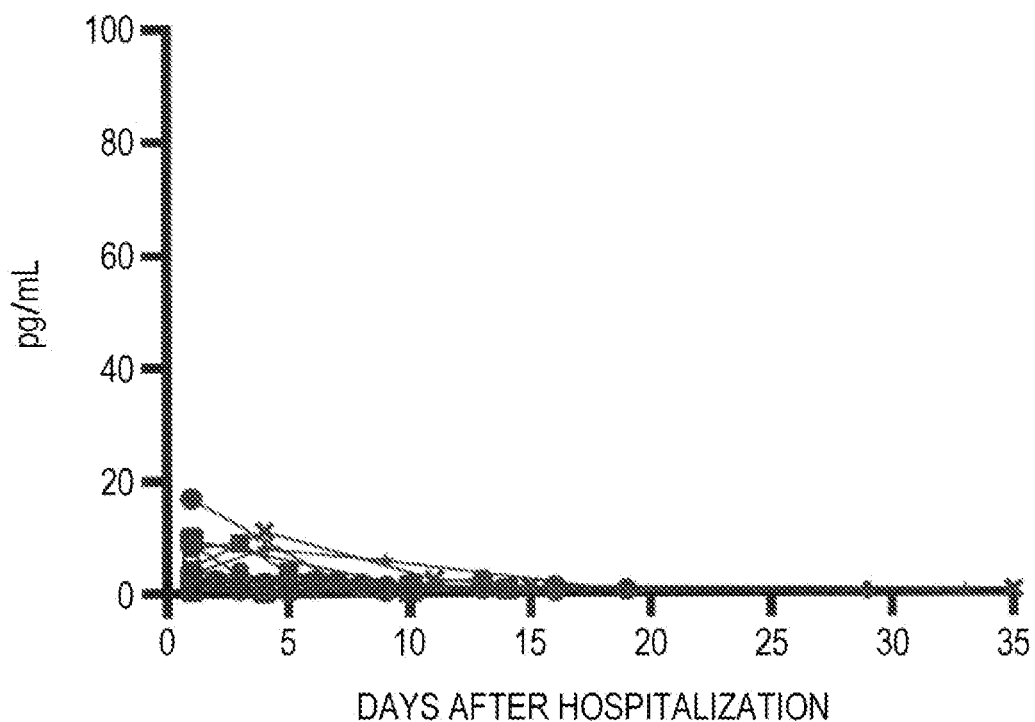
FIG. 11B is a graph showing transition of IFNλ3 concentrations in sera of patients in group L.
Figure 12A:
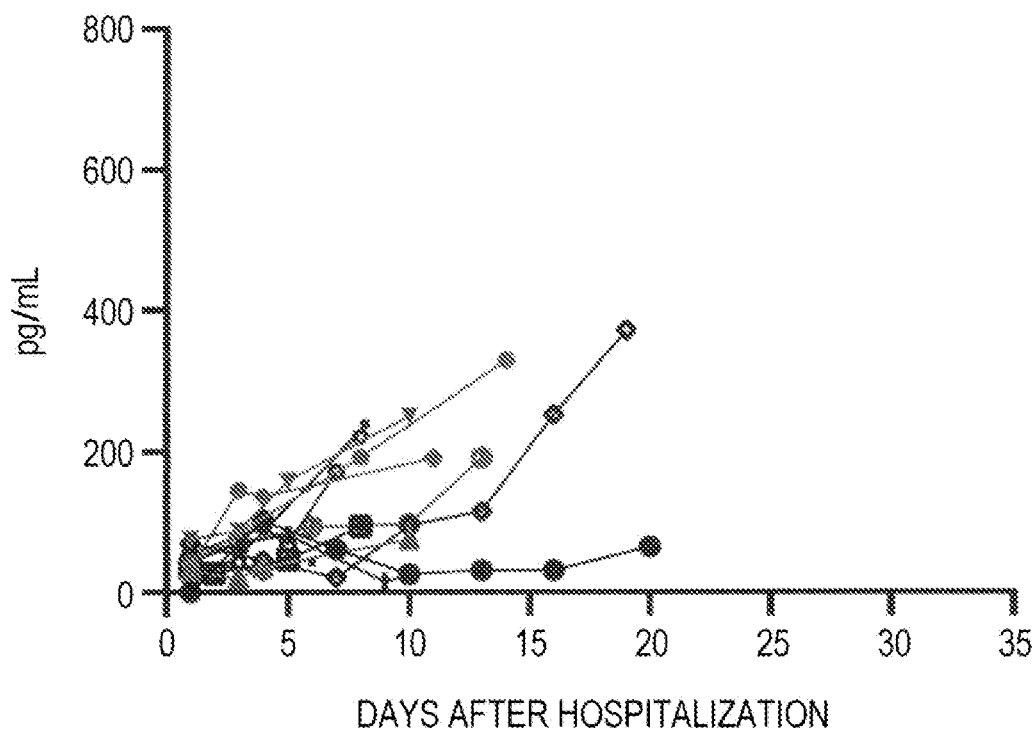
FIG. 12A is a graph showing transition of CCL17 concentrations in sera of patients in group H.
Figure 12B:
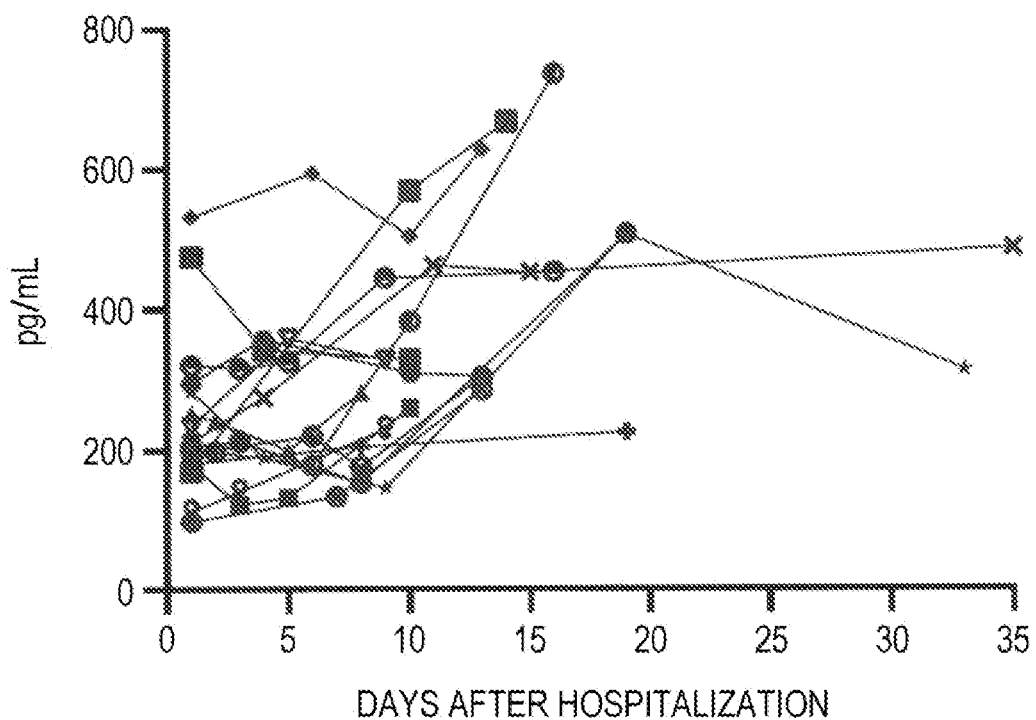
FIG. 12B is a graph showing transition of CCL17 concentrations in sera of patients in group L.
Figure 13A:
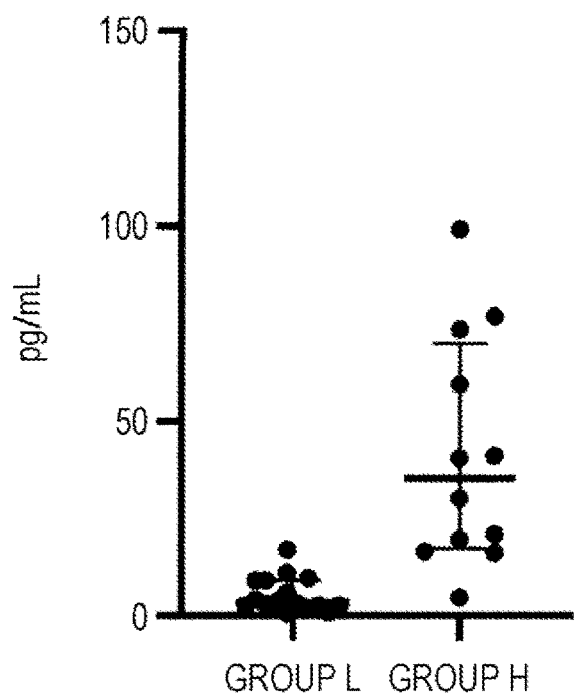
FIG. 13A is a graph plotting IFNλ3 concentrations in sera of patients in groups H and L.
Figure 13B:
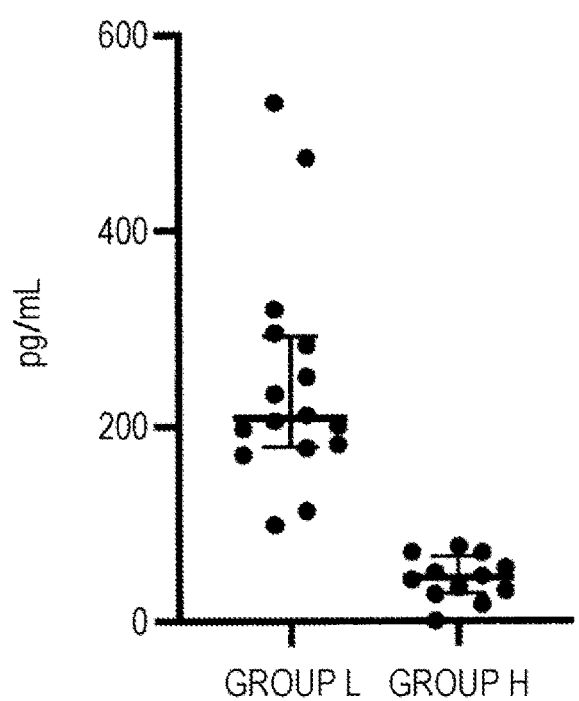
FIG. 13B is a graph plotting CCL17 concentrations in sera of patients in groups H and L.

(1) Biological Sample
Serum obtained from 20 patients whose SARS-CoV-2 infection was confirmed by PCR test was used as a biological sample. The serum was prepared from blood collected at a plurality of time point from the day the patient was hospitalized. Severity of the 20 patients was mild in 2, moderate in 11, severe in 2, and critical in 5.
(2) Measurement of Biomarkers
Concentrations of IFNλ3 and CCL17 in the plasma of each patient were measured in the same manner as in Example 1. FIGS. 11 and 12 show graphs plotting the measured values of 28 patients, including 20 patients in Example 2 and 8 patients in Example 1, for IFNλ3 and CCL17. FIG. 11A shows IFNλ3 measured values for critical and severe patients, and FIG. 11B shows IFNλ3 measured values for moderate and mild patients. FIG. 12A shows CCL17 measured values for critical and severe patients, and FIG. 12B shows CCL17 measured values for moderate and mild patients. In the figures, "Days after hospitalization" indicates the number of days from the day when the patient was hospitalized (0 day).
(3) Analysis of Measured Values of Biomarkers
Analysis was performed on the measured values of 28 patients, including 20 patients in Example 2 and 8 patients in Example 1. Of the 28 patients, patients with mild or moderate severity were classified as "low risk group" (hereinafter referred to as "L group"), patients with severe or critical severity were classified as "high risk group" (hereinafter referred to as "H group"), and concentrations of IFNλ3 and CCL17 in each group were plotted. The results are shown in FIGS. 13A and 13B. Horizontal lines in the figures indicate first quartile, median and third quartile of the biomarker concentration of each group.

Figure 14A:
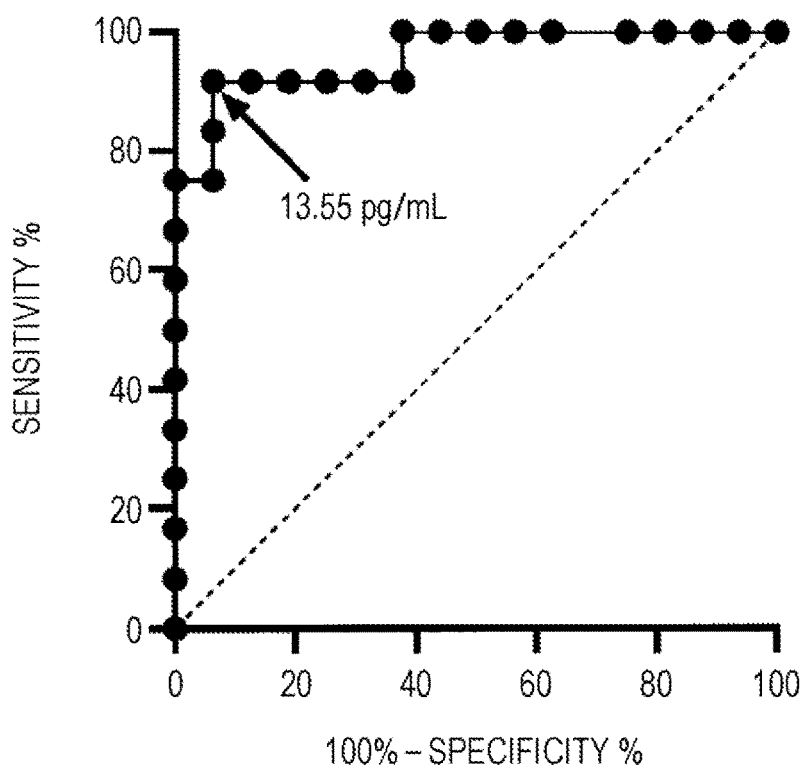
FIG. 14A is a ROC (receiver operating characteristic) curve when determining exacerbation of respiratory infection based on IFNλ3 concentration.
Figure 14B:
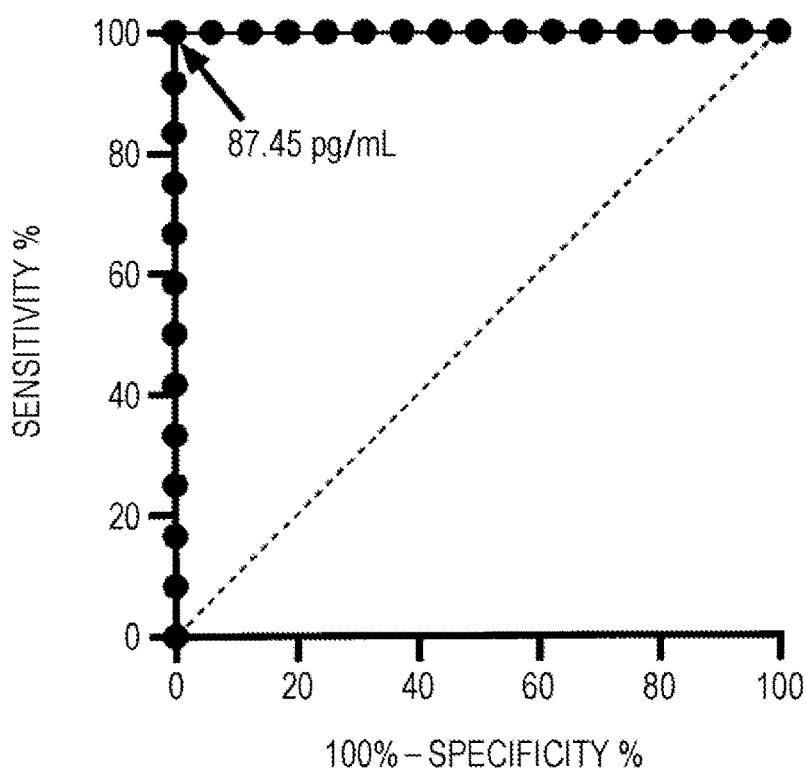
FIG. 14B is a ROC curve when determining exacerbation of respiratory infection based on CCL17 concentration.
Figure 15A:
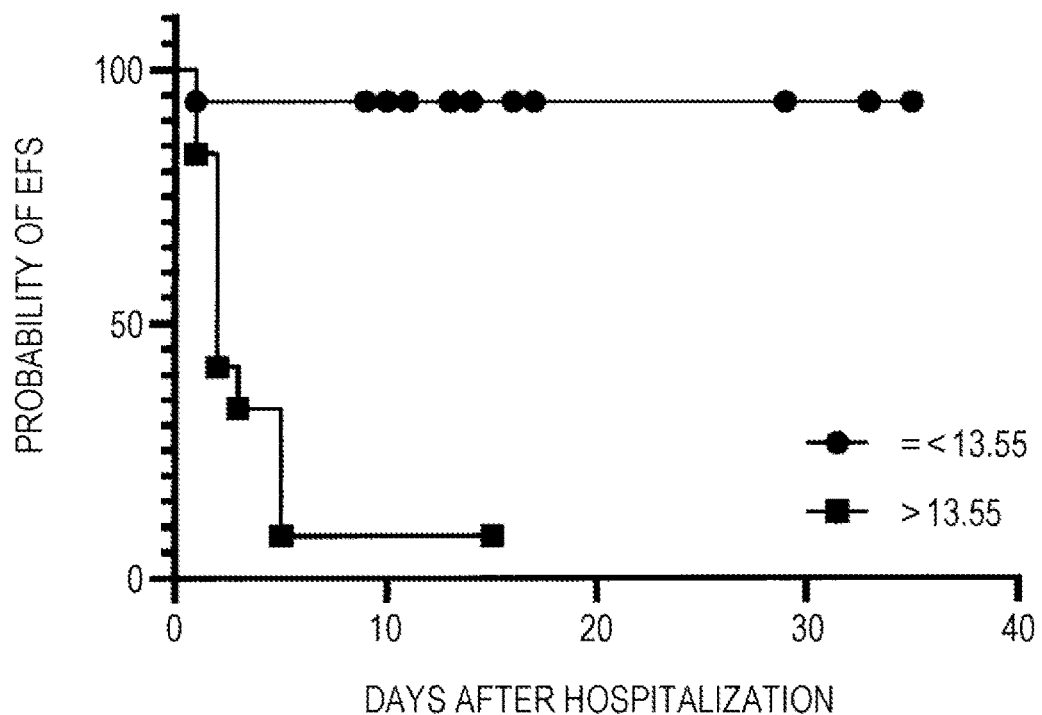
FIG. 15A is a Kaplan-Meier curve showing a relationship between period after hospitalization and event-free survival rate in a group of patients with IFNλ3 concentration greater than or equal to a cutoff value and in a group of patients with IFNλ3 concentration less than the cutoff value.
Figure 15B:
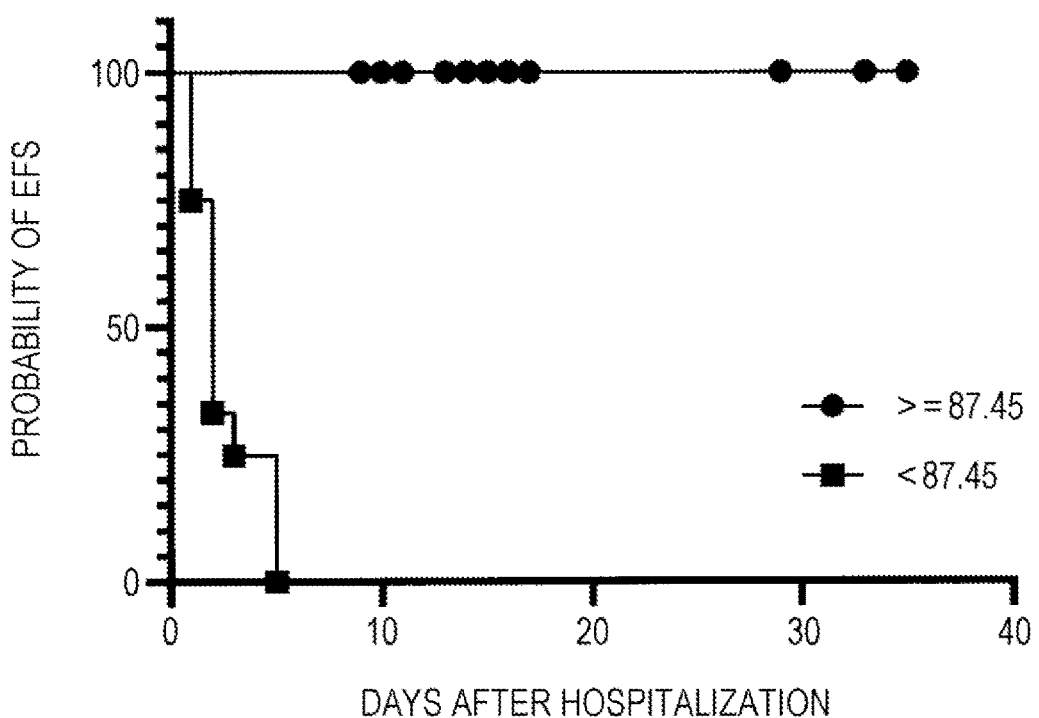
FIG. 15B is a Kaplan-Meier curve showing a relationship between period after hospitalization and event-free survival rate in a group of patients with CCL17 concentration greater than a cutoff value and in a group of patients with CCL17 concentration less than or equal to the cutoff value.

The biomarker concentrations of 28 patients were analyzed by ROC, and an optimum cutoff value (threshold value) for distinguishing between the L group and the H group was set. For 28 patients, the set cutoff values were used to calculate sensitivity, specificity and area under the curve (AUC) of determination when determining whether or not the possibility of exacerbation of respiratory infection is high. The obtained ROC curves are shown in FIGS. 14A and 14B. The cutoff values of IFNλ3 and CCL17, and the sensitivity, specificity, AUC and p-values of determination using the cutoff values are shown in Table 2. Event-free survival (EFS) after hospitalization was examined by Kaplan-Meier method for two patient groups classified based on the cutoff values. The obtained Kaplan-Meier curves are shown in FIGS. 15A and 15B.

TABLE 2

| Biomarker | Cutoff value (pg/mL) | Sensitivity (%) | Specificity (%) | AUC | p |
|---|---|---|---|---|---|
| INF λ 3 | 13.55 | 91.67 (64.61-99.57) | 93.75 (71.67-99.68) | 0.96 (0.89-1.0) | <0.001 |
| CCL17 | 87.45 | 100 (75.75-100) | 100 (80.64-100) | 1.0 (1.0-1.0) | <0.001 |

It was shown from Table 2 that IFNλ3 and CCL17 are biomarkers that allow prediction of exacerbation of respiratory infection. It was shown from FIG. 15A that the possibility of exacerbation of respiratory infection is high when the measured value of IFNλ3 is greater than the cutoff value, and the possibility of exacerbation of respiratory infection is low when the measured value of IFNλ3 is less than or equal to the cutoff value. It was shown from FIG. 15B that the possibility of exacerbation of respiratory infection is high when the measured value of CCL17 is less than the cutoff value, and the possibility of exacerbation of respiratory infection is low when the measured value of CCL17 is greater than or equal to the cutoff value.

What is claimed is:

1. A method for assisting prediction of exacerbation of a respiratory infection, comprising:
measuring a biomarker in a specimen collected from a subject suffering from the respiratory infection or a subject suspected of having the respiratory infection, wherein the biomarker is one or more of IFNλ3 and CCL17, and a measured value of the biomarker is an index to predict exacerbation of the respiratory infection of the subject,
identifying a subject having the measured value of IFNλ3 greater than or equal to a threshold value corresponding to IFNλ3, and/or the measured value of CCL17 less than a threshold value corresponding to CCL17,
wherein a possibility of exacerbation of the respiratory infection of the subject is suggested to be high if the biomarker is IFNλ3 and the measured value of IFNλ3 is greater than or equal to a threshold value corresponding to IFNλ3, and/or if the biomarker is CCL17 and the measured value of CCL17 is less than a threshold value corresponding to CCL17, and
administering to said subject an antiviral drug, an anti-inflammatory drug or an ACE inhibitor capable of treating the respiratory infection.

2. The method according to claim 1,
wherein the biomarker is IFNλ3, and
wherein if the measured value of IFNλ3 is less than the threshold value corresponding to IFNλ3, the possibility of exacerbation of the respiratory infection of the subject is suggested to be low.

3. The method according to claim 1,
wherein the biomarker is CCL17, and
wherein if the measured value of CCL17 is greater than or equal to the threshold value corresponding to CCL17, the possibility of exacerbation of the respiratory infection of the subject is suggested to be low.

4. The method according to claim 1, wherein the index is a temporal change in the measured value of the biomarker in the subject.

5. The method according to claim 1, wherein the specimen is whole blood, plasma or serum.

6. The method according to claim 1, wherein the respiratory infection is an infection caused by a virus.

7. The method according to claim 6, wherein the virus is α-coronavirus, β-coronavirus, γ-coronavirus or δ-coronavirus.

8. The method according to claim 7, wherein
the β-coronavirus is any one of SARS-CoV-2, HCoV-OC43, HCoV-HKU1, SARS-CoV, Bat SL-CoV-WIV1, BtCoV-HKU4, BtCoV-HKU5, MERS-COV and BtCoV-HKU9.

9. A method for assisting prediction of exacerbation of a respiratory infection, comprising:
monitoring a measured value of a biomarker in a specimen collected from a subject suffering from the respiratory infection or a subject suspected of having the respiratory infection,
the monitoring comprising:
acquiring measured values of the biomarker using specimens collected from the subject at a plurality of time points,
wherein the biomarker is one or more of IFNλ3 and CCL17, and the measured values are indices to predict exacerbation of the respiratory infection of the subject,
identifying a subject having the measured value of IFNλ3 greater than or equal to a threshold value corresponding to IFNλ3 at at least one of the plurality of time points, and/or the measured value of CCL17 less than a threshold value corresponding to CCL17 at at least one of the plurality of time points,
wherein a possibility of exacerbation of the respiratory infection of the subject is suggested to be high if the biomarker is IFNλ3 and the measured value of IFNλ3 is greater than or equal to a threshold value corresponding to IFNλ3 at at least one of the plurality of time points, and/or if the biomarker is CCL17 and the measured value of CCL17 is less than a threshold value corresponding to CCL17 at at least one of the plurality of time points, and
administering to said subject an antiviral drug, an anti-inflammatory drug or an ACE inhibitor capable of treating the respiratory infection.

10. The method according to claim 9,
wherein the biomarker is IFNλ3, and
wherein if the measured value of the biomarker is less than the threshold value corresponding to FNλ3 at any of the plurality of time points, the possibility of exacerbation of the respiratory infection of the subject is suggested to be low.

11. The method according to claim 9,
wherein the biomarker is CCL17, and
wherein if the measured value of CCL17 is greater than or equal to the threshold value corresponding to CCL17 at any of the plurality of time points, the possibility of exacerbation of the respiratory infection of the subject is suggested to be low.

* * * * *

SEQUENCE LISTING

<160> NUMBER OF SEQ ID NOS: 12

<210> SEQ ID NO 1
<211> LENGTH: 200
<212> TYPE: PRT
<213> ORGANISM: Homo sapiens

<400> SEQUENCE: 1

Met Lys Leu Asp Met Thr Gly Asp Cys Met Pro Val Leu Val Leu Met
1               5                   10                  15

Ala Ala Val Leu Thr Val Thr Gly Ala Val Pro Val Ala Arg Leu Arg
            20                  25                  30

Gly Ala Leu Pro Asp Ala Arg Gly Cys His Ile Ala Gln Phe Lys Ser
            35                  40                  45

Leu Ser Pro Gln Glu Leu Gln Ala Phe Lys Arg Ala Lys Asp Ala Leu
    50                  55                  60

Glu Glu Ser Leu Leu Leu Lys Asp Cys Lys Cys Arg Ser Arg Leu Phe
65                  70                  75                  80

Pro Arg Thr Trp Asp Leu Arg Gln Leu Gln Val Arg Glu Arg Pro Val
                85                  90                  95

Ala Leu Glu Ala Glu Leu Ala Leu Thr Leu Lys Val Leu Glu Ala Thr
            100                 105                 110

Ala Asp Thr Asp Pro Ala Leu Gly Asp Val Leu Asp Gln Pro Leu His
            115                 120                 125

Thr Leu His His Ile Leu Ser Gln Leu Arg Ala Cys Ile Gln Pro Gln
130                 135                 140

Pro Thr Ala Gly Pro Arg Thr Arg Gly Arg Leu His His Trp Leu His
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
            180                 185                 190

Val Ala Ser Gly Asp Leu Cys Val
            195                 200

<210> SEQ ID NO 2
<211> LENGTH: 200
<212> TYPE: PRT
<213> ORGANISM: Homo sapiens

<400> SEQUENCE: 2

Met Lys Leu Asp Met Thr Gly Asp Cys Met Pro Val Leu Val Leu Met
1               5                   10                  15

Ala Ala Val Leu Thr Val Thr Gly Ala Val Pro Val Ala Arg Leu Arg
            20                  25                  30

Gly Ala Leu Pro Asp Ala Arg Gly Cys His Ile Ala Gln Phe Lys Ser
            35                  40                  45

Leu Ser Pro Gln Glu Leu Gln Ala Phe Lys Arg Ala Lys Asp Ala Leu
    50                  55                  60

Glu Glu Ser Leu Leu Leu Lys Asp Cys Lys Cys Arg Ser Arg Leu Phe
65                  70                  75                  80

Pro Arg Thr Trp Asp Leu Arg Gln Leu Gln Val Arg Glu Arg Pro Val
                85                  90                  95

Ala Leu Glu Ala Glu Leu Ala Leu Thr Leu Lys Val Leu Glu Ala Thr
            100                 105                 110

Ala Asp Thr Asp Pro Ala Leu Gly Asp Val Leu Asp Gln Pro Leu His
            115                 120                 125

Thr Leu His His Ile Leu Ser Gln Leu Arg Ala Cys Ile Gln Pro Gln
130                 135                 140

Pro Thr Ala Gly Pro Arg Thr Arg Gly Arg Leu His His Trp Leu His
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
            180                 185                 190

Val Ala Ser Gly Asp Leu Cys Val
            195                 200

<210> SEQ ID NO 3
<211> LENGTH: 124
<212> TYPE: PRT
<213> ORGANISM: Mus musculus

<400> SEQUENCE: 3

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg His Ile Pro Asp Lys Arg Leu Glu Trp Val
        35                  40                  45

Ala Thr Ile Thr Gly Gly Ser Tyr Thr Tyr Tyr Pro Asp Gly Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Gly Asp Tyr Gly Ser Asn Tyr Leu Tyr Trp Tyr Phe Asp
            100                 105                 110

Val Trp Gly Ala Gly Thr Thr Val Thr Val Ser Ser
        115                 120

<210> SEQ ID NO 4
<211> LENGTH: 108
<212> TYPE: PRT
<213> ORGANISM: Mus musculus

<400> SEQUENCE: 4

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105

<210> SEQ ID NO 5
<211> LENGTH: 120
<212> TYPE: PRT
<213> ORGANISM: Mus musculus

<400> SEQUENCE: 5

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Gly Gly Gly Ser Thr Asn Tyr Pro Asp Thr Val
    50                  55                  60

Lys Gly Arg Phe Thr Ile Ser Arg Asp Asn Ala Lys Asn Thr Leu Tyr
 65                  70                  75                  80

Leu Gln Met Ser Arg Leu Lys Ser Glu Asp Thr Ala Met Tyr Tyr Cys
                 85                  90                  95

Ala Arg Pro Ser Leu Leu Arg Ser Ala Trp Phe Ala Tyr Trp Gly Gln
            100                 105                 110

Gly Thr Leu Val Thr Val Ser Ala
            115                 120

<210> SEQ ID NO 6
<211> LENGTH: 108
<212> TYPE: PRT
<213> ORGANISM: Mus musculus

<400> SEQUENCE: 6

Asp Ile Val Leu Thr Gln Ser Pro Ala Ser Leu Ala Val Ser Leu Gly
 1               5                  10                  15

Gln Arg Ala Thr Ile Ser Tyr Arg Ala Ser Lys Ser Val Ser Thr Ser
                 20                  25                  30

Gly Tyr Ser Tyr Met His Trp Asn Gln Gln Lys Pro Gly Gln Pro Pro
             35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                 85                  90                  95

Glu Leu Thr Arg Ser Glu Gly Gly Pro Ser Trp Lys
            100                 105

<210> SEQ ID NO 7
<211> LENGTH: 117
<212> TYPE: PRT
<213> ORGANISM: Mus musculus

<400> SEQUENCE: 7

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
                 20                  25                  30

Tyr Ile His Trp Val Lys Gln Arg Pro Glu Gln Gly Leu Glu Trp Ile
             35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Phe Cys
                 85                  90                  95

Ala Pro Tyr Gly Tyr Asp Tyr Phe Asp Tyr Trp Gly Gln Gly Thr Thr
            100                 105                 110

Leu Thr Val Ser Ser
            115

<210> SEQ ID NO 8
<211> LENGTH: 108

```
<212> TYPE: PRT
<213> ORGANISM: Mus musculus

<400> SEQUENCE: 8

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105

<210> SEQ ID NO 9
<211> LENGTH: 117
<212> TYPE: PRT
<213> ORGANISM: Mus musculus

<400> SEQUENCE: 9

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Phe Cys
                85                  90                  95

Ala Pro Tyr Gly Tyr Asp Tyr Phe Asp Tyr Trp Gly Gln Gly Thr Thr
            100                 105                 110

Leu Thr Val Ser Ser
        115

<210> SEQ ID NO 10
<211> LENGTH: 108
<212> TYPE: PRT
<213> ORGANISM: Mus musculus

<400> SEQUENCE: 10

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
```

```
                65                  70                  75                  80
Pro Val Glu Glu Glu Asp Ala Ala Thr Tyr Tyr Cys Gln His Ile Arg
                            85                  90                  95

Glu Leu Thr Arg Ser Glu Gly Gly Pro Ser Trp Lys
                100                 105

<210> SEQ ID NO 11
<211> LENGTH: 117
<212> TYPE: PRT
<213> ORGANISM: Mus musculus

<400> SEQUENCE: 11

Glu Val Gln Leu Gln Gln Ser Gly Ala Glu Leu Val Lys Pro Gly Ala
1               5                   10                  15

Ser Val Thr Leu Ser Cys Thr Ala Ser Gly Phe Asn Ile Arg Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Ile Lys Tyr Asp Pro Lys Phe
    50                  55                  60

Gln Gly Lys Ala Thr Ile Thr Ala Asp Thr Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Pro Tyr Gly Tyr Asp Tyr Phe Asp Tyr Trp Gly Gln Gly Thr Thr
                100                 105                 110

Leu Thr Val Ser Ser
        115

<210> SEQ ID NO 12
<211> LENGTH: 108
<212> TYPE: PRT
<213> ORGANISM: Mus musculus

<400> SEQUENCE: 12

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
                100                 105
```